US009029120B2

(12) United States Patent
Roberts et al.

(10) Patent No.: US 9,029,120 B2
(45) **Date of Patent: *May 12, 2015**

(54) MODIFIED PHOTOSYNTHETIC MICROORGANISMS FOR PRODUCING TRIGLYCERIDES

(71) Applicant: Matrix Genetics, LLC, Seattle, WA (US)

(72) Inventors: James Roberts, Seattle, WA (US); Fred Cross, Seattle, WA (US); Paul Warrener, Seattle, WA (US); Ernesto Javier Munoz, Seattle, WA (US); Martin Henry Lee, Seattle, WA (US); Khadidja Romari, Seattle, WA (US); Kimberly Marie Kotovic, Seattle, WA (US); Jason W. Hickman, Seattle, WA (US)

(73) Assignee: Matrix Genetics, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,025

(22) Filed: Feb. 6, 2013

(65) Prior Publication Data

US 2013/0143284 A1 Jun. 6, 2013

Related U.S. Application Data

(63) Continuation of application No. 12/605,204, filed on Oct. 23, 2009, now Pat. No. 8,394,621.

(60) Provisional application No. 61/107,979, filed on Oct. 23, 2008.

(51) Int. Cl.

| | |
|---|---|
| ***C12N 9/00*** | (2006.01) |
| ***C12N 15/79*** | (2006.01) |
| ***C12N 1/20*** | (2006.01) |
| ***C12N 9/10*** | (2006.01) |
| ***C12N 9/16*** | (2006.01) |
| ***C12P 7/64*** | (2006.01) |

(52) U.S. Cl.

CPC *C12N 15/79* (2013.01); *C12N 1/20* (2013.01); *C12N 9/1029* (2013.01); *C12N 9/16* (2013.01); *C12N 9/93* (2013.01); *C12P 7/6409* (2013.01); *C12P 7/6463* (2013.01)

(58) Field of Classification Search

CPC .......................................................... C12R 1/00

See application file for complete search history.

(56) References Cited

U.S. PATENT DOCUMENTS

| | | | | |
|---|---|---|---|---|
| 6,306,639 | B1 | 10/2001 | Woods et al. | |
| 7,118,896 | B2 | 10/2006 | Kalscheuer et al. | |
| 7,157,619 | B1 | 1/2007 | Lassner et al. | |
| 7,427,593 | B1 | 9/2008 | Dahlqvist et al. | |
| 7,498,026 | B2 | 3/2009 | Dahlqvist et al. | |
| 7,794,969 | B1 | 9/2010 | Reppas et al. | |
| 8,394,621 | B2 * | 3/2013 | Roberts et al. | 435/252.1 |
| 2003/0233675 | A1 | 12/2003 | Cao et al. | |
| 2006/0137043 | A1 | 6/2006 | Puzio et al. | |
| 2007/0269859 | A1 | 11/2007 | Lassner et al. | |
| 2008/0160592 | A1 | 7/2008 | Dahlqvist et al. | |
| 2009/0035832 | A1 | 2/2009 | Koshland, Jr. | |
| 2009/0155864 | A1 | 6/2009 | Bauer et al. | |
| 2009/0215179 | A1 | 8/2009 | Gressel et al. | |
| 2009/0298143 | A1 | 12/2009 | Roessler et al. | |
| 2010/0081178 | A1 | 4/2010 | Roberts et al. | |
| 2010/0184169 | A1 | 7/2010 | Roberts et al. | |
| 2010/0251601 | A1 | 10/2010 | Hu et al. | |
| 2010/0255551 | A1 | 10/2010 | Roberts et al. | |
| 2011/0053216 | A1 | 3/2011 | Vermaas | |
| 2011/0250659 | A1 | 10/2011 | Roberts et al. | |

FOREIGN PATENT DOCUMENTS

| | | |
|---|---|---|
| WO | WO2008119082 | 10/2008 |
| WO | WO2008130437 | 10/2008 |
| WO | WO2009036095 | 3/2009 |
| WO | WO2009062190 | 5/2009 |
| WO | WO2009076559 | 6/2009 |
| WO | WO2009089185 | 6/2009 |
| WO | WO2009111513 | 9/2009 |
| WO | WO2010006312 | 1/2010 |
| WO | WO2010017245 | 2/2010 |
| WO | WO2010033921 | 3/2010 |
| WO | WO2010036951 | 4/2010 |
| WO | WO2010044960 | 4/2010 |
| WO | WO2010048568 | 4/2010 |
| WO | WO2010062707 | 6/2010 |
| WO | WO2010075440 | 7/2010 |
| WO | WO2010075483 | 7/2010 |
| WO | WO2010078584 | 7/2010 |
| WO | WO2011008535 | 1/2011 |
| WO | WO2011008565 | 1/2011 |
| WO | WO2011127069 | 10/2011 |

OTHER PUBLICATIONS

Marin et al., Microbiology, 152, p. 2023-2030, 2006.*

The European Office Action mailed Apr. 8, 2013 for European patent application No. , a counterpart foreign application of US patent application No. 09741171.4, 4 pages.

(Continued)

*Primary Examiner* — Ruth Davis

(74) *Attorney, Agent, or Firm* — Lee & Hayes, PLLC

(57) ABSTRACT

This disclosure describes genetically modified photosynthetic microorganisms, including Cyanobacteria, that contain one or more exogenous genes encoding a diacyglycerol acyltransferase, a phosphatidate phosphatase, and/or an acetyl-CoA carboxylase, and which are capable of producing increased amounts of fatty acids and/or synthesizing triglycerides.

14 Claims, 6 Drawing Sheets

(56) References Cited

OTHER PUBLICATIONS

The European Office Action mailed Mar. 5, 2014 for European patent application No. 09741171.4, a counterpart foreign application of US patent No. 8,394,621, 6 pages.
Song, et al., "Exploitation of Oil-bearing Microalgae for Biodiesel", Chinese Journal of Biotechnology, vol. 24, No. 1, Mar. 1, 2008, pp. 341-348, retrieved on Mar. 1, 2008.
Wada, et al., "Temperature-Induced Changes in the Fatty Acid Composition of the Cyanobacterium, *Synechocystis* PCC6803", Plant Physiology, American Society of Plant Physiologists, Rockville, MD, US, vol. 92, Jan. 1, 1009, pp. 1062-1069.
Acreman, "Algae and cyanobacteria: isolation, culture and long-term maintenance", Journal of Industrial Microbiology, vol. 13, 1994, pp. 193-194.
Alvarez, et al., "Triacylglycerols in prokaryotic microorganisms", Appl Microbiol Biotechnol, vol. 60, 2002, pp. 367-376.
Bagchi, et al., "A *Synechococcus elongatus* PCC 7942 mutant with a higher tolerance toward teh herbicide bentazone also confers resistsance to sodium chloride stress", Photosynth Res, vol. 92, 2007, pp. 87-101.
Christie, "Coenzyme A and Acyl Carrier Protein: Structure, Occurrence, Biology and Analysis", retrieved on Sep. 14, 2012, at lipidlibrary.aocs.org, Scottish Crop Research Institute, Feb. 24, 2011, pp. 1-4.
Chungjatupornchai, et al., "Isolation adn Characterization of *Synechococcus* PCC7942 Promoters: tRNApro Gene Functions as a Promoter", Current Microbiology vol. 38, 1999, pp. 210-216.
Coleman, et al., "Physiological and Nutritional Regulation of Enzymes of Triacylglycerol Synthesis", Annu. Rev. Nutr., 2000, vol. 20, pp. 77-103.
Dahlqvist, et al., "Phospholipid: diacylglycerol acyltransferase: An enzyme that catalyzes the acyl-CoA-independent formation of triacylglycerol in yeast and plants", PNAS, Jun. 6, 2000, vol. 97, No. 12, pp. 6487-6492.
Daniel, et al., "Induction of a Novel Class of Diacylglycerol Acyltransferases and Triacylglycerol Accumulation in *Mycobacterium tuberculosis* as It Goes into a Dormancy-Like State in Culture", Journal of Bacteriology, Aug. 004, pp. 5017-5030. Aug. 2004.
Daum, et al., Biochemistry, Cell Biology and Molecular Biology of Lipids of *Saccharomyces cerevisiae*, Yeast, 1998, vol. 14, pp. 1471-1510.
Davis, et al., Overproduction of Acetyl-CoA Carboxylase Activity Increases the Rate of Fatty Acid Biosynthesis in Exchcrichia coli, The Journal of Biological Chemistry, vol. 275, No. 37, Sep. 15, 2000, pp. 28593-28598.
Dorne et al., "Do thylakoids really contain phosphatidylcholine?", Proc. Natl. Acad. Sci. USA, vol. 87, Jan. 1990, pp. 71-74.
Han, The *Saccharomyces cerevisiae* Lipin Homolog Is a Mg2+-dependent Phosphatidate Phosphatase Enzyme, The Journal of Biological Chemistry, vol. 281, No. 14, Apr. 7, 2006, pp. 9210-9218.
Harwood, "Recent advances in the biosynthesis of plant fatty acids", Biochimica et Biophysica Acta, vol. 1301, 1996, pp. 7-56.
Hobbs, et al., "Cloning of a cDNA encoding diacylglycerol acyltransferase from *Arabidopsis thaliana* and its functional expression", Federation of European Biochemical Societies, vol. 452, 1999, pp. 145-149.
Hu, et al., "Microalgal triacylglycerols as feedstocks for biofuel production: perspectives and advances", The Plant Journal, vol. 54, 2008, pp. 621-639.
Imashimizu, et al., "Thymine at −5 Is Crucial for cpc Promoter Activity of *Synechocystis* sp. Strain PCC 6714", Journal of Bacteriology, vol. 185, No. 21, Nov. 2003, pp. 6477-6480.
Jiang, et al., "Inhibition of Fatty Acid Synthesis in Excherichia coli in the Absence of Phospholipid Synthesis and Release of Inhibition by Thioesterase Action", Journal of Bacteriology, vol. 176, No. 10, May 1994, pp. 2814-2821.
Kaczmarzyk, et al., "Fatty Acid Activiation in Cyanobacteria Mediated by Acyl-Acyl Carrier Protein Synthetase Enables Fatty Acid Recycling", Plant Physiology, vol. 152, Mar. 2010, pp. 1598-1610.
Kalscheuer, et al., "A Novel Bifunctional Wax Ester Synthase/Acyl-CoA:Diacylglycerol Acyltransferase Mediates Wax Ester adn Triacylglycerol Biosynthesis in *Acinetobacter calcoaceticus* ADP1", The Journal of Biological Chemistry, vol. 278, No. 10, Mar. 7, 2003, pp. 8075-8082.
Kalscheuer, et al., "Analysis of Storage Lipid Accumulation in *Alcanivorax borkumensis*: Evidence for Alternative Triacylglycerol Biosynthesis Routes in Bacteria", Journal of Bacteriology, vol. 189, No. 3, Feb. 2007, pp. 918-928.
Kalscheuer, et al., "Microdiesel: *Escherichia coli* engineered for fuel production", Microbiology, vol. 152, 2006, pp. 2529-2536.
Kalscheuer, et al., Neutral Lipid Biosynthesis in Engineered *Escherichia coli*: Jojoba Oil-Like Wax Esters adn Fatty Acid Butyl Esters, Applied and Environmental Microbiology, vol. 72, No. 2, Feb. 2006, pp. 1373-1379.
Koksharova, et al., "Genetic tools for cyanobacteria", Appl Microbiol Biotechnol, vol. 58, 2002, pp. 123-137.
Liu, et al., "CO2-limitation-inducible Green Recovery of fatty acids from cyanobacterial biomass", PNAS Early Edition, www.pnas.org/cgi/doi/10.1073/pnas.1103016108, Feb. 25, 2011, pp. 1-4.
Liu, et al., "Fatty acid production in genetically modified cyanobacteria", PNAS Early Edition, www.pnas.org/cgi/doi/10.1073/pnas.1103014108, Feb. 25, 2011, pp. 1-6.
Liu et al., "Production and secretion of fatty acids in genetically engineered cyanobacteria", retrieved from www.pnas.org/cgi/doi/10.1073/pnas.1001946107 today, Sep. 12, 2012, 7 pages.
Maeda, et al., cis-Acting Sequences REquired for NtcB-Dependent, Nitrite-Responsive Positive Regulation of the Nitrate Assimilation Operon in the Cyanobacterium *Synechococcus* sp. Strain PCC7942, Journal of Bacteriology, vol. 180, No. 16, Aug. 1998, pp. 4080-4088.
Mermet-Bouvier, et al., "A Conditional Expression Vector for teh Cyanobacteria *Synechocystis* sp. Strains PCC6803 and PCC6714 or *Synechococcus* sp. Strains PCC7942 and PCC6301", Current Microbiology, vol. 28, 1994, pp. 145-148.
Mermet-Bouvier, et al., "Transfer and Replication of RSF1010-Derived Plasmids in Several Cyanobacteria of the Genera *Synechocystis* and *Synechococcus*", Current Microbiology, vol. 27, 1993, pp. 323-327.
Nakamura, et al., "Plastidic Phosphatidic Acid Phosphatases Identified in a Distinct Subfamily of Lipid Phosphate Phosphatases with prokaryotic Origin", The Journal of Biological Chemistry, vol. 282, No. 39, Sep. 28, 2007, pp. 29013-29021.
Nedbal, et al., A Photobioreactor System for Precision Cultivation of Photoautotrophic Microorganisms and for High-Content Analysis of Suspension Dynamics, Biotechnology and Bioengineering, vol. 100, No. 5, Aug. 1, 2008, pp. 902-910.
Nishizuka, "Intracellular Signaling by Hydrolysis of Phospholipids and Activation of Protein Kinase C", Science, vol. 258, Oct. 23, 1992, pp. 607-614.
Office action for U.S. Appl. No. 12/794,536, mailed on Oct. 11, 2011, James Roberts et al., "Modified Photosynthetic Microorganisms for Producing Triglycerides", 16 pages.
Office action for U.S. Appl. No. 12/794,536, mailed on May 31, 2012, James Roberts et al., "Modified Photosynthetic Microorganisms for Producing Triglycerides", 7 pages.
Qi, et al., "Application of the *Synechococcus* nirA Promoter to Establish an Inducible Expression System for Engineering the *Synechocystis* Tocopherol Pathway", Applied and Environmental Microbiology, vol. 71, No. 10, Oct. 2005, pp. 5678-5684.
Qui, et al., "Metabolic engineering of *Aeromonas hydrophila* for the enhanced production of poly(3-hydroxybutyrate-co-3-hydroxyhexanoate)", Appl Microbiol Biotechnol, vol. 69, 2006, pp. 537-542.
Quintana, et al., "Renewable energy from Cyanobacteria: energy p;roduction optimization by metabolic pathway engineering", Appl Microbiol Biotechnol, vol. 91, 2011, pp. 471-490.
Ronen-Tarazi, et al., "The Genomic Region of rbcLS in *Synechococcus* sp. PCC 7942 Contains Genes Involved in the Ability to Grow under Low CO2 Concentration and in Chlorophyll Biosynthesis", Plant Physiol., vol. 108, 1995, pp. 1461-1469.

(56) References Cited

OTHER PUBLICATIONS

Saha, et al., “Cytosolic Triacylglycerol Biosynthetic Pathway in Oilseeds. Molecular Cloning and Expression of Peanut Cytosolic Diacylglycerol Acyltransferase”, Plant Physiology, vol. 141, Aug. 2006, pp. 1533-1543.

Singh, et al., “Bioactive Compounds from Cyanobacteria and Microalgae: An Overview”, Critical Reviews in Biotechnology, vol. 25, 2005, pp. 73-95.

Sorger, et al., “Triacylglycerol biosynthesis in yeast”, Appl Microbiol Biotechnol, vol. 61, 2003, pp. 289-299.

Stoveken, et al., “Bacterial Acyltransferases as an Alternative for Lipase-Catalyzed Acylation for the Production of Oleochemicals and Fuels”, Angew. Chem Int. Ed, vol. 47, 2008, pp. 3688-3694.

Stovoken, et al., “The Wax Ester Synthase/Aceyl Coenzyme A:Diacylglycerol Acyltransferase from *Acinetobacter* sp. Strain ADP1: Characterization of a Novel Type of Acyltransferase”, Journal of Bacteriology, vol. 187, No. 4, Feb. 2005, pp. 1369-1376.

Office Action mailed Sep. 17, 2010, U.S. Appl. No. 12/605,204, filed Oct. 23, 2009.

Van Heeke, et al., “The N-terminal Cysteine of Human Asparagine Synthetase is Essential for Glutamine-dependent Activity”, The Journal of Biological Chemistry, vol. 264, No. 33, Nov. 25, 1989, pp. 19475-19477.

Voelker, et al., “Alteration of the Specificity and REgulation of Fatty Acid Synthesis of Excherichia coli by Expression of a Plant Medium-Chain Acyl-Acyl Carrier Protein Thioesterase”, Journal of Bacteriology, Vo. 176, No. 23, Dec. 1994, pp. 7320-7327.

Waditee, et al., Overexpression of a Na+/H+ antiporter confers salt tolerance on a freshwater cyanobacterium, making it capable of growth in sea water, PNAS, vol. 99, No. 6, Mar. 19, 2002, pp. 4109-4114.

Waltermann, et al., “Key enzymes for biosynthesis of neutral lipid storage comounds in prokaryotes: Propoerties, function and occurrence of wax ester synthases/acyl-CoA:diacylglycerol acyltransferases”, Biochimie 89, 2007, pp. 230-242.

Waltermann, et al., “Mechanism of lipid-body formation in prokaryotes: how bacteria fatten up”, Molecular Microbiology, vol. 55, 2005, pp. 750-763.

Waltermann, et al., “Neutral Lipid Bodies in Prokaryotes: Recent Insights into Structure, Formation, and Relationship to Eukaryotic Lipid Depots”, Journal of Bacteriology, vol. 187, No. 11, Jun. 2005, pp. 3607-3619.

Wirth, et al., “Transformation of various species of gram-negative bacteria belonging to 11 different genera by electroporation”, Mol Gen Genet, vol. 216, 1989, pp. 175-177.

Yen, et al., “DGAT enzymes and triacylglycerol biosynthesis”, Journal of Lipid research, vol. 49, 2008, pp. 2283-2301.

Yu et al., “Production of Eicosapentaenoic Acid by a Recombinant Marine Cyanobacterium, *Synechococcus* sp.”, Lipids, vol. 35, No. 10, 2000, pp. 1061-1064.

Zhang, et al., “Crystal Structure of the Carboxyltransferase Domain of Acetyl-Coenzyme A Carboxylase”, Science, vol. 299, Mar. 28, 2003, pp. 2064-2067.

Zhang, et al., “Molecular effect of FadD on the regulation and metabolism of fatty acid in *Escherichia coli*”, Federation of European Microbiological Societies, vol. 259, May 2006, pp. 249-253.

* cited by examiner

SEQUENCE LISTING

```
<160> NUMBER OF SEQ ID NOS: 30

<210> SEQ ID NO 1
<211> LENGTH: 458
<212> TYPE: PRT
<213> ORGANISM: Acinetobacter baylii sp.

<400> SEQUENCE: 1

Met Arg Pro Leu His Pro Ile Asp Phe Ile Phe Leu Ser Leu Glu Lys
 1               5                  10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
```

```
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455


<210> SEQ ID NO 2
<211> LENGTH: 864
<212> TYPE: PRT
<213> ORGANISM: Saccharomyces cerevisiae

<400> SEQUENCE: 2

Met Glu Phe Gln Tyr Val Gly Arg Ala Leu Gly Ser Val Ser Lys Thr
 1               5                  10                  15

Trp Ser Ser Ile Asn Pro Ala Thr Leu Ser Gly Ala Ile Asp Val Ile
            20                  25                  30

Val Val Glu His Pro Asp Gly Arg Leu Ser Cys Ser Pro Phe His Val
        35                  40                  45

Arg Phe Gly Lys Phe Gln Ile Leu Lys Pro Ser Gln Lys Lys Val Gln
    50                  55                  60

Val Phe Ile Asn Glu Lys Leu Ser Asn Met Pro Met Lys Leu Ser Asp
65                  70                  75                  80

Ser Gly Glu Ala Tyr Phe Val Phe Glu Met Gly Asp Gln Val Thr Asp
                85                  90                  95

Val Pro Asp Glu Leu Leu Val Ser Pro Val Met Ser Ala Thr Ser Ser
            100                 105                 110

Pro Pro Gln Ser Pro Glu Thr Ser Ile Leu Glu Gly Gly Thr Glu Gly
        115                 120                 125

Glu Gly Glu Gly Glu Asn Glu Asn Lys Lys Lys Glu Lys Lys Val Leu
    130                 135                 140

Glu Glu Pro Asp Phe Leu Asp Ile Asn Asp Thr Gly Asp Ser Gly Ser
145                 150                 155                 160

Lys Asn Ser Glu Thr Thr Gly Ser Leu Ser Pro Thr Glu Ser Ser Thr
                165                 170                 175

Thr Thr Pro Pro Asp Ser Val Glu Glu Arg Lys Leu Val Glu Gln Arg
            180                 185                 190
```

```
Thr Lys Asn Phe Gln Gln Lys Leu Asn Lys Lys Leu Thr Glu Ile His
        195                 200                 205

Ile Pro Ser Lys Leu Asp Asn Asn Gly Asp Leu Leu Leu Asp Thr Glu
    210                 215                 220

Gly Tyr Lys Pro Asn Lys Asn Met Met His Asp Thr Asp Ile Gln Leu
225                 230                 235                 240

Lys Gln Leu Leu Lys Asp Glu Phe Gly Asn Asp Ser Asp Ile Ser Ser
                245                 250                 255

Phe Ile Lys Glu Asp Lys Asn Gly Asn Ile Lys Ile Val Asn Pro Tyr
            260                 265                 270

Glu His Leu Thr Asp Leu Ser Pro Pro Gly Thr Pro Pro Thr Met Ala
        275                 280                 285

Thr Ser Gly Ser Val Leu Gly Leu Asp Ala Met Glu Ser Gly Ser Thr
    290                 295                 300

Leu Asn Ser Leu Ser Ser Ser Pro Ser Gly Ser Asp Thr Glu Asp Glu
305                 310                 315                 320

Thr Ser Phe Ser Lys Glu Gln Ser Ser Lys Ser Glu Lys Thr Ser Lys
                325                 330                 335

Lys Gly Thr Ala Gly Ser Gly Glu Thr Glu Lys Arg Tyr Ile Arg Thr
            340                 345                 350

Ile Arg Leu Thr Asn Asp Gln Leu Lys Cys Leu Asn Leu Thr Tyr Gly
        355                 360                 365

Glu Asn Asp Leu Lys Phe Ser Val Asp His Gly Lys Ala Ile Val Thr
    370                 375                 380

Ser Lys Leu Phe Val Trp Arg Trp Asp Val Pro Ile Val Ile Ser Asp
385                 390                 395                 400

Ile Asp Gly Thr Ile Thr Lys Ser Asp Ala Leu Gly His Val Leu Ala
                405                 410                 415

Met Ile Gly Lys Asp Trp Thr His Leu Gly Val Ala Lys Leu Phe Ser
            420                 425                 430

Glu Ile Ser Arg Asn Gly Tyr Asn Ile Leu Tyr Leu Thr Ala Arg Ser
        435                 440                 445

Ala Gly Gln Ala Asp Ser Thr Arg Ser Tyr Leu Arg Ser Ile Glu Gln
    450                 455                 460

Asn Gly Ser Lys Leu Pro Asn Gly Pro Val Ile Leu Ser Pro Asp Arg
465                 470                 475                 480

Thr Met Ala Ala Leu Arg Arg Glu Val Ile Leu Lys Lys Pro Glu Val
                485                 490                 495

Phe Lys Ile Ala Cys Leu Asn Asp Ile Arg Ser Leu Tyr Phe Glu Asp
            500                 505                 510

Ser Asp Asn Glu Val Asp Thr Glu Glu Lys Ser Thr Pro Phe Phe Ala
        515                 520                 525

Gly Phe Gly Asn Arg Ile Thr Asp Ala Leu Ser Tyr Arg Thr Val Gly
    530                 535                 540

Ile Pro Ser Ser Arg Ile Phe Thr Ile Asn Thr Glu Gly Glu Val His
545                 550                 555                 560

Met Glu Leu Leu Glu Leu Ala Gly Tyr Arg Ser Ser Tyr Ile His Ile
                565                 570                 575

Asn Glu Leu Val Asp His Phe Phe Pro Pro Val Ser Leu Asp Ser Val
            580                 585                 590

Asp Leu Arg Thr Asn Thr Ser Met Val Pro Gly Ser Pro Pro Asn Arg
        595                 600                 605

Thr Leu Asp Asn Phe Asp Ser Glu Ile Thr Ser Gly Arg Lys Thr Leu
```

```
    610                 615                 620

Phe Arg Gly Asn Gln Glu Glu Lys Phe Thr Asp Val Asn Phe Trp Arg
625                 630                 635                 640

Asp Pro Leu Val Asp Ile Asp Asn Leu Ser Asp Ile Ser Asn Asp Asp
                645                 650                 655

Ser Asp Asn Ile Asp Glu Asp Thr Asp Val Ser Gln Gln Ser Asn Ile
            660                 665                 670

Ser Arg Asn Arg Ala Asn Ser Val Lys Thr Ala Lys Val Thr Lys Ala
        675                 680                 685

Pro Gln Arg Asn Val Ser Gly Ser Thr Asn Asn Asn Glu Val Leu Ala
    690                 695                 700

Ala Ser Ser Asp Val Glu Asn Ala Ser Asp Leu Val Ser Ser His Ser
705                 710                 715                 720

Ser Ser Gly Ser Thr Pro Asn Lys Ser Thr Met Ser Lys Gly Asp Ile
                725                 730                 735

Gly Lys Gln Ile Tyr Leu Glu Leu Gly Ser Pro Leu Ala Ser Pro Lys
            740                 745                 750

Leu Arg Tyr Leu Asp Asp Met Asp Asp Glu Asp Ser Asn Tyr Asn Arg
        755                 760                 765

Thr Lys Ser Arg Arg Ala Ser Ser Ala Ala Ala Thr Ser Ile Asp Lys
    770                 775                 780

Glu Phe Lys Lys Leu Ser Val Ser Lys Ala Gly Ala Pro Thr Arg Ile
785                 790                 795                 800

Val Ser Lys Ile Asn Val Ser Asn Asp Val His Ser Leu Gly Asn Ser
                805                 810                 815

Asp Thr Glu Ser Arg Arg Glu Gln Ser Val Asn Glu Thr Gly Arg Asn
            820                 825                 830

Gln Leu Pro His Asn Ser Met Asp Asp Lys Asp Leu Asp Ser Arg Val
        835                 840                 845

Ser Asp Glu Phe Asp Asp Asp Glu Phe Asp Glu Asp Glu Phe Glu Asp
    850                 855                 860


<210> SEQ ID NO 3
<211> LENGTH: 2235
<212> TYPE: PRT
<213> ORGANISM: Saccharomyces cerevisiae

<400> SEQUENCE: 3

Met Glu Phe Ser Glu Glu Ser Leu Phe Glu Ser Ser Pro Gln Lys Met
 1               5                  10                  15

Glu Tyr Glu Ile Thr Asn Tyr Ser Glu Arg His Thr Glu Leu Pro Gly
            20                  25                  30

His Phe Ile Gly Leu Asn Thr Val Asp Lys Leu Glu Glu Ser Pro Leu
        35                  40                  45

Arg Asp Phe Val Lys Ser His Gly Gly His Thr Val Ile Ser Lys Ile
    50                  55                  60

Leu Ile Ala Asn Asn Gly Ile Ala Ala Val Lys Glu Ile Arg Ser Val
65                  70                  75                  80

Arg Lys Trp Ala Tyr Glu Thr Phe Gly Asp Asp Arg Thr Val Gln Phe
                85                  90                  95

Val Ala Met Ala Thr Pro Glu Asp Leu Glu Ala Asn Ala Glu Tyr Ile
            100                 105                 110

Arg Met Ala Asp Gln Tyr Ile Glu Val Pro Gly Gly Thr Asn Asn Asn
        115                 120                 125
```

```
Asn Tyr Ala Asn Val Asp Leu Ile Val Asp Ile Ala Glu Arg Ala Asp
    130                 135                 140

Val Asp Ala Val Trp Ala Gly Trp Gly His Ala Ser Glu Asn Pro Leu
145                 150                 155                 160

Leu Pro Glu Lys Leu Ser Gln Ser Lys Arg Lys Val Ile Phe Ile Gly
                165                 170                 175

Pro Pro Gly Asn Ala Met Arg Ser Leu Gly Asp Lys Ile Ser Ser Thr
            180                 185                 190

Ile Val Ala Gln Ser Ala Lys Val Pro Cys Ile Pro Trp Ser Gly Thr
        195                 200                 205

Gly Val Asp Thr Val His Val Asp Glu Lys Thr Gly Leu Val Ser Val
    210                 215                 220

Asp Asp Asp Ile Tyr Gln Lys Gly Cys Cys Thr Ser Pro Glu Asp Gly
225                 230                 235                 240

Leu Gln Lys Ala Lys Arg Ile Gly Phe Pro Val Met Ile Lys Ala Ser
                245                 250                 255

Glu Gly Gly Gly Gly Lys Gly Ile Arg Gln Val Glu Arg Glu Glu Asp
            260                 265                 270

Phe Ile Ala Leu Tyr His Gln Ala Ala Asn Glu Ile Pro Gly Ser Pro
        275                 280                 285

Ile Phe Ile Met Lys Leu Ala Gly Arg Ala Arg His Leu Glu Val Gln
    290                 295                 300

Leu Leu Ala Asp Gln Tyr Gly Thr Asn Ile Ser Leu Phe Gly Arg Asp
305                 310                 315                 320

Cys Ser Val Gln Arg Arg His Gln Lys Ile Ile Glu Glu Ala Pro Val
                325                 330                 335

Thr Ile Ala Lys Ala Glu Thr Phe His Glu Met Glu Lys Ala Ala Val
            340                 345                 350

Arg Leu Gly Lys Leu Val Gly Tyr Val Ser Ala Gly Thr Val Glu Tyr
        355                 360                 365

Leu Tyr Ser His Asp Asp Gly Lys Phe Tyr Phe Leu Glu Leu Asn Pro
    370                 375                 380

Arg Leu Gln Val Glu His Pro Thr Thr Glu Met Val Ser Gly Val Asn
385                 390                 395                 400

Leu Pro Ala Ala Gln Leu Gln Ile Ala Met Gly Ile Pro Met His Arg
                405                 410                 415

Ile Ser Asp Ile Arg Thr Leu Tyr Gly Met Asn Pro His Ser Ala Ser
            420                 425                 430

Glu Ile Asp Phe Glu Phe Lys Thr Gln Asp Ala Thr Lys Lys Gln Arg
        435                 440                 445

Arg Pro Ile Pro Lys Gly His Cys Thr Ala Cys Arg Ile Thr Ser Glu
    450                 455                 460

Asp Pro Asn Asp Gly Phe Lys Pro Ser Gly Gly Thr Leu His Glu Leu
465                 470                 475                 480

Asn Phe Arg Ser Ser Ser Asn Val Trp Gly Tyr Phe Ser Val Gly Asn
                485                 490                 495

Asn Gly Asn Ile His Ser Phe Ser Asp Ser Gln Phe Gly His Ile Phe
            500                 505                 510

Ala Phe Gly Glu Asn Arg Gln Ala Ser Arg Lys His Met Val Val Ala
        515                 520                 525

Leu Lys Glu Leu Ser Ile Arg Gly Asp Phe Arg Thr Thr Val Glu Tyr
    530                 535                 540

Leu Ile Lys Leu Leu Glu Thr Glu Asp Phe Glu Asp Asn Thr Ile Thr
```

```
545                 550                 555                 560

Thr Gly Trp Leu Asp Asp Leu Ile Thr His Lys Met Thr Ala Glu Lys
                565                 570                 575

Pro Asp Pro Thr Leu Ala Val Ile Cys Gly Ala Ala Thr Lys Ala Phe
            580                 585                 590

Leu Ala Ser Glu Glu Ala Arg His Lys Tyr Ile Glu Ser Leu Gln Lys
        595                 600                 605

Gly Gln Val Leu Ser Lys Asp Leu Leu Gln Thr Met Phe Pro Val Asp
    610                 615                 620

Phe Ile His Glu Gly Lys Arg Tyr Lys Phe Thr Val Ala Lys Ser Gly
625                 630                 635                 640

Asn Asp Arg Tyr Thr Leu Phe Ile Asn Gly Ser Lys Cys Asp Ile Ile
                645                 650                 655

Leu Arg Gln Leu Ser Asp Gly Gly Leu Leu Ile Ala Ile Gly Gly Lys
            660                 665                 670

Ser His Thr Ile Tyr Trp Lys Glu Glu Val Ala Ala Thr Arg Leu Ser
        675                 680                 685

Val Asp Ser Met Thr Thr Leu Leu Glu Val Glu Asn Asp Pro Thr Gln
    690                 695                 700

Leu Arg Thr Pro Ser Pro Gly Lys Leu Val Lys Phe Leu Val Glu Asn
705                 710                 715                 720

Gly Glu His Ile Ile Lys Gly Gln Pro Tyr Ala Glu Ile Glu Val Met
                725                 730                 735

Lys Met Gln Met Pro Leu Val Ser Gln Glu Asn Gly Ile Val Gln Leu
            740                 745                 750

Leu Lys Gln Pro Gly Ser Thr Ile Val Ala Gly Asp Ile Met Ala Ile
        755                 760                 765

Met Thr Leu Asp Asp Pro Ser Lys Val Lys His Ala Leu Pro Phe Glu
    770                 775                 780

Gly Met Leu Pro Asp Phe Gly Ser Pro Val Ile Glu Gly Thr Lys Pro
785                 790                 795                 800

Ala Tyr Lys Phe Lys Ser Leu Val Ser Thr Leu Glu Asn Ile Leu Lys
                805                 810                 815

Gly Tyr Asp Asn Gln Val Ile Met Asn Ala Ser Leu Gln Gln Leu Ile
            820                 825                 830

Glu Val Leu Arg Asn Pro Lys Leu Pro Tyr Ser Glu Trp Lys Leu His
        835                 840                 845

Ile Ser Ala Leu His Ser Arg Leu Pro Ala Lys Leu Asp Glu Gln Met
    850                 855                 860

Glu Glu Leu Val Ala Arg Ser Leu Arg Arg Gly Ala Val Phe Pro Ala
865                 870                 875                 880

Arg Gln Leu Ser Lys Leu Ile Asp Met Ala Val Lys Asn Pro Glu Tyr
                885                 890                 895

Asn Pro Asp Lys Leu Leu Gly Ala Val Val Glu Pro Leu Ala Asp Ile
            900                 905                 910

Ala His Lys Tyr Ser Asn Gly Leu Glu Ala His Glu His Ser Ile Phe
        915                 920                 925

Val His Phe Leu Glu Glu Tyr Tyr Glu Val Glu Lys Leu Phe Asn Gly
    930                 935                 940

Pro Asn Val Arg Glu Glu Asn Ile Ile Leu Lys Leu Arg Asp Glu Asn
945                 950                 955                 960

Pro Lys Asp Leu Asp Lys Val Ala Leu Thr Val Leu Ser His Ser Lys
                965                 970                 975
```

```
Val Ser Ala Lys Asn Asn Leu Ile Leu Ala Ile Leu Lys His Tyr Gln
            980                 985                 990

Pro Leu Cys Lys Leu Ser Ser Lys Val Ser Ala Ile Phe Ser Thr Pro
        995                 1000                1005

Leu Gln His Ile Val Glu Leu Glu Ser Lys Ala Thr Ala Lys Val Ala
    1010                1015                1020

Leu Gln Ala Arg Glu Ile Leu Ile Gln Gly Ala Leu Pro Ser Val Lys
1025                1030                1035                1040

Glu Arg Thr Glu Gln Ile Glu His Ile Leu Lys Ser Ser Val Val Lys
                1045                1050                1055

Val Ala Tyr Gly Ser Ser Asn Pro Lys Arg Ser Glu Pro Asp Leu Asn
            1060                1065                1070

Ile Leu Lys Asp Leu Ile Asp Ser Asn Tyr Val Val Phe Asp Val Leu
        1075                1080                1085

Leu Gln Phe Leu Thr His Gln Asp Pro Val Val Thr Ala Ala Ala Ala
    1090                1095                1100

Gln Val Tyr Ile Arg Arg Ala Tyr Arg Ala Tyr Thr Ile Gly Asp Ile
1105                1110                1115                1120

Arg Val His Glu Gly Val Thr Val Pro Ile Val Glu Trp Lys Phe Gln
                1125                1130                1135

Leu Pro Ser Ala Ala Phe Ser Thr Phe Pro Thr Val Lys Ser Lys Met
            1140                1145                1150

Gly Met Asn Arg Ala Val Ser Val Ser Asp Leu Ser Tyr Val Ala Asn
        1155                1160                1165

Ser Gln Ser Ser Pro Leu Arg Glu Gly Ile Leu Met Ala Val Asp His
    1170                1175                1180

Leu Asp Asp Val Asp Glu Ile Leu Ser Gln Ser Leu Glu Val Ile Pro
1185                1190                1195                1200

Arg His Gln Ser Ser Ser Asn Gly Pro Ala Pro Asp Arg Ser Gly Ser
                1205                1210                1215

Ser Ala Ser Leu Ser Asn Val Ala Asn Val Cys Val Ala Ser Thr Glu
            1220                1225                1230

Gly Phe Glu Ser Glu Glu Glu Ile Leu Val Arg Leu Arg Glu Ile Leu
        1235                1240                1245

Asp Leu Asn Lys Gln Glu Leu Ile Asn Ala Ser Ile Arg Arg Ile Thr
    1250                1255                1260

Phe Met Phe Gly Phe Lys Asp Gly Ser Tyr Pro Lys Tyr Tyr Thr Phe
1265                1270                1275                1280

Asn Gly Pro Asn Tyr Asn Glu Asn Glu Thr Ile Arg His Ile Glu Pro
                1285                1290                1295

Ala Leu Ala Phe Gln Leu Glu Leu Gly Arg Leu Ser Asn Phe Asn Ile
            1300                1305                1310

Lys Pro Ile Phe Thr Asp Asn Arg Asn Ile His Val Tyr Glu Ala Val
        1315                1320                1325

Ser Lys Thr Ser Pro Leu Asp Lys Arg Phe Phe Thr Arg Gly Ile Ile
    1330                1335                1340

Arg Thr Gly His Ile Arg Asp Asp Ile Ser Ile Gln Glu Tyr Leu Thr
1345                1350                1355                1360

Ser Glu Ala Asn Arg Leu Met Ser Asp Ile Leu Asp Asn Leu Glu Val
                1365                1370                1375

Thr Asp Thr Ser Asn Ser Asp Leu Asn His Ile Phe Ile Asn Phe Ile
            1380                1385                1390
```

-continued

```
Ala Val Phe Asp Ile Ser Pro Glu Asp Val Glu Ala Ala Phe Gly Gly
        1395                1400                1405

Phe Leu Glu Arg Phe Gly Lys Arg Leu Leu Arg Leu Arg Val Ser Ser
    1410                1415                1420

Ala Glu Ile Arg Ile Ile Ile Lys Asp Pro Gln Thr Gly Ala Pro Val
1425                1430                1435                1440

Pro Leu Arg Ala Leu Ile Asn Asn Val Ser Gly Tyr Val Ile Lys Thr
                1445                1450                1455

Glu Met Tyr Thr Glu Val Lys Asn Ala Lys Gly Glu Trp Val Phe Lys
            1460                1465                1470

Ser Leu Gly Lys Pro Gly Ser Met His Leu Arg Pro Ile Ala Thr Pro
        1475                1480                1485

Tyr Pro Val Lys Glu Trp Leu Gln Pro Lys Arg Tyr Lys Ala His Leu
    1490                1495                1500

Met Gly Thr Thr Tyr Val Tyr Asp Phe Pro Glu Leu Phe Arg Gln Ala
1505                1510                1515                1520

Ser Ser Ser Gln Trp Lys Asn Phe Ser Ala Asp Val Lys Leu Thr Asp
                1525                1530                1535

Asp Phe Phe Ile Ser Asn Glu Leu Ile Glu Asp Glu Asn Gly Glu Leu
            1540                1545                1550

Thr Glu Val Glu Arg Glu Pro Gly Ala Asn Ala Ile Gly Met Val Ala
        1555                1560                1565

Phe Lys Ile Thr Val Lys Thr Pro Glu Tyr Pro Arg Gly Arg Gln Phe
    1570                1575                1580

Val Val Val Ala Asn Asp Ile Thr Phe Lys Ile Gly Ser Phe Gly Pro
1585                1590                1595                1600

Gln Glu Asp Glu Phe Phe Asn Lys Val Thr Glu Tyr Ala Arg Lys Arg
                1605                1610                1615

Gly Ile Pro Arg Ile Tyr Leu Ala Ala Asn Ser Gly Ala Arg Ile Gly
            1620                1625                1630

Met Ala Glu Glu Ile Val Pro Leu Phe Gln Val Ala Trp Asn Asp Ala
        1635                1640                1645

Ala Asn Pro Asp Lys Gly Phe Gln Tyr Leu Tyr Leu Thr Ser Glu Gly
    1650                1655                1660

Met Glu Thr Leu Lys Lys Phe Asp Lys Glu Asn Ser Val Leu Thr Glu
1665                1670                1675                1680

Arg Thr Val Ile Asn Gly Glu Glu Arg Phe Val Ile Lys Thr Ile Ile
                1685                1690                1695

Gly Ser Glu Asp Gly Leu Gly Val Glu Cys Leu Arg Gly Ser Gly Leu
            1700                1705                1710

Ile Ala Gly Ala Thr Ser Arg Ala Tyr His Asp Ile Phe Thr Ile Thr
        1715                1720                1725

Leu Val Thr Cys Arg Ser Val Gly Ile Gly Ala Tyr Leu Val Arg Leu
    1730                1735                1740

Gly Gln Arg Ala Ile Gln Val Glu Gly Gln Pro Ile Ile Leu Thr Gly
1745                1750                1755                1760

Ala Pro Ala Ile Asn Lys Met Leu Gly Arg Glu Val Tyr Thr Ser Asn
                1765                1770                1775

Leu Gln Leu Gly Gly Thr Gln Ile Met Tyr Asn Asn Gly Val Ser His
            1780                1785                1790

Leu Thr Ala Val Asp Asp Leu Ala Gly Val Glu Lys Ile Val Glu Trp
        1795                1800                1805

Met Ser Tyr Val Pro Ala Lys Arg Asn Met Pro Val Pro Ile Leu Glu
```

```
    1810                1815                1820

Thr Lys Asp Thr Trp Asp Arg Pro Val Asp Phe Thr Pro Thr Asn Asp
1825                1830                1835                1840

Glu Thr Tyr Asp Val Arg Trp Met Ile Glu Gly Arg Glu Thr Glu Ser
                1845                1850                1855

Gly Phe Glu Tyr Gly Leu Phe Asp Lys Gly Ser Phe Phe Glu Thr Leu
            1860                1865                1870

Ser Gly Trp Ala Lys Gly Val Val Val Gly Arg Ala Arg Leu Gly Gly
        1875                1880                1885

Ile Pro Leu Gly Val Ile Gly Val Glu Thr Arg Thr Val Glu Asn Leu
    1890                1895                1900

Ile Pro Ala Asp Pro Ala Asn Pro Asn Ser Ala Glu Thr Leu Ile Gln
1905                1910                1915                1920

Glu Pro Gly Gln Val Trp His Pro Asn Ser Ala Phe Lys Thr Ala Gln
                1925                1930                1935

Ala Ile Asn Asp Phe Asn Asn Gly Glu Gln Leu Pro Met Met Ile Leu
            1940                1945                1950

Ala Asn Trp Arg Gly Phe Ser Gly Gly Gln Arg Asp Met Phe Asn Glu
        1955                1960                1965

Val Leu Lys Tyr Gly Ser Phe Ile Val Asp Ala Leu Val Asp Tyr Lys
    1970                1975                1980

Gln Pro Ile Ile Ile Tyr Ile Pro Pro Thr Gly Glu Leu Arg Gly Gly
1985                1990                1995                2000

Ser Trp Val Val Val Asp Pro Thr Ile Asn Ala Asp Gln Met Glu Met
                2005                2010                2015

Tyr Ala Asp Val Asn Ala Arg Ala Gly Val Leu Glu Pro Gln Gly Met
            2020                2025                2030

Val Gly Ile Lys Phe Arg Arg Glu Lys Leu Leu Asp Thr Met Asn Arg
        2035                2040                2045

Leu Asp Asp Lys Tyr Arg Glu Leu Arg Ser Gln Leu Ser Asn Lys Ser
    2050                2055                2060

Leu Ala Pro Glu Val His Gln Gln Ile Ser Lys Gln Leu Ala Asp Arg
2065                2070                2075                2080

Glu Arg Glu Leu Leu Pro Ile Tyr Gly Gln Ile Ser Leu Gln Phe Ala
                2085                2090                2095

Asp Leu His Asp Arg Ser Ser Arg Met Val Ala Lys Gly Val Ile Ser
            2100                2105                2110

Lys Glu Leu Glu Trp Thr Glu Ala Arg Arg Phe Phe Phe Trp Arg Leu
        2115                2120                2125

Arg Arg Arg Leu Asn Glu Glu Tyr Leu Ile Lys Arg Leu Ser His Gln
    2130                2135                2140

Val Gly Glu Ala Ser Arg Leu Glu Lys Ile Ala Arg Ile Arg Ser Trp
2145                2150                2155                2160

Tyr Pro Ala Ser Val Asp His Glu Asp Asp Arg Gln Val Ala Thr Trp
                2165                2170                2175

Ile Glu Glu Asn Tyr Lys Thr Leu Asp Asp Lys Leu Lys Gly Leu Lys
            2180                2185                2190

Leu Glu Ser Phe Ala Gln Asp Leu Ala Lys Lys Ile Arg Ser Asp His
        2195                2200                2205

Asp Asn Ala Ile Asp Gly Leu Ser Glu Val Ile Lys Met Leu Ser Thr
    2210                2215                2220

Asp Asp Lys Glu Lys Leu Leu Lys Thr Leu Lys
2225                2230                2235
```

```
<210> SEQ ID NO 4
<211> LENGTH: 1377
<212> TYPE: DNA
<213> ORGANISM: Artificial Sequence
<220> FEATURE:
<223> OTHER INFORMATION: Codon-optimized Acinetobacter baylii sp. atfA

<400> SEQUENCE: 4

atgcggccct tgcaccccat tgacttcatc tttctgagtt tggagaaacg gcaacagccc     60

atgcatgtcg gtggcttgtt tctcttccaa atccccgata acgccccgga cacctttatt    120

caggatctgg tcaatgatat ccggatctcg aaatcgatcc ccgtgccgcc gtttaataat    180

aaactgaacg gcctcttttg ggacgaagac gaggaatttg atctggatca ccattttcgg    240

cacatcgctt tgccccaccc gggtcggatt cgcgaactcc tgatctatat tagccaagaa    300

cacagcacgt tgttggaccg ggccaaaccg ctctggacgt gcaatatcat cgaaggcatc    360

gaaggcaacc gctttgcgat gtacttcaag attcatcacg cgatggttga cggtgtcgct    420

ggcatgcgcc tgatcgaaaa atcgctgagc catgatgtga ccgaaaagag tatcgtcccc    480

ccctggtgcg tggaaggtaa gcgcgccaag cgcctccgcg aaccgaaaac gggcaagatt    540

aagaaaatca tgagcggtat caagtcgcag ctgcaggcta ccccgaccgt gatccaggag    600

ctgtcgcaaa ccgtgtttaa ggatattggt cggaacccgg atcatgtcag tagtttccaa    660

gctccctgtt cgatcttgaa tcagcgcgtt agcagcagcc gccggttcgc tgctcaaagt    720

tttgatctcg atcggtttcg gaatattgcc aagtcgctga acgtcaccat caatgatgtg    780

gttctcgcgg tttgttcggg tgccctccgc gcgtatctga tgagccataa cagtctcccc    840

agtaagccgc tgattgctat ggttcccgcg tcgattcgga atgacgacag cgatgtgagc    900

aaccggatta ccatgatcct ggctaacctc gcgacccaca aagatgatcc gttgcaacgc    960

ctggagatta tccgccgcag tgtgcagaac agtaaacagc gcttcaaacg gatgaccagt   1020

gatcaaattc tgaattacag cgctgtggtc tatggtcccg ccggcttgaa tattatcagt   1080

ggtatgatgc ccaaacgcca agcgtttaac ttggtgatca gtaatgtgcc gggtccgcgc   1140

gaacccttgt attggaacgg tgctaaactc gatgccctct accccgccag tatcgtgctc   1200

gatggccagg ctctcaatat taccatgacc agctatctcg ataaactcga ggtgggtttg   1260

attgcgtgcc gcaacgcgct gccccgcatg cagaacttgc tgacccacct ggaagaggaa   1320

atccagctct tcgagggcgt gattgcgaag caggaagata ttaaaacggc caactag      1377

<210> SEQ ID NO 5
<211> LENGTH: 2595
<212> TYPE: DNA
<213> ORGANISM: Artificial Sequence
<220> FEATURE:
<223> OTHER INFORMATION: Codon-optimized S. cerevisiae phosphatidate
      phosphatase (PAH1)

<400> SEQUENCE: 5

atggaattcc aatatgttgg tcgggctttg ggtagtgtta gtaaaacgtg gtcgagtatc     60

aaccccgcca ccctgagcgg cgctatcgat gtcattgtcg tggaacaccc cgatggccgg    120

ctcagttgta gcccccttcca tgtgcgcttt ggtaaattcc agattctgaa acccagccaa    180

aagaaagtcc aggtctttat taacgagaaa ctgtcgaata tgcccatgaa actctcggat    240

agcggcgagg cgtacttcgt ttttgagatg ggtgatcaag tgacggatgt cccggatgaa    300

ctgctcgtct cgccggtcat gagtgccacg agtagtccgc cccaatcgcc ggaaacctcg    360
```

```
attctcgaag gcggtaccga aggcgagggc gaaggtgaga atgaaaataa gaaaaaggaa    420

aagaaggtgt tggaggagcc cgactttctg gacattaatg acaccggtga cagcggcagc    480

aagaacagtg agacgacggg ttcgctctcg ccgaccgaaa gtagtacgac gacgccgccc    540

gatagcgtcg aggaacgcaa gttggtcgaa caacggacca agaattttca gcaaaagctg    600

aataagaaac tgaccgaaat ccatattccg agcaaattgg acaataacgg tgatttgctc    660

ctggacaccg agggttataa gccgaataaa aacatgatgc acgacacgga tattcagctg    720

aagcaattgc tcaaggatga gttcggtaac gatagcgata tttcgagctt catcaaagaa    780

gacaagaatg gcaacattaa aatcgtgaac ccctatgagc atttgaccga tttgagtccc    840

ccgggtacgc cccgaccat ggccacgagt ggcagtgtcc tgggcttgga tgcgatggag    900

agtggttcga cgctgaacag cttgagcagc agcccgagcg gcagtgacac cgaggatgag    960

acgagcttta gcaaggaaca gtcgtcgaag agtgaaaaaa cgtcgaagaa aggcaccgcg   1020

ggttcgggtg aaacggagaa acgctacatc cgcacgatcc ggctcacgaa tgatcagctg   1080

aaatgcctca acttgacgta cggtgaaaat gacttgaaat ttagtgttga ccatggcaaa   1140

gccattgtga ccagcaaatt gtttgtctgg cgctgggacg tccccatcgt tatcagcgac   1200

attgacggta cgattacgaa aagtgatgcg ctgggccacg tcctcgccat gatcggcaaa   1260

gattggaccc atctcggcgt cgctaagctg ttcagtgaga tctcgcgcaa cggttacaat   1320

atcctgtacc tgaccgcgcg ctcggccggt caggctgaca gtacccgctc gtatctccgc   1380

agtattgagc agaacggtag caagctcccg aacggccccg tcattctgag ccccgatcgg   1440

accatggctg ccctgcgccg ggaggtgatt ctgaaaaagc ccgaagtctt taaaatcgct   1500

tgcttgaacg atatccgctc gctctatttc gaagactcgg ataacgaagt ggacacggag   1560

gaaaagagca cgccgttttt cgcgggcttt ggcaatcgga tcaccgatgc gctcagctat   1620

cggacggtcg gcatcccgag tagccgcatc ttcacgatta acacggaagg cgaggtgcac   1680

atggagctgc tcgagctcgc cggttaccgg agtagctata tccatatcaa cgaactggtc   1740

gatcacttct tcccgccggt gagcctggac tcggtcgatc tgcgcacgaa cacgagcatg   1800

gtcccgggca gcccgccgaa ccgcaccctg gataactttg atagcgaaat caccagtggc   1860

cgcaagacgt tgtttcgcgg taatcaggag gaaaaattca cggacgtcaa cttttggcgc   1920

gatccgttgg tggacatcga caacctctcg gatatcagta acgatgattc ggacaatatt   1980

gatgaagaca ccgatgtgag ccaacagtcg aacatcagcc gcaaccgcgc taactcggtc   2040

aagacggcca aggtgaccaa ggctccgcag cggaatgtgt cgggcagtac gaataacaat   2100

gaagttctgg ctgcgagtag tgatgttgaa aatgccagtg acttggttag cagccactcg   2160

agtagcggct cgacccccaa caagtcgacg atgagtaagg gtgatatcgg caaacaaatc   2220

tatctggaac tgggctcgcc cttggcgagt cccaaactcc ggtatctgga cgatatggat   2280

gatgaggact cgaactataa tcgcaccaag agccgccggg ctagtagcgc cgctgctacc   2340

agcatcgaca aggagtttaa aaagctcagt gtgagtaaag ctggcgctcc cacccgcatc   2400

gttagcaaga tcaacgtgtc gaatgatgtg cacagtttgg gcaacagtga taccgaaagc   2460

cggcgggaac agagcgtcaa tgaaaccggt cgcaatcagt tgccgcacaa tagtatggat   2520

gataaggatt tggattcgcg ggtgagtgac gagttcgatg acgatgagtt tgatgaagat   2580

gagtttgagg attag                                                    2595
```

<210> SEQ ID NO 6

<211> LENGTH: 6708
<212> TYPE: DNA
<213> ORGANISM: Artificial Sequence
<220> FEATURE:
<223> OTHER INFORMATION: Codon-optimized S. cerevisiae acetyl Coa carboxylase (ACC1)

<400> SEQUENCE: 6

```
atggaattct ccgaggaaag tttgttcgaa agcagtccgc agaaaatgga atatgaaatt     60
acgaattatt cggaacgcca cacggagctc cccgggcact tcatcggact caacaccgtg    120
gataagctcg aagaaagtcc cctccgcgat tttgtgaaaa gccacggcgg ccataccgtg    180
atctcgaaga ttctgattgc caataacgga attgccgctg tcaaggagat ccgcagcgtc    240
cggaagtggg cgtacgaaac ttttggcgat gaccgtacag tccagtttgt tgctatggcg    300
actccggaag acttggaggc gaatgcggaa tacattcgaa tggccgatca atacatcgaa    360
gtccccggag gaacgaacaa caacaattat gcgaacgtcg atttgatcgt ggatatcgca    420
gaacgcgcgg acgtggatgc tgtttgggcc ggatggggcc acgcttcgga aaaccctctg    480
ttgccggaaa aactcagcca gtctaaacgg aaagtcattt tcatcggccc tccgggcaac    540
gcaatgcgct cgttgggtga taagatcagc tcgaccattg tggctcagag cgctaaagtc    600
ccatgtattc cctggtcggg taccggcgtg gatacggtcc atgttgatga gaaaactgga    660
ctggtcagcg tcgatgatga tatctaccaa aagggctgtt gcaccagccc ggaagatggc    720
ctgcaaaagg cgaagcgcat cgggttccca gtcatgatca aggcatccga aggcggaggc    780
ggtaagggta tccgccaggt tgagcgtgaa gaagatttta tcgcactgta tcatcaagcg    840
gctaacgaaa tcccgggctc gccaattttc attatgaaac tggctggtcg ggcgcgtcat    900
ctcgaagtgc aactcctcgc tgaccagtac ggtacgaaca tctctttgtt cggtcgggat    960
tgttcggtcc agcgtcgtca ccagaagatc attgaagaag cccctgttac catcgcaaag   1020
gccgagacgt ttcatgagat ggagaaagcg gccgtccgcc tcggcaagct ggtcggttac   1080
gttagcgcag gcaccgtgga atacctctat tcccacgacg atggtaagtt ttactttctc   1140
gaactgaatc ctcgcctgca ggttgaacac ccgaccacag agatggtgtc gggggtcaat   1200
ctgccggctg cgcagttgca gattgcaatg ggcattccga tgcatcgaat cagcgacatc   1260
cgaaccctgt acggcatgaa cccgcacagt gcgagcgaaa tcgactttga gttcaagacc   1320
caagacgcca cgaagaaaca gcgacgccca attccgaagg gccattgcac cgcgtgtcgc   1380
attacctcgg aggaccccaa tgatggtttt aagccctcgg gcggtactct gcacgagctc   1440
aacttccgct cctcctcgaa cgtctggggc tatttcagcg tcggaaataa tggtaacatt   1500
catagttttt ccgattccca atttggccat atcttcgcct ttggcgaaaa ccgacaagct   1560
agccgcaaac acatggtcgt ggcgttgaag gagctgagta tccgagggga ctttcgcacg   1620
acggtggaat atctgatcaa actgctcgaa acggaggact ttgaggataa cacaattacc   1680
accggatggt tggacgacct gattacgcac aaaatgaccg ccgagaaacc cgaccccacc   1740
ttggcagtga tttgtggcgc ggcaacgaag gccttttttgg cctctgaaga ggcacgccac   1800
aagtacattg agagtctcca aaagggtcag gtgctgagta aagatctgct gcaaaccatg   1860
tttcctgtcg actttattca tgaggggaaa cgctacaaat tcacggttgc taagtctggt   1920
aatgatcggt acacattgtt tatcaatgga tcgaagtgcg atattatctt gcgacaactc   1980
tccgacggcg gcctcctgat tgctatcggc gggaaaagtc ataccatcta ttggaaagaa   2040
gaggtcgccg ccacccgact gagcgttgat tcgatgacta ctctgctcga agttgaaaac   2100
```

```
gatccaacgc aactgcgcac tccctctccg ggtaagctcg tgaagtttct cgtcgagaat   2160
ggcgaacaca ttattaaggg ccagccgtat gcggaaatcg aggtgatgaa gatgcagatg   2220
cccctggtca gccaagagaa cggtattgtg caactgctga aacagcccgg cagcaccatc   2280
gtcgctggcg atatcatggc tatcatgacc ctcgatgatc cttccaaagt caaacatgcc   2340
ctgcccttcg aaggcatgct ccccgatttt ggctccccccg tgattgaggg caccaaacca   2400
gcttacaagt ttaaatcgct ggtttccacc ctcgagaaca tcttgaaggg ctacgataat   2460
caggtcatta tgaatgccag cctccagcag ctcattgagg tcctccgtaa ccccaagctg   2520
ccctacagtg aatggaagct ccacatcagt gcgctccact cgcgactgcc cgcgaagctc   2580
gatgagcaga tggaagagct cgtcgctcgc agcctgcgtc gcggcgcagt ctttccggca   2640
cggcaactgt cgaagctcat cgatatggct gtcaaaaacc ccgaatacaa ccccgataaa   2700
ctcttgggtg ctgtcgttga gccgctcgcc gatatcgcgc acaagtacag taatggcctg   2760
gaggcgcacg aacacagtat ctttgttcac ttcctggaag aatactatga ggttgagaaa   2820
ctgttcaatg ggcctaatgt ccgggaagag aatattatcc tgaagctccg tgatgaaaat   2880
ccgaaagatt tggataaagt cgccttgacg gtgctcagtc atagcaaggt gagtgccaag   2940
aacaatctca tcctggcgat cttgaaacac taccaacctt tgtgcaagct gagttccaag   3000
gtgtcggcta tttttagtac gcccctgcag cacatcgtgg aactcgaaag taaagccacc   3060
gccaaggtgg ctctgcaggc ccgggagatt ctgatccagg gtgctctgcc gagcgtgaaa   3120
gagcggacgg aacaaatcga acacatcctg aagagttcgg tcgtgaaggt tgcatatggc   3180
agcagtaacc ctaaacgctc ggaaccggac ctcaatatcc tgaaggatct gatcgatagt   3240
aattatgttg tttttgatgt cctgctccaa tttctgactc accaagatcc ggttgttact   3300
gcggctgccg cgcaagttta cattcgacgc gcctatcgcg cctacacaat cggcgatatt   3360
cgagtccatg agggcgtgac cgttccaatc gttgaatgga aattccagtt gccatcggcg   3420
gctttttcta cattcccaac agtcaagagt aagatgggca tgaatcgtgc cgtttcggtc   3480
agtgatttgt cctatgtcgc aaactcgcaa tctagtcctc tgcgagaggg catcctgatg   3540
gcagtggatc atttggatga tgtcgatgag atcctctcgc aaagtctcga ggtcattcct   3600
cgccaccaat cgtcgtccaa tggcccagct cccgatcgat ccggttcttc cgccagcttg   3660
tcgaatgtcg ccaacgtctg tgtggcgtcg actgaggggt tcgaaagcga agaagaaatt   3720
ttggtccgct tgcgggaaat tttggacctc aacaagcagg aactgattaa tgcctctatt   3780
cgccgcatta cgtttatgtt cggtttcaag gatggctcgt acccaaaata ctatacgttc   3840
aacggcccga actacaatga gaacgagact atccgacata ttgaacctgc cctcgctttc   3900
caactggaac tggggcggct ctcgaatttc aatattaagc ctatttttac cgacaaccgt   3960
aacatccacg tttacgaggc tgtcagcaaa acaagcccgc tggataagcg attcttcacc   4020
cggggcatta tccgcacagg ccacatccgt gacgatatca gtatccaaga atacctgact   4080
agcgaagcta accgcttgat gagcgacatt ttggataatc tggaagtgac tgatacttcc   4140
aacagcgact tgaatcacat tttatcaac ttcattgccg tgttcgatat ctcgccggaa   4200
gatgtggaag ccgcgtttgg aggctttctg gaacggtttg gcaaacggct gctgcgcttg   4260
cgggtgtcta gcgcggagat tcggattatc atcaaagatc cgcaaacggg ggctcctgtg   4320
ccactgcgcg cgctgattaa taacgtctcg ggttacgtga tcaagaccga gatgtacaca   4380
gaggttaaaa acgctaaagg cgagtgggtc ttcaagagct tgggcaaacc cggcagcatg   4440
catctccgcc ccatcgccac gccgtatccg gtcaaggagt ggctgcagcc caagcgatac   4500
```

```
aaggcgcact tgatggggac gacatatgtt tacgattttc ctgaactgtt ccgtcaagca   4560
agcagctccc agtggaaaaa cttttccgca gatgtgaaat tgactgatga tttcttcatc   4620
tcgaatgagc tcatcgaaga tgagaatggc gagctgaccg aagttgagcg agaacctggt   4680
gccaatgcga ttgggatggt cgcctttaaa atcacggtca aaactcccga gtaccctcgg   4740
ggtcgccagt tcgtcgttgt ggctaacgat atcaccttta agattggatc gtttggcccg   4800
caggaggatg agttctttaa caaggtcact gaatacgccc gaaaacgagg cattccgcgg   4860
atttacttgg cagccaatag cggtgcgcgc atcggcatgg ctgaagaaat cgttccgctg   4920
tttcaggttg cctggaacga cgcggccaac cccgacaagg ggttccagta cttgtatctg   4980
acttccgaag gcatggagac gttgaagaaa tttgataagg agaatagtgt cttgactgag   5040
cggaccgtta ttaacggcga ggagcggttt gtcattaaga ctatcatcgg cagcgaagat   5100
ggcctcggcg tcgaatgttt gcgcgggtcc ggcctgatcg caggggcaac ctcgcgagcc   5160
tatcacgata tctttaccat tactttggtc acgtgtcgtt cggttggcat tggagcatac   5220
ctcgtgcgcc tcggtcagcg cgccatccaa gtggaaggcc aacctatcat tttgactggc   5280
gcgcctgcta tcaataagat gctgggccgt gaagtctaca catcgaacct ccaactgggc   5340
ggtacccaaa ttatgtataa caatggcgtc agccatctga cagccgtcga tgacctggct   5400
ggcgttgaaa agattgttga gtggatgagc tatgtgcccg ccaaacggaa catgccagtc   5460
cccattttgg aaaccaagga tacctgggat cgcccagtgg atttcactcc gactaatgat   5520
gaaacctacg atgtccgctg gatgatcgaa gggcgcgaaa ctgagtcggg cttcgagtac   5580
ggactgtttg ataagggtag tttctttgag actctcagtg gttgggccaa aggcgttgtc   5640
gtcggtcggg cacgtctggg cggcatcccg ctgggagtta ttggtgttga gacacgtacg   5700
gtggaaaatc tgatcccggc tgatccggcc aaccccaata gtgcggaaac gctgattcaa   5760
gagcccgggc aagtgtggca cccgaatagt gcctttaaga cggcgcaggc tattaatgat   5820
tttaacaacg gcgaacaact gcctatgatg attctggcga attggcgggg gtttagtggt   5880
gggcagcgcg acatgttcaa cgaagtgctc aagtacggct ccttcatcgt ggacgccctg   5940
gtcgactata aacaaccaat tatcatctat attcccccta ccggcgagct gcgaggcggt   6000
agctgggtcg tggtggaccc tactattaat gcagatcaaa tggagatgta cgccgacgtg   6060
aatgctcgag cgggcgtgct ggaaccacaa gggatggttg gcatcaaatt ccgccgcgaa   6120
aaactgttgg atactatgaa tcgactggat gataaatatc gcgagctgcg cagccaactg   6180
tcgaacaagt ctctggcccc ggaagtccat caacagattt ctaaacagct ggcagatcgc   6240
gaacgtgaac tcttgccgat ctacggccaa atcagcctcc aatttgccga cctgcatgat   6300
cgcagcagcc gcatggttgc gaaaggtgtc atcagcaaag agctcgagtg gacggaagct   6360
cggcggtttt tcttttggcg gctgcgccga cgcctgaatg aagaatactt gattaagcgt   6420
ctgagccacc aggtcggcga ggctagtcgg ttggaaaaga tcgcccgcat tcggagttgg   6480
tatccggcat cggttgacca cgaggacgat cgccaggtcg ctacctggat cgaagagaac   6540
tacaaaacct tggatgataa gctgaaagga ctgaagctgg agtctttcgc ccaagatctc   6600
gccaagaaga tccgtagcga tcatgacaat gcaatcgacg gtttgagcga ggttatcaag   6660
atgttgtcta ccgacgacaa ggagaagctg ctcaaaacgc tgaagtag                6708
```

<210> SEQ ID NO 7
<211> LENGTH: 1376
<212> TYPE: DNA

<213> ORGANISM: Acinetobacter sp.

<400> SEQUENCE: 7

```
atgcgcccat tacatccgat tgattttata ttcctgtcac tagaaaaaag acaacagcct     60
atgcatgtag gtggtttatt tttgtttcag attcctgata acgccccaga cacctttatt    120
caagatctgg tgaatgatat ccggatatca aaatcaatcc ctgttccacc attcaacaat    180
aaactgaatg ggcttttttg ggatgaagat gaagagtttg atttagatca tcattttcgt    240
catattgcac tgcctcatcc tggtcgtatt cgtgaattgc ttatttatat ttcacaagag    300
cacagtacgc tgctagatcg ggcaaagccc ttgtggacct gcaatattat tgaaggaatt    360
gaaggcaatc gttttgccat gtacttcaaa attcaccatg cgatggtcga tggcgttgct    420
ggtatgcggt taattgaaaa atcactctcc catgatgtaa cagaaaaaag tatcgtgcca    480
ccttggtgtg ttgagggaaa acgtgcaaag cgcttaagag aacctaaaac aggtaaaatt    540
aagaaaatca tgtctggtat taagagtcag cttcaggcga cacccacagt cattcaagag    600
ctttctcaga cagtatttaa agatattgga cgtaatcctg atcatgtttc aagctttcag    660
gcgccttgtt ctattttgaa tcagcgtgtg agctcatcgc gacgttttgc agcacagtct    720
tttgacctag atcgttttcg taatattgcc aaatcgttga atgtgaccat taatgatgtt    780
gtactagcgg tatgttctgg tgcattacgt gcgtatttga tgagtcataa tagtttgcct    840
tcaaaaccat taattgccat ggttccagcc tctattcgca atgacgattc agatgtcagc    900
aaccgtatta cgatgattct ggcaaatttg gcaacccaca aagatgatcc tttacaacgt    960
cttgaaatta tccgccgtag tgttcaaaac tcaaagcaac gcttcaaacg tatgaccagc   1020
gatcagattc taaattatag tgctgtcgta tatggccctg caggactcaa cataatttct   1080
ggcatgatgc caaaacgcca agccttcaat ctggttattt ccaatgtgcc tggcccaaga   1140
gagccacttt actggaatgg tgccaaactt gatgcactct acccagcttc aattgtatta   1200
gacggtcaag cattgaatat tacaatgacc agttatttag ataaacttga agttggtttg   1260
attgcatgcc gtaatgcatt gccaagaatg cagaatttac tgacacattt agaagaagaa   1320
attcaactat ttgaaggcgt aattgcaaag caggaagata ttaaaacagc caatta       1376
```

<210> SEQ ID NO 8
<211> LENGTH: 2589
<212> TYPE: DNA
<213> ORGANISM: Artificial Sequence
<220> FEATURE:
<223> OTHER INFORMATION: Synthetic construct Saccharomyces cerevisiae clone FLH148377.01X SMP2 gene

<400> SEQUENCE: 8

```
atgcagtacg taggcagagc tcttgggtct gtgtctaaaa catggtcttc tatcaatccg     60
gctacgctat caggtgctat agatgtcatt gtagtggagc atccagacgg aaggctatca    120
tgttctccct ttcatgtgag gttcggcaaa tttcaaattc taaagccatc tcaaaagaaa    180
gtccaagtgt ttataaatga gaaactgagt aatatgccaa tgaaactgag tgattctgga    240
gaagcctatt tcgttttcga gatgggtgac caggtcactg atgtccctga cgaattgctt    300
gtgtcgcccg tgatgagcgc cacatcaagc ccccctcaat cacctgaaac atccatctta    360
gaaggaggaa ccgagggtga aggtgaaggt gaaaatgaaa ataagaagaa ggaaaagaaa    420
gtgctagagg aaccagattt tttagatatc aatgacactg gagattcagg cagtaaaaat    480
agtgaaacta cagggtcgct ttctcctact gaatcctcta caacgacacc accagattca    540
```

```
gttgaagaga ggaagcttgt tgagcagcgt acaaagaact ttcagcaaaa actaaacaaa    600

aaactcactg aaatccatat acccagtaaa cttgataaca atggcgactt actactagac    660

actgaaggtt acaagccaaa caagaatatg atgcatgaca cagacataca actgaagcag    720

ttgttaaagg acgaattcgg taatgattca gatatttcca gttttatcaa ggaggacaaa    780

aatggcaaca tcaagatcgt aaatccttac gagcacctta ctgatttatc tcctccaggt    840

acgcctccaa caatggccac aagcggatca gttttaggct tagatgcaat ggaatcagga    900

agtactttga attcgttatc ttcttcacct tctggttccg atactgagga cgaaacatca    960

tttagcaaag aacaaagcag taaaagtgaa aaaactagca agaaaggaac agcaggggagc  1020

ggtgagaccg agaaaagata catacgaacg ataagattga ctaatgacca gttaaagtgc   1080

ctaaatttaa cttatggtga aaatgatctg aaattttccg tagatcacgg aaaagctatt   1140

gttacgtcaa aattattcgt ttggaggtgg gatgttccaa ttgttatcag tgatattgat   1200

ggcaccatca caaaatcgga cgctttaggc catgttctgg caatgatagg aaaagactgg   1260

acgcacttgg gtgtagccaa gttatttagc gagatctcca ggaatggcta taatatactc   1320

tatctaactg caagaagtgc tggacaagct gattccacga ggagttattt gcgatcaatt   1380

gaacagaatg gcagcaaact accaaatggg cctgtgattt tatcacccga tagaacgatg   1440

gctgcgttaa ggcgggaagt aatactaaaa aaacctgaag tctttaaaat cgcgtgtcta   1500

aacgacataa gatccttgta ttttgaagac agtgataacg aagtggatac agaggaaaaa   1560

tcaacaccat tttttgccgg ctttggtaat aggattactg atgctttatc ttacagaact   1620

gtggggatac ctagttcaag aattttcaca ataaatacag agggtgaggt tcatatggaa   1680

ttattggagt tagcaggtta cagaagctcc tatattcata tcaatgagct tgtcgatcat   1740

ttctttccac cagtcagcct tgatagtgtc gatctaagaa ctaatacttc catggttcct   1800

ggctcccccc ctaatagaac gttggataac tttgactcag aaattacttc aggtcgcaaa   1860

acgctattta gaggcaatca ggaagagaaa ttcacagacg taaatttttg gagagacccg   1920

ttagtcgaca tcgacaactt atcggatatt agcaatgatg attctgataa catcgatgaa   1980

gatactgacg tatcacaaca aagcaacatt agtagaaata gggcaaattc agtcaaaacc   2040

gccaaggtca ctaaagcccc gcaaagaaat gtgagcggca gcacaaataa caacgaagtt   2100

ttagccgctt cgtctgatgt agaaaatgcg tctgacctgg tgagttccca tagtagctca   2160

ggatccacgc ccaataaatc tacaatgtcc aaaggggaca ttggaaaaca aatatatttg   2220

gagctaggtt ctccacttgc atcgccaaaa ctaagatatt tagacgatat ggatgatgaa   2280

gactccaatt acaatagaac taaatcaagg agagcatctt ctgcagccgc gactagtatc   2340

gataaagagt tcaaaaagct ctctgtgtca aaggccggcg ctccaacaag aattgtttca   2400

aagatcaacg tttcaaatga cgtacattca cttgggaatt cagataccga atcacgaagg   2460

gagcaaagtg ttaatgaaac agggcgcaat cagctacccc acaactcaat ggacgataaa   2520

gatttggatt caagagtaag cgatgaattc gatgacgatg aattcgacga agatgaattc   2580

gaagattag                                                           2589
```

```
<210> SEQ ID NO 9
<211> LENGTH: 6702
<212> TYPE: DNA
<213> ORGANISM: Artificial Sequence
<220> FEATURE:
<223> OTHER INFORMATION: Synthetic construct Saccharomyces cerevisiae
      clone FLH148869.01X ACC1
```

<400> SEQUENCE: 9

```
atgagcgaag aaagcttatt cgagtcttct ccacagaaga tggagtacga aattacaaac     60
tactcagaaa gacatacaga acttccaggt catttcattg gcctcaatac agtagataaa    120
ctagaggagt ccccgttaag ggactttgtt aagagtcacg gtggtcacac ggtcatatcc    180
aagatcctga tagcaaataa tggtattgcc gccgtgaaag aaattagatc cgtcagaaaa    240
tgggcatacg agacgttcgg cgatgacaga accgtccaat tcgtcgccat ggccacccca    300
gaagatctgg aggccaacgc agaatatatc cgtatggccg atcaatacat tgaagtgcca    360
ggtggtacta ataataacaa ctacgctaac gtagacttga tcgtagacat cgccgaaaga    420
gcagacgtag acgccgtatg ggctggctgg ggtcacgcct ccgagaatcc actattgcct    480
gaaaaattgt cccagtctaa gaggaaagtc atctttattg ggcctccagg taacgccatg    540
aggtctttag gtgataaaat ctcctctacc attgtcgctc aaagtgctaa agtcccatgt    600
attccatggt ctggtaccgg tgttgacacc gttcacgtgg acgagaaaac cggtctggtc    660
tctgtcgacg atgacatcta tcaaaagggt tgttgtacct ctcctgaaga tggtttacaa    720
aaggccaagc gtattggttt tcctgtcatg attaaggcat ccgaaggtgg tggtggtaaa    780
ggtatcagac aagttgaacg tgaagaagat ttcatcgctt tataccacca ggcagccaac    840
gaaattccag gctcccccat tttcatcatg aagttggccg gtagagcgcg tcacttggaa    900
gttcaactgc tagcagatca gtacggtaca aatatttcct tgttcggtag agactgttcc    960
gttcagagac gtcatcaaaa aattatcgaa gaagcaccag ttacaattgc caaggctgaa   1020
acatttcacg agatggaaaa ggctgccgtc agactgggga aactagtcgg ttatgtctct   1080
gccggtaccg tggagtatct atattctcat gatgatggaa aattctactt tttagaattg   1140
aacccaagat tacaagtcga gcatccaaca acggaaatgg tctccggtgt taacttacct   1200
gcagctcaat tacaaatcgc tatgggtatc cctatgcata gaataagtga cattagaact   1260
ttatatggta tgaatcctca ttctgcctca gaaatcgatt tcgaattcaa aactcaagat   1320
gccaccaaga aacaaagaag acctattcca aagggtcatt gtaccgcttg tcgtatcaca   1380
tcagaagatc caaacgatgg attcaagcca tcgggtggta ctttgcatga actaaacttc   1440
cgttcttcct ctaatgtttg ggggttacttc tccgtgggta acaatggtaa tattcactcc   1500
ttttcggact ctcagttcgg ccatattttt gcttttggtg aaaatagaca agcttccagg   1560
aaacacatgg ttgttgccct gaaggaattg tccattaggg gtgatttcag aactactgtg   1620
gaatacttga tcaaactttt ggaaactgaa gatttcgagg ataacactat taccaccggt   1680
tggttggacg atttgattac tcataaaatg accgctgaaa agcctgatcc aactcttgcc   1740
gtcatttgcg gtgccgctac aaaggctttc ttagcatctg aagaagcccg ccacaagtat   1800
atcgaatcct tacaaaaggg acaagttcta tctaaagacc tactgcaaac tatgttccct   1860
gtagatttta tccatgaggg taaaagatac aagttcaccg tagctaaatc cggtaatgac   1920
cgttacacat tatttatcaa tggttctaaa tgtgatatca tactgcgtca actatctgat   1980
ggtggtcttt tgattgccat aggcggtaaa tcgcatacca tctattggaa agaagaagtt   2040
gctgctacaa gattatccgt tgactctatg actactttgt tggaagttga aaacgatcca   2100
acccagttgc gtactccatc ccctggtaaa ttggttaaat tcttggtgga aaatggtgaa   2160
cacattatca agggccaacc atatgcagaa attgaagtta tgaaaatgca aatgcctttg   2220
gtttctcaag aaaatggtat cgtccagtta ttaaagcaac ctggttctac cattgttgca   2280
ggtgatatca tggctattat gactcttgac gatccatcca aggtcaagca cgctctacca   2340
```

```
tttgaaggta tgctgccaga ttttggttct ccagttatcg aaggaaccaa acctgcctat   2400
aaattcaagt cattagtgtc tactttggaa aacattttga agggttatga caaccaagtt   2460
attatgaacg cttccttgca acaattgata gaggttttga gaaatccaaa actgccttac   2520
tcagaatgga aactacacat ctctgcttta cattcaagat tgcctgctaa gctagatgaa   2580
caaatggaag agttagttgc acgttctttg agacgtggtg ctgttttccc agctagacaa   2640
ttaagtaaat tgattgatat ggccgtgaag aatcctgaat acaaccccga caaattgctg   2700
ggcgccgtcg tggaaccatt ggcggatatt gctcataagt actctaacgg gttagaagcc   2760
catgaacatt ctatatttgt ccatttcttg gaagaatatt acgaagttga aaagttattc   2820
aatggtccaa atgttcgtga ggaaaatatc attctgaaat tgcgtgatga aaaccctaaa   2880
gatctagata aagttgcgct aactgttttg tctcattcga aagtttcagc gaagaataac   2940
ctgatcctag ctatcttgaa acattatcaa ccattgtgca agttatcttc taaagtttct   3000
gccattttct ctactcctct acaacatatt gttgaactag aatctaaggc taccgctaag   3060
gtcgctctac aagcaagaga aattttgatt caaggcgctt taccttcggt caaggaaaga   3120
actgaacaaa ttgaacatat cttaaaatcc tctgttgtga aggttgccta tggctcatcc   3180
aatccaaagc gctctgaacc agatttgaat atcttgaagg acttgatcga ttctaattac   3240
gttgtgttcg atgttttact tcaattccta acccatcaag acccagttgt gactgctgca   3300
gctgctcaag tctatattcg tcgtgcttat cgtgcttaca ccataggaga tattagagtt   3360
cacgaaggtg tcacagttcc aattgttgaa tggaaattcc aactaccttc agctgcgttc   3420
tccacctttc caactgttaa atctaaaatg ggtatgaaca gggctgtttc tgtttcagat   3480
ttgtcatatg ttgcaaacag tcagtcatct ccgttaagag aaggtatttt gatggctgtg   3540
gatcatttag atgatgttga tgaaattttg tcacaaagtt tggaagttat tcctcgtcac   3600
caatcttctt ctaacggacc tgctcctgat cgttctggta gctccgcatc gttgagtaat   3660
gttgctaatg tttgtgttgc ttctacagaa ggtttcgaat ctgaagagga aattttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattgagc cggctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aatttagaag tcaccgacac ttcaaattct   4140
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
aagaacgcaa aaggtgaatg ggtatttaag tctttgggta aacctggatc catgcattta   4440
agacctattg ctactcctta ccctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
```

```
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
gttataaacg gtgaagaaag atttgtcatc aagacaatta ttggttctga agatgggtta   5100
ggtgtcgaat gtctacgtgg atctggttta attgctggtg caacgtcaag ggcttaccac   5160
gatatcttca ctatcacctt agtcacttgt agatccgtcg gtatcggtgc ttatttggtt   5220
cgtttgggtc aaagagctat tcaggtcgaa ggccagccaa ttattttaac tggtgctcct   5280
gcaatcaaca aaatgctggg tagagaagtt tatacttcta acttacaatt gggtggtact   5340
caaatcatgt ataacaacgg tgtttcacat ttgactgctg ttgacgattt agctggtgta   5400
gagaagattg ttgaatggat gtcttatgtt ccagccaagc gtaatatgcc agttcctatc   5460
ttggaaacta aagacacatg ggatagacca gttgatttca ctccaactaa tgatgaaact   5520
tacgatgtaa gatggatgat tgaaggtcgt gagactgaaa gtggatttga atatggtttg   5580
tttgataaag ggtctttctt tgaaactttg tcaggatggg ccaaaggtgt tgtcgttggt   5640
agagcccgtc ttggtggtat tccactgggt gttattggtg ttgaaacaag aactgtcgag   5700
aacttgattc ctgctgatcc agctaatcca aatagtgctg aaacattaat tcaagaacct   5760
ggtcaagttt ggcatccaaa ctccgccttc aagactgctc aagctatcaa tgactttaac   5820
aacggtgaac aattgccaat gatgattttg gccaactgga gaggtttctc tggtggtcaa   5880
cgtgatatgt tcaacgaagt cttgaagtat ggttcgttta ttgttgacgc attggtggat   5940
tacaaacaac caattattat ctatatccca cctaccggtg aactaagagg tggttcatgg   6000
gttgttgtcg atccaactat caacgctgac caaatggaaa tgtatgccga cgtcaacgct   6060
agagctggtg ttttggaacc acaaggtatg gttggtatca agttccgtag agaaaaattg   6120
ctggacacca tgaacagatt ggatgacaag tacagagaat tgagatctca attatccaac   6180
aagagtttgg ctccagaagt acatcagcaa atatccaagc aattagctga tcgtgagaga   6240
gaactattgc caatttacgg acaaatcagt cttcaatttg ctgatttgca cgataggtct   6300
tcacgtatgg tggccaaggg tgttatttct aaggaactgg aatggaccga ggcacgtcgt   6360
ttcttcttct ggagattgag aagaagattg aacgaagaat atttgattaa aaggttgagc   6420
catcaggtag gcgaagcatc aagattagaa aagatcgcaa gaattagatc gtggtaccct   6480
gcttcagtgg accatgaaga tgataggcaa gtcgcaacat ggattgaaga aaactacaaa   6540
actttggacg ataaactaaa gggtttgaaa ttagagtcat tcgctcaaga cttagctaaa   6600
aagatcagaa gcgaccatga caatgctatt gatggattat ctgaagttat caagatgtta   6660
tctaccgatg ataaagaaaa attgttgaag actttgaaat ag                      6702
```

<210> SEQ ID NO 10
<211> LENGTH: 9
<212> TYPE: PRT
<213> ORGANISM: Artificial Sequence
<220> FEATURE:
<223> OTHER INFORMATION: Domain 1 lipid phosphatase catalytic motif
<220> FEATURE:
<221> NAME/KEY: VARIANT
<222> LOCATION: 2, 3, 4, 5, 6, 7
<223> OTHER INFORMATION: Xaa = Any Amino Acid

<400> SEQUENCE: 10

```
Lys Xaa Xaa Xaa Xaa Xaa Xaa Arg Pro
 1               5
```

<210> SEQ ID NO 11
<211> LENGTH: 4
<212> TYPE: PRT
<213> ORGANISM: Artificial Sequence
<220> FEATURE:
<223> OTHER INFORMATION: Domain 2 lipid phosphatase catalytic motif

<400> SEQUENCE: 11

```
Pro Ser Gly His
 1
```

<210> SEQ ID NO 12
<211> LENGTH: 12
<212> TYPE: PRT
<213> ORGANISM: Artificial Sequence
<220> FEATURE:
<223> OTHER INFORMATION: Domain 3 lipid phosphatase catalytic motif
<220> FEATURE:
<221> NAME/KEY: VARIANT
<222> LOCATION: 3, 4, 5, 6, 7, 9, 10, 11
<223> OTHER INFORMATION: Xaa = Any Amino Acid

<400> SEQUENCE: 12

```
Ser Arg Xaa Xaa Xaa Xaa Xaa His Xaa Xaa Xaa Asp
 1               5                   10
```

<210> SEQ ID NO 13
<211> LENGTH: 7
<212> TYPE: PRT
<213> ORGANISM: Artificial Sequence
<220> FEATURE:
<223> OTHER INFORMATION: Heptapeptide retention motif
<220> FEATURE:
<221> NAME/KEY: VARIANT
<222> LOCATION: 3
<223> OTHER INFORMATION: Xaa = Any Amino Acid

<400> SEQUENCE: 13

```
Phe Tyr Xaa Asp Trp Trp Asn
 1               5
```

<210> SEQ ID NO 14
<211> LENGTH: 446
<212> TYPE: PRT
<213> ORGANISM: Streptomyces coelicolor

<400> SEQUENCE: 14

```
Met Thr Pro Asp Pro Leu Ala Pro Leu Asp Leu Ala Phe Trp Asn Ile
 1               5                   10                  15

Glu Ser Ala Glu His Pro Met His Leu Gly Ala Leu Gly Val Phe Glu
            20                  25                  30

Ala Asp Ser Pro Thr Ala Gly Ala Leu Ala Ala Asp Leu Leu Ala Ala
        35                  40                  45

Arg Ala Pro Ala Val Pro Gly Leu Arg Met Arg Ile Arg Asp Thr Trp
    50                  55                  60

Gln Pro Pro Met Ala Leu Arg Arg Pro Phe Ala Phe Gly Gly Ala Thr
65                  70                  75                  80

Arg Glu Pro Asp Pro Arg Phe Asp Pro Leu Asp His Val Arg Leu His
                85                  90                  95
```

```
Ala Pro Ala Thr Asp Phe His Ala Arg Ala Gly Arg Leu Met Glu Arg
            100                 105                 110

Pro Leu Glu Arg Gly Arg Pro Pro Trp Glu Ala His Val Leu Pro Gly
        115                 120                 125

Ala Asp Gly Gly Ser Phe Ala Val Leu Phe Lys Phe His His Ala Leu
    130                 135                 140

Ala Asp Gly Leu Arg Ala Leu Thr Leu Ala Ala Gly Val Leu Asp Pro
145                 150                 155                 160

Met Asp Leu Pro Ala Pro Arg Pro Arg Pro Glu Gln Pro Pro Arg Gly
                165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Ala Leu Ser
        195                 200                 205

Thr Leu Asp Val Arg Ser Ser Pro Ala Leu Thr Ala Ala Ser Ser Gly
    210                 215                 220

Thr Arg Arg Thr Ala Gly Val Ser Val Asp Leu Asp Asp Val His His
225                 230                 235                 240

Val Arg Lys Thr Thr Gly Gly Thr Val Asn Asp Val Leu Ile Ala Val
                245                 250                 255

Val Ala Gly Ala Leu Arg Arg Trp Leu Asp Glu Arg Gly Asp Gly Ser
            260                 265                 270

Glu Gly Val Ala Pro Arg Ala Leu Ile Pro Val Ser Arg Arg Arg Pro
        275                 280                 285

Arg Ser Ala His Pro Gln Gly Asn Arg Leu Ser Gly Tyr Leu Met Arg
    290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
                325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
        355                 360                 365

Val Thr Ser Val Pro Leu Pro Ser Leu Gly Leu Arg Leu Gly Gly His
    370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
                405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
        435                 440                 445


<210> SEQ ID NO 15
<211> LENGTH: 457
<212> TYPE: PRT
<213> ORGANISM: Alcanivorax borkumensis

<400> SEQUENCE: 15

Met Lys Ala Leu Ser Pro Val Asp Gln Leu Phe Leu Trp Leu Glu Lys
 1               5                  10                  15

Arg Gln Gln Pro Met His Val Gly Gly Leu Gln Leu Phe Ser Phe Pro
            20                  25                  30
```

-continued

```
Glu Gly Ala Gly Pro Lys Tyr Val Ser Glu Leu Ala Gln Gln Met Arg
        35                  40                  45

Asp Tyr Cys His Pro Val Ala Pro Phe Asn Gln Arg Leu Thr Arg Arg
    50                  55                  60

Leu Gly Gln Tyr Tyr Trp Thr Arg Asp Lys Gln Phe Asp Ile Asp His
65                  70                  75                  80

His Phe Arg His Glu Ala Leu Pro Lys Pro Gly Arg Ile Arg Glu Leu
                85                  90                  95

Leu Ser Leu Val Ser Ala Glu His Ser Asn Leu Leu Asp Arg Glu Arg
            100                 105                 110

Pro Met Trp Glu Ala His Leu Ile Glu Gly Ile Arg Gly Arg Gln Phe
        115                 120                 125

Ala Leu Tyr Tyr Lys Ile His His Ser Val Met Asp Gly Ile Ser Ala
    130                 135                 140

Met Arg Ile Ala Ser Lys Thr Leu Ser Thr Asp Pro Ser Glu Arg Glu
145                 150                 155                 160

Met Ala Pro Ala Trp Ala Phe Asn Thr Lys Lys Arg Ser Arg Ser Leu
                165                 170                 175

Pro Ser Asn Pro Val Asp Met Ala Ser Ser Met Ala Arg Leu Thr Ala
            180                 185                 190

Ser Ile Ser Lys Gln Ala Ala Thr Val Pro Gly Leu Ala Arg Glu Val
        195                 200                 205

Tyr Lys Val Thr Gln Lys Ala Lys Lys Asp Glu Asn Tyr Val Ser Ile
    210                 215                 220

Phe Gln Ala Pro Asp Thr Ile Leu Asn Asn Thr Ile Thr Gly Ser Arg
225                 230                 235                 240

Arg Phe Ala Ala Gln Ser Phe Pro Leu Pro Arg Leu Lys Val Ile Ala
                245                 250                 255

Lys Ala Tyr Asn Cys Thr Ile Asn Thr Val Val Leu Ser Met Cys Gly
            260                 265                 270

His Ala Leu Arg Glu Tyr Leu Ile Ser Gln His Ala Leu Pro Asp Glu
        275                 280                 285

Pro Leu Ile Ala Met Val Pro Met Ser Leu Arg Gln Asp Asp Ser Thr
    290                 295                 300

Gly Gly Asn Gln Ile Gly Met Ile Leu Ala Asn Leu Gly Thr His Ile
305                 310                 315                 320

Cys Asp Pro Ala Asn Arg Leu Arg Val Ile His Asp Ser Val Glu Glu
                325                 330                 335

Ala Lys Ser Arg Phe Ser Gln Met Ser Pro Glu Glu Ile Leu Asn Phe
            340                 345                 350

Thr Ala Leu Thr Met Ala Pro Thr Gly Leu Asn Leu Leu Thr Gly Leu
        355                 360                 365

Ala Pro Lys Trp Arg Ala Phe Asn Val Val Ile Ser Asn Ile Pro Gly
    370                 375                 380

Pro Lys Glu Pro Leu Tyr Trp Asn Gly Ala Gln Leu Gln Gly Val Tyr
385                 390                 395                 400

Pro Val Ser Ile Ala Leu Asp Arg Ile Ala Leu Asn Ile Thr Leu Thr
                405                 410                 415

Ser Tyr Val Asp Gln Met Glu Phe Gly Leu Ile Ala Cys Arg Arg Thr
            420                 425                 430

Leu Pro Ser Met Gln Arg Leu Leu Asp Tyr Leu Glu Gln Ser Ile Arg
        435                 440                 445
```

```
Glu Leu Glu Ile Gly Ala Gly Ile Lys
    450                 455


<210> SEQ ID NO 16
<211> LENGTH: 1341
<212> TYPE: DNA
<213> ORGANISM: Artificial Sequence
<220> FEATURE:
<223> OTHER INFORMATION: Codon-optimized Streptomyces coelicolor DGAT

<400> SEQUENCE: 16

atgacgcctg acccgttggc tcccttggac ttggctttct ggaatatcga aagtgccgag      60

cacccgatgc acttgggggc actgggggtc tttgaggcgg atagtccaac cgctggtgca     120

ctcgccgcgg atctcctggc tgcccgcgct cccgcagtgc ccgggctgcg catgcggatt     180

cgcgatacat ggcagccgcc tatggcgctc cgtcgccctt ttgcttttgg cggtgctaca     240

cgcgagcccg acccgcggtt tgatccactc gatcatgtgc ggctccatgc cccagcgacg     300

gatttccacg cacgcgcagg tcggttgatg gagcgccctc tggaacgagg ccgtcctcct     360

tgggaagccc atgtcctgcc aggggctgac ggtggatcgt ttgcggtctt gtttaagttc     420

catcatgccc tggccgacgg tctgcgggcg ctgacgctgg cggcgggcgt gctcgatccg     480

atggatctcc ccgctccacg gccccgccca gagcagcccc cccgtggtct cctgccggat     540

gtccgcgcgc tgccggatcg gctgcgaggg gctctgtctg acgcgggccg cgcgttggac     600

atcggcgccg ccgcagccct cagcaccctg gatgtgcgga gcagtcccgc tctgactgcg     660

gcgtcctcgg gcacgcgacg taccgccggc gtgtccgtgg atctcgacga cgtgcaccat     720

gttcgcaaaa cgacaggcgg taccgttaac gatgttttga tcgccgttgt tgccggggcc     780

ctgcgacgct ggctggatga acgaggcgat gggtcggaag gcgtcgcccc gcgcgccctc     840

attcccgtca gccggcggcg acctcggagc gcacacccgc aaggcaaccg attgagtggc     900

tacctgatgc gcttgccggt cggcgacccg gaccctctcg cacggttggg aaccgtccgt     960

gccgcgatgg atcgaaataa ggatgcgggg cccggccgcg gagctggcgc agttgctctc    1020

ttggcagacc acgttcctgc cctgggccac cgcctgggtg gacccctcgt ctcgggcgct    1080

gctcgactgt ggttcgatct gttggtcacg agcgtcccgt tgccctcttt gggtttgcgc    1140

ctcggtgggc atccgctgac cgaagtgtac ccactggccc ccctggcccg tggccactcc    1200

ttggcggtgg cggtgagcac ttatcgcggt cgggttcatt acggtctcct cgctgatgct    1260

aaagccgttc ctgatctgga tcgtctggca gtggccgtcg ccgaggaggt tgaaaccttg    1320

ctcactgcgt gccgccccta g                                              1341


<210> SEQ ID NO 17
<211> LENGTH: 1374
<212> TYPE: DNA
<213> ORGANISM: Artificial Sequence
<220> FEATURE:
<223> OTHER INFORMATION: Codon-optimized Alcanivorax borkumensis DGAT

<400> SEQUENCE: 17

atgaaagctt tgagccccgt tgatcagctg tttctgtggt tggaaaaacg gcagcaaccc      60

atgcatgtgg gtgggttgca gctgttctcc tttcccgaag gcgcggggcc gaaatatgtc     120

tcggaactgg cccaacagat gcgcgattat tgtcaccctg tcgccccgtt caaccaacgt     180

ctgacacggc gcctggggca atactactgg acacgtgata agcaatttga cattgaccat     240

cattttcggc acgaggccct gcccaaaccg ggtcggattc gcgagttgct cagcttggtg     300
```

```
agtgcggaac actccaactt gttggatcgt gaacgaccca tgtgggaagc gcacctgatc    360

gaaggaatcc gcgggcgcca atttgccttg tattacaaaa ttcatcactc cgtcatggac    420

ggtatctccg ctatgcggat tgcctctaag accttgtcca cggaccccag tgagcgggag    480

atggcccccg cttgggcgtt taatactaag aagcgatcgc gcagcctgcc aagcaatccc    540

gtggatatgg cgagctcgat ggctcgactc actgcaagta tttcgaaaca agctgccacc    600

gtgcccggcc tggcacgaga ggtctacaag gtgacccaaa aagctaaaaa ggatgaaaat    660

tacgttagta ttttccaagc accagacacc atcctcaata atacgattac gggcagtcga    720

cgcttcgccg ctcagtcgtt ccctctcccc cgtctgaagg ttatcgctaa ggcttacaac    780

tgcactatta acacggttgt gctctcgatg tgcggccacg ccctgcgcga atacctcatc    840

agtcaacatg ccctgccgga tgaacccctg atcgcgatgg tccctatgag cctgcgccaa    900

gatgatagca ccggaggcaa ccagatcgga atgattttgg cgaatctggg cacgcatatc    960

tgcgatcctg ccaatcgcct gcgtgtcatc catgatagcg tggaggaggc gaaaagccgt   1020

tttagccaaa tgtctccgga ggagattctg aactttacag cactcactat ggcgccgacc   1080

ggtctgaact tgctcaccgg tttggctccc aaatggcgcg catttaacgt cgttatctct   1140

aacatcccag ggccaaagga accactgtac tggaatgggg cacagctcca gggtgtgtat   1200

ccggtctcca tcgccttgga tcggattgcc ctgaacatta cactgacgtc ttatgttgat   1260

cagatggagt tcggcttgat tgcgtgtcgc cggaccctcc cgtcgatgca acgactcctc   1320

gactatctcg aacagagtat ccgcgaactg gagattggcg cgggcatcaa atag         1374


<210> SEQ ID NO 18
<211> LENGTH: 460
<212> TYPE: PRT
<213> ORGANISM: Acinetobacter baylii sp.

<400> SEQUENCE: 18

Met Glu Phe Arg Pro Leu His Pro Ile Asp Phe Ile Phe Leu Ser Leu
 1               5                  10                  15

Glu Lys Arg Gln Gln Pro Met His Val Gly Gly Leu Phe Leu Phe Gln
            20                  25                  30

Ile Pro Asp Asn Ala Pro Asp Thr Phe Ile Gln Asp Leu Val Asn Asp
        35                  40                  45

Ile Arg Ile Ser Lys Ser Ile Pro Val Pro Pro Phe Asn Asn Lys Leu
    50                  55                  60

Asn Gly Leu Phe Trp Asp Glu Asp Glu Glu Phe Asp Leu Asp His His
65                  70                  75                  80

Phe Arg His Ile Ala Leu Pro His Pro Gly Arg Ile Arg Glu Leu Leu
                85                  90                  95

Ile Tyr Ile Ser Gln Glu His Ser Thr Leu Leu Asp Arg Ala Lys Pro
            100                 105                 110

Leu Trp Thr Cys Asn Ile Ile Glu Gly Ile Glu Gly Asn Arg Phe Ala
        115                 120                 125

Met Tyr Phe Lys Ile His His Ala Met Val Asp Gly Val Ala Gly Met
    130                 135                 140

Arg Leu Ile Glu Lys Ser Leu Ser His Asp Val Thr Glu Lys Ser Ile
145                 150                 155                 160

Val Pro Pro Trp Cys Val Glu Gly Lys Arg Ala Lys Arg Leu Arg Glu
                165                 170                 175

Pro Lys Thr Gly Lys Ile Lys Lys Ile Met Ser Gly Ile Lys Ser Gln
            180                 185                 190
```

```
Leu Gln Ala Thr Pro Thr Val Ile Gln Glu Leu Ser Gln Thr Val Phe
        195                 200                 205

Lys Asp Ile Gly Arg Asn Pro Asp His Val Ser Ser Phe Gln Ala Pro
    210                 215                 220

Cys Ser Ile Leu Asn Gln Arg Val Ser Ser Ser Arg Arg Phe Ala Ala
225                 230                 235                 240

Gln Ser Phe Asp Leu Asp Arg Phe Arg Asn Ile Ala Lys Ser Leu Asn
                245                 250                 255

Val Thr Ile Asn Asp Val Val Leu Ala Val Cys Ser Gly Ala Leu Arg
            260                 265                 270

Ala Tyr Leu Met Ser His Asn Ser Leu Pro Ser Lys Pro Leu Ile Ala
        275                 280                 285

Met Val Pro Ala Ser Ile Arg Asn Asp Asp Ser Asp Val Ser Asn Arg
    290                 295                 300

Ile Thr Met Ile Leu Ala Asn Leu Ala Thr His Lys Asp Asp Pro Leu
305                 310                 315                 320

Gln Arg Leu Glu Ile Ile Arg Arg Ser Val Gln Asn Ser Lys Gln Arg
                325                 330                 335

Phe Lys Arg Met Thr Ser Asp Gln Ile Leu Asn Tyr Ser Ala Val Val
            340                 345                 350

Tyr Gly Pro Ala Gly Leu Asn Ile Ile Ser Gly Met Met Pro Lys Arg
        355                 360                 365

Gln Ala Phe Asn Leu Val Ile Ser Asn Val Pro Gly Pro Arg Glu Pro
    370                 375                 380

Leu Tyr Trp Asn Gly Ala Lys Leu Asp Ala Leu Tyr Pro Ala Ser Ile
385                 390                 395                 400

Val Leu Asp Gly Gln Ala Leu Asn Ile Thr Met Thr Ser Tyr Leu Asp
                405                 410                 415

Lys Leu Glu Val Gly Leu Ile Ala Cys Arg Asn Ala Leu Pro Arg Met
            420                 425                 430

Gln Asn Leu Leu Thr His Leu Glu Glu Glu Ile Gln Leu Phe Glu Gly
        435                 440                 445

Val Ile Ala Lys Gln Glu Asp Ile Lys Thr Ala Asn
    450                 455                 460


<210> SEQ ID NO 19
<211> LENGTH: 1383
<212> TYPE: DNA
<213> ORGANISM: Artificial Sequence
<220> FEATURE:
<223> OTHER INFORMATION: Codon-optimized Acinetobacter baylii sp. DGATd

<400> SEQUENCE: 19

atggaattcc ggcccttgca ccccattgac ttcatctttc tgagtttgga gaaacggcaa      60

cagcccatgc atgtcggtgg cttgtttctc ttccaaatcc ccgataacgc cccggacacc     120

tttattcagg atctggtcaa tgatatccgg atctcgaaat cgatccccgt gccgccgttt     180

aataataaac tgaacggcct cttttgggac gaagacgagg aatttgatct ggatcaccat     240

tttcggcaca tcgctttgcc ccacccgggt cggattcgcg aactcctgat ctatattagc     300

caagaacaca gcacgttgtt ggaccgggcc aaaccgctct ggacgtgcaa tatcatcgaa     360

ggcatcgaag gcaaccgctt tgcgatgtac ttcaagattc atcacgcgat ggttgacggt     420

gtcgctggca tgcgcctgat cgaaaaatcg ctgagccatg atgtgaccga aaagagtatc     480

gtcccccccct ggtgcgtgga aggtaagcgc gccaagcgcc tccgcgaacc gaaaacgggc     540
```

```
aagattaaga aaatcatgag cggtatcaag tcgcagctgc aggctacccc gaccgtgatc    600

caggagctgt cgcaaaccgt gtttaaggat attggtcgga acccggatca tgtcagtagt    660

ttccaagctc cctgttcgat cttgaatcag cgcgttagca gcagccgccg gttcgctgct    720

caaagttttg atctcgatcg gtttcggaat attgccaagt cgctgaacgt caccatcaat    780

gatgtggttc tcgcggtttg ttcgggtgcc ctccgcgcgt atctgatgag ccataacagt    840

ctccccagta agccgctgat tgctatggtt cccgcgtcga ttcggaatga cgacagcgat    900

gtgagcaacc ggattaccat gatcctggct aacctcgcga cccacaaaga tgatccgttg    960

caacgcctgg agattatccg ccgcagtgtg cagaacagta aacagcgctt caaacggatg   1020

accagtgatc aaattctgaa ttacagcgct gtggtctatg gtcccgccgg cttgaatatt   1080

atcagtggta tgatgcccaa acgccaagcg tttaacttgg tgatcagtaa tgtgccgggt   1140

ccgcgcgaac ccttgtattg gaacggtgct aaactcgatg ccctctaccc cgccagtatc   1200

gtgctcgatg gccaggctct caatattacc atgaccagct atctcgataa actcgaggtg   1260

ggtttgattg cgtgccgcaa cgcgctgccc cgcatgcaga acttgctgac ccacctggaa   1320

gaggaaatcc agctcttcga gggcgtgatt gcgaagcagg aagatattaa aacggccaac   1380

tag                                                                 1383


<210> SEQ ID NO 20
<211> LENGTH: 325
<212> TYPE: PRT
<213> ORGANISM: Synechococcus sp. PCC7002

<400> SEQUENCE: 20

Met Pro Lys Thr Glu Arg Arg Thr Phe Leu Leu Asp Phe Glu Lys Pro
1               5                   10                  15

Leu Ser Glu Leu Glu Ser Arg Ile His Gln Ile Arg Asp Leu Ala Ala
            20                  25                  30

Glu Asn Asn Val Asp Val Ser Glu Gln Ile Gln Gln Leu Glu Ala Arg
        35                  40                  45

Ala Asp Gln Leu Arg Glu Glu Ile Phe Ser Thr Leu Thr Pro Ala Gln
    50                  55                  60

Arg Leu Gln Leu Ala Arg His Pro Arg Arg Pro Ser Thr Leu Asp Tyr
65                  70                  75                  80

Val Gln Met Met Ala Asp Glu Trp Phe Glu Leu His Gly Asp Arg Gly
                85                  90                  95

Gly Ser Asp Asp Pro Ala Leu Ile Gly Gly Val Ala Arg Phe Asp Gly
            100                 105                 110

Gln Pro Val Met Met Leu Gly His Gln Lys Gly Arg Asp Thr Lys Asp
        115                 120                 125

Asn Val Ala Arg Asn Phe Gly Met Pro Ala Pro Gly Gly Tyr Arg Lys
    130                 135                 140

Ala Met Arg Leu Met Asp His Ala Asn Arg Phe Gly Met Pro Ile Leu
145                 150                 155                 160

Thr Phe Ile Asp Thr Pro Gly Ala Trp Ala Gly Leu Glu Ala Glu Lys
                165                 170                 175

Leu Gly Gln Gly Glu Ala Ile Ala Phe Asn Leu Arg Glu Met Phe Ser
            180                 185                 190

Leu Asp Val Pro Ile Ile Cys Thr Val Ile Gly Glu Gly Gly Ser Gly
        195                 200                 205

Gly Ala Leu Gly Ile Gly Val Gly Asp Arg Val Leu Met Leu Lys Asn
```

```
    210                 215                 220

Ser Val Tyr Thr Val Ala Thr Pro Glu Ala Cys Ala Ala Ile Leu Trp
225                 230                 235                 240

Lys Asp Ala Gly Lys Ser Glu Gln Ala Ala Ala Ala Leu Lys Ile Thr
                245                 250                 255

Ala Glu Asp Leu Lys Ser Leu Glu Ile Ile Asp Glu Ile Val Pro Glu
            260                 265                 270

Pro Ala Ser Cys Ala His Ala Asp Pro Ile Gly Ala Ala Gln Leu Leu
        275                 280                 285

Lys Ala Ala Ile Gln Asp Asn Leu Gln Ala Leu Leu Lys Leu Thr Pro
    290                 295                 300

Glu Arg Arg Arg Glu Leu Arg Tyr Gln Arg Phe Arg Lys Ile Gly Val
305                 310                 315                 320

Phe Leu Glu Ser Ser
                325


<210> SEQ ID NO 21
<211> LENGTH: 165
<212> TYPE: PRT
<213> ORGANISM: Synechococcus sp. PCC 7002

<400> SEQUENCE: 21

Met Ala Ile Asn Leu Gln Glu Ile Gln Glu Leu Leu Ser Thr Ile Gly
 1               5                  10                  15

Gln Thr Asn Val Thr Glu Phe Glu Leu Lys Thr Asp Asp Phe Glu Leu
            20                  25                  30

Arg Val Ser Lys Gly Thr Val Val Ala Ala Pro Gln Thr Met Val Met
        35                  40                  45

Ser Glu Ala Ile Ala Gln Pro Ala Met Ser Thr Pro Val Val Ser Gln
    50                  55                  60

Ala Thr Ala Thr Pro Glu Ala Ser Gln Ala Glu Thr Pro Ala Pro Ser
65                  70                  75                  80

Val Ser Ile Asp Asp Lys Trp Val Ala Ile Thr Ser Pro Met Val Gly
                85                  90                  95

Thr Phe Tyr Arg Ala Pro Ala Pro Gly Glu Asp Pro Phe Val Ala Val
            100                 105                 110

Gly Asp Arg Val Gly Asn Gly Gln Thr Val Cys Ile Ile Glu Ala Met
        115                 120                 125

Lys Leu Met Asn Glu Ile Glu Ala Glu Val Ser Gly Glu Val Val Lys
    130                 135                 140

Ile Ala Val Glu Asp Gly Glu Pro Ile Glu Phe Gly Gln Thr Leu Met
145                 150                 155                 160

Trp Val Asn Pro Thr
                165


<210> SEQ ID NO 22
<211> LENGTH: 448
<212> TYPE: PRT
<213> ORGANISM: Synechococcus sp. PCC 7002

<400> SEQUENCE: 22

Met Gln Phe Ser Lys Ile Leu Ile Ala Asn Arg Gly Glu Val Ala Leu
 1               5                  10                  15

Arg Ile Ile His Thr Cys Gln Glu Leu Gly Ile Ala Thr Val Ala Val
            20                  25                  30

His Ser Thr Val Asp Arg Gln Ala Leu His Val Gln Leu Ala Asp Glu
```

```
        35                  40                  45

Ser Ile Cys Ile Gly Pro Pro Gln Ser Ser Lys Ser Tyr Leu Asn Ile
    50                  55                  60

Pro Asn Ile Ile Ala Ala Ala Leu Ser Ser Asn Ala Asp Ala Ile His
65                  70                  75                  80

Pro Gly Tyr Gly Phe Leu Ala Glu Asn Ala Lys Phe Ala Glu Ile Cys
                85                  90                  95

Ala Asp His Gln Ile Thr Phe Ile Gly Pro Ser Pro Glu Ala Met Ile
            100                 105                 110

Ala Met Gly Asp Lys Ser Thr Ala Lys Lys Thr Met Gln Ala Ala Lys
        115                 120                 125

Val Pro Thr Val Pro Gly Ser Ala Gly Leu Val Ala Ser Glu Glu Gln
    130                 135                 140

Ala Leu Glu Ile Ala Gln Gln Ile Gly Tyr Pro Val Met Ile Lys Ala
145                 150                 155                 160

Thr Ala Gly Gly Gly Gly Arg Gly Met Arg Leu Val Pro Ser Ala Glu
                165                 170                 175

Glu Leu Pro Arg Leu Tyr Arg Ala Ala Gln Gly Glu Ala Glu Ala Ala
            180                 185                 190

Phe Gly Asn Gly Gly Val Tyr Ile Glu Lys Phe Ile Glu Arg Pro Arg
        195                 200                 205

His Ile Glu Phe Gln Ile Leu Ala Asp Gln Tyr Gly Asn Val Ile His
    210                 215                 220

Leu Gly Glu Arg Asp Cys Ser Ile Gln Arg Arg His Gln Lys Leu Leu
225                 230                 235                 240

Glu Glu Ala Pro Ser Ala Ile Leu Thr Pro Arg Leu Arg Asp Lys Met
                245                 250                 255

Gly Lys Ala Ala Val Lys Ala Ala Lys Ser Ile Asp Tyr Val Gly Ala
            260                 265                 270

Gly Thr Val Glu Phe Leu Val Asp Lys Asn Gly Asp Phe Tyr Phe Met
        275                 280                 285

Glu Met Asn Thr Arg Ile Gln Val Glu His Pro Val Thr Glu Met Val
    290                 295                 300

Thr Gly Leu Asp Leu Ile Ala Glu Gln Ile Lys Val Ala Gln Gly Asp
305                 310                 315                 320

Arg Leu Ser Leu Asn Gln Asn Gln Val Asn Leu Asn Gly His Ala Ile
                325                 330                 335

Glu Cys Arg Ile Asn Ala Glu Asp Pro Asp His Asp Phe Arg Pro Thr
            340                 345                 350

Pro Gly Lys Ile Ser Gly Tyr Leu Pro Pro Gly Gly Pro Gly Val Arg
        355                 360                 365

Met Asp Ser His Val Tyr Thr Asp Tyr Glu Ile Ser Pro Tyr Tyr Asp
    370                 375                 380

Ser Leu Ile Gly Lys Leu Ile Val Trp Gly Pro Asp Arg Asp Thr Ala
385                 390                 395                 400

Ile Arg Arg Met Lys Arg Ala Leu Arg Glu Cys Ala Ile Thr Gly Val
                405                 410                 415

Ser Thr Thr Ile Ser Phe His Gln Lys Ile Leu Asn His Pro Ala Phe
            420                 425                 430

Leu Ala Ala Asp Val Asp Thr Asn Phe Ile Gln Gln His Met Leu Pro
        435                 440                 445

<210> SEQ ID NO 23
```

```
<211> LENGTH: 319
<212> TYPE: PRT
<213> ORGANISM: Synechococcus sp. PCC 7002

<400> SEQUENCE: 23

Met Ser Leu Phe Asp Trp Phe Ala Ala Asn Arg Gln Asn Ser Glu Thr
1               5                   10                  15

Gln Leu Gln Pro Gln Gln Glu Arg Glu Ile Ala Asp Gly Leu Trp Thr
            20                  25                  30

Lys Cys Lys Ser Cys Asp Ala Leu Thr Tyr Thr Lys Asp Leu Arg Asn
        35                  40                  45

Asn Gln Met Val Cys Lys Glu Cys Gly Phe His Asn Arg Val Gly Ser
    50                  55                  60

Arg Glu Arg Val Arg Gln Leu Ile Asp Glu Gly Thr Trp Thr Glu Ile
65                  70                  75                  80

Ser Gln Asn Val Ala Pro Thr Asp Pro Leu Lys Phe Arg Asp Lys Lys
                85                  90                  95

Ala Tyr Ser Asp Arg Leu Lys Asp Tyr Gln Glu Lys Thr Asn Leu Thr
            100                 105                 110

Asp Ala Val Ile Thr Gly Thr Gly Leu Ile Asp Gly Leu Pro Leu Ala
        115                 120                 125

Leu Ala Val Met Asp Phe Gly Phe Met Gly Gly Ser Met Gly Ser Val
    130                 135                 140

Val Gly Glu Lys Ile Cys Arg Leu Val Glu His Gly Thr Ala Glu Gly
145                 150                 155                 160

Leu Pro Val Val Val Val Cys Ala Ser Gly Gly Ala Arg Met Gln Glu
                165                 170                 175

Gly Met Leu Ser Leu Met Gln Met Ala Lys Ile Ser Gly Ala Leu Glu
            180                 185                 190

Arg His Arg Thr Lys Lys Leu Leu Tyr Ile Pro Val Leu Thr Asn Pro
        195                 200                 205

Thr Thr Gly Gly Val Thr Ala Ser Phe Ala Met Leu Gly Asp Leu Ile
    210                 215                 220

Leu Ala Glu Pro Lys Ala Thr Ile Gly Phe Ala Gly Arg Arg Val Ile
225                 230                 235                 240

Glu Gln Thr Leu Arg Glu Lys Leu Pro Asp Asp Phe Gln Thr Ser Glu
                245                 250                 255

Tyr Leu Leu Gln His Gly Phe Val Asp Ala Ile Val Pro Arg Thr Glu
            260                 265                 270

Leu Lys Lys Thr Leu Ala Gln Met Ile Ser Leu His Gln Pro Phe His
        275                 280                 285

Pro Ile Leu Pro Glu Leu Gln Leu Ala Pro His Val Glu Lys Glu Lys
    290                 295                 300

Val Tyr Glu Pro Ile Ala Ser Thr Ser Thr Asn Asp Phe Tyr Lys
305                 310                 315


<210> SEQ ID NO 24
<211> LENGTH: 978
<212> TYPE: DNA
<213> ORGANISM: Synechococcus sp. PCC 7002

<400> SEQUENCE: 24

atgccgaaaa cggagcgccg gacgtttctg cttgattttg aaaaacctct ttcggaatta      60

gaatcacgca tccatcaaat tcgtgatctt gctgcggaga ataatgttga tgtttcagaa     120

cagattcagc agctagaggc gcgggcagac cagctccggg aagaaatttt tagtaccctc     180
```

```
accccggccc aacggctgca attggcacgg catccccggc gtcccagcac ccttgattat    240
gttcaaatga tggcggacga atggtttgaa ctccatggcg atcgcggtgg atctgatgat    300
ccggctctca ttggcggggt ggcccgcttc gatggtcaac cggtgatgat gctagggcac    360
caaaaaggac gggatacgaa ggataatgtc gcccgcaatt ttggcatgcc agctcctggg    420
ggctaccgta aggcgatgcg gctgatggac catgccaacc gttttgggat gccgatttta    480
acgtttattg atactcctgg ggcttgggcg ggtttagaag cggaaaagtt gggccaaggg    540
gaggcgatcg cctttaacct ccgggaaatg tttagcctcg atgtgccgat tatttgcacg    600
gtcattggcg aaggcggttc cggtggggcc ttagggattg gcgtgggcga tcgcgtcttg    660
atgttaaaaa attccgttta cacagtggcg accccagagg cttgtgccgc cattctctgg    720
aaagatgccg ggaaatcaga gcaggccgcc gccgccctca agattacagc agaggatctg    780
aaaagccttg agattatcga tgaaattgtc ccagagccag cctcctgcgc ccacgccgat    840
cccattgggg ccgcccaact cctgaaagca gcgatccaag ataacctcca agccttgctg    900
aagctgacgc cagaacgccg ccgtgaattg cgctaccagc ggttccggaa aattggtgtg    960
tttttagaaa gttcctaa                                                  978
```

<210> SEQ ID NO 25
<211> LENGTH: 498
<212> TYPE: DNA
<213> ORGANISM: Synechococcus sp. PCC 7002

<400> SEQUENCE: 25

```
atggctatta atttacaaga gatccaagaa cttctatcca ccatcggcca aaccaatgtc     60
accgagtttg aactcaaaac cgatgatttt gaactccgtg tgagcaaagg tactgttgtg    120
gctgctcccc agacgatggt gatgtccgag gcgatcgccc aaccagcaat gtccactccc    180
gttgtttctc aagcaactgc aaccccagaa gcctcccaag cggaaacccc ggctcccagt    240
gtgagcattg atgataagtg ggtcgccatt acctccccca tggtgggaac gttttaccgc    300
gcgccggccc ctggtgaaga tcccttcgtt gccgttggcg atcgcgttgg caatggtcaa    360
accgtttgca tcatcgaagc gatgaaatta atgaatgaga ttgaggcaga agtcagcggt    420
gaagttgtta aaattgccgt tgaagacggt gaacccattg aatttggtca gaccctaatg    480
tgggtcaacc caacctaa                                                  498
```

<210> SEQ ID NO 26
<211> LENGTH: 1347
<212> TYPE: DNA
<213> ORGANISM: Synechococcus sp. PCC 7002

<400> SEQUENCE: 26

```
atgcagtttt caaagattct catcgccaat cgcggagaag ttgccctacg cattatccac     60
acctgtcagg agctcggcat tgccacagtt gccgtccact ccaccgtaga tcgccaagcc    120
ctccacgttc agctcgccga tgagagcatt tgcattggcc cgccccagag cagcaaaagc    180
tatctcaaca ttcccaatat tatcgctgcg gccctcagca gtaacgccga cgcaatccac    240
ccaggctacg gtttcctcgc tgaaaatgcc aagtttgcag aaatttgtgc cgaccaccaa    300
atcaccttca ttggcccttc cccagaagca atgatcgcca tgggggacaa atccaccgcc    360
aaaaaaacga tgcaggcggc aaaagtccct accgtacccg gtagtgctgg gttggtggcc    420
tccgaagaac aagccctaga aatcgcccaa caaattggct accctgtgat gatcaaagcc    480
```

```
acggcgggtg gtggtggccg ggggatgcgc cttgtgccca gcgctgagga gttaccccgt    540

ttgtaccgag cggcccaggg ggaagcagaa gcagcctttg ggaatggcgg cgtttacatc    600

gaaaaattta ttgaacggcc ccgtcacatc gaatttcaga tcctcgcgga tcagtacggc    660

aatgtaattc acctcggcga acgggattgt tcgatccaac ggcggcacca aaaactcctc    720

gaagaagctc ccagcgcgat cctcaccccc agactgcggg acaaaatggg gaaagcggca    780

gtaaaagcgg cgaaatccat tgattatgtc ggggcgggga cggtggaatt cctcgtggat    840

aagaatgggg atttctactt tatggaaatg aatacccgca ttcaggtgga acacccggtc    900

acagagatgg tgacgggact agatctgatc gccgagcaaa ttaaagttgc ccaaggcgat    960

cgcctcagtt tgaatcaaaa tcaagtgaac ttgaatggtc atgccatcga gtgccggatt   1020

aatgccgaag atcccgacca tgatttccga ccgaccccag gcaaaatcag tggctatctt   1080

ccccccggtg gccctggggt acggatggat tcccacgttt acaccgacta tgaaatttct   1140

ccttactacg attctttgat cggtaaatta atcgtttggg gaccagaccg agacaccgcc   1200

attcgccgca tgaagcgggc actccgagaa tgtgccatta ctggagtatc gaccaccatt   1260

agcttccacc aaaagatttt gaatcatccg gctttttgg cggccgatgt cgatacaaac   1320

tttatccagc agcacatgtt gccctag                                       1347
```

```
<210> SEQ ID NO 27
<211> LENGTH: 960
<212> TYPE: DNA
<213> ORGANISM: Synechococcus sp. PCC 7002

<400> SEQUENCE: 27

atgtctcttt ttgattggtt tgccgcaaat cgccaaaatt ctgaaaccca gctccagccc     60

caacaggagc gcgagattgc cgatggcctc tggacgaaat gcaaatcctg cgatgctctc    120

acctacacta aagacctccg caacaatcaa atggtctgta aagagtgtgg cttccataac    180

cgggtcggca gtcgggaacg ggtacgccaa ttgattgacg aaggcacctg gacagaaatt    240

agtcagaatg tcgcgccgac cgaccccctg aaattccgcg acaaaaaagc ctatagcgat    300

cgcctcaaag attaccaaga gaaaacgaac ctcaccgatg ctgtaatcac tggcacagga    360

ctgattgacg gtttacccct tgctttggca gtgatggact ttggctttat gggcggcagc    420

atgggatccg ttgtcggcga aaaaatttgt cgcctcgtag aacatggcac cgccgaaggt    480

ttacccgtgg tggttgtttg tgcttctggt ggagcaagaa tgcaagaggg catgctcagt    540

ctgatgcaga tggcgaaaat ctctggtgcc ctcgaacgcc atcgcaccaa aaaattactc    600

tacatccctg ttttgactaa tcccaccacc gggggcgtca ccgctagctt tgcgatgttg    660

ggcgatttga ttcttgccga acccaaagca accatcggtt ttgctggacg ccgcgtcatt    720

gaacaaacat tgcgcgaaaa acttcctgac gattttcaga catctgaata tttactccaa    780

catgggtttg tggatgcgat tgtgccccgc actgaattga aaaaaaccct cgcccaaatg    840

attagtctcc atcagccctt tcacccgatt ctgccagagc tacaattggc tccccatgtg    900

gaaaaagaaa aagtttacga acccattgcc tctacttcaa ccaacgactt ttacaagtag    960
```

```
<210> SEQ ID NO 28
<211> LENGTH: 2311
<212> TYPE: PRT
<213> ORGANISM: Triticum aestivum

<400> SEQUENCE: 28

Met Gly Ser Thr His Leu Pro Ile Val Gly Leu Asn Ala Ser Thr Thr
```

```
1               5                   10                  15

Pro Ser Leu Ser Thr Ile Arg Pro Val Asn Ser Ala Gly Ala Ala Phe
            20                  25                  30

Gln Pro Ser Ala Pro Ser Arg Thr Ser Lys Lys Lys Ser Arg Arg Val
        35                  40                  45

Gln Ser Leu Arg Asp Gly Gly Asp Gly Gly Val Ser Asp Pro Asn Gln
    50                  55                  60

Ser Ile Arg Gln Gly Leu Ala Gly Ile Ile Asp Leu Pro Lys Glu Gly
65                  70                  75                  80

Thr Ser Ala Pro Glu Val Asp Ile Ser His Gly Ser Glu Glu Pro Arg
                85                  90                  95

Gly Ser Tyr Gln Met Asn Gly Ile Leu Asn Glu Ala His Asn Gly Arg
            100                 105                 110

His Ala Ser Leu Ser Lys Val Val Glu Phe Cys Met Ala Leu Gly Gly
        115                 120                 125

Lys Thr Pro Ile His Ser Val Leu Val Ala Asn Asn Gly Arg Ala Ala
    130                 135                 140

Ala Lys Phe Met Arg Ser Val Arg Thr Trp Ala Asn Glu Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
            180                 185                 190

Pro Gly Gly Thr Asn Asn Asn Asn Tyr Ala Asn Val Gln Leu Ile Val
        195                 200                 205

Glu Ile Ala Val Arg Thr Gly Val Ser Ala Val Trp Pro Gly Trp Gly
    210                 215                 220

His Ala Ser Glu Asn Pro Glu Leu Pro Asp Ala Leu Asn Ala Asn Gly
225                 230                 235                 240

Ile Val Phe Leu Gly Pro Pro Ser Ser Ser Met Asn Ala Leu Gly Asp
                245                 250                 255

Lys Val Gly Ser Ala Leu Ile Ala Gln Ala Ala Gly Val Pro Thr Leu
            260                 265                 270

Pro Trp Gly Gly Ser Gln Val Glu Ile Pro Leu Glu Val Cys Leu Asp
        275                 280                 285

Ser Ile Pro Ala Glu Met Tyr Arg Lys Ala Cys Val Ser Thr Thr Glu
    290                 295                 300

Glu Ala Leu Ala Ser Cys Gln Met Ile Gly Tyr Pro Ala Met Ile Lys
305                 310                 315                 320

Ala Ser Trp Gly Gly Gly Gly Lys Gly Ile Arg Lys Val Asn Asn Asp
                325                 330                 335

Asp Asp Val Arg Ala Leu Phe Lys Gln Val Gln Gly Glu Val Pro Gly
            340                 345                 350

Ser Pro Ile Phe Ile Met Arg Leu Ala Ser Gln Ser Arg His Leu Glu
        355                 360                 365

Val Gln Leu Leu Cys Asp Gln Tyr Gly Asn Val Ala Ala Leu His Ser
    370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Glu Leu Glu Gln Ala
                405                 410                 415

Ala Arg Arg Leu Ala Lys Ala Val Gly Tyr Val Gly Ala Ala Thr Val
            420                 425                 430
```

```
Glu Tyr Leu Tyr Ser Met Glu Thr Gly Glu Tyr Tyr Phe Leu Glu Leu
        435                 440                 445

Asn Pro Arg Leu Gln Val Glu His Pro Val Thr Glu Trp Ile Ala Glu
    450                 455                 460

Val Asn Leu Pro Ala Ala Gln Val Ala Val Gly Met Gly Ile Pro Leu
465                 470                 475                 480

Trp Gln Val Pro Glu Ile Arg Arg Phe Tyr Gly Met Asp Asn Gly Gly
                485                 490                 495

Gly Tyr Asp Ile Trp Arg Glu Thr Ala Ala Leu Ala Thr Pro Phe Asn
            500                 505                 510

Phe Asp Glu Val Asp Ser Gln Trp Pro Lys Gly His Cys Val Ala Val
        515                 520                 525

Arg Ile Thr Ser Glu Asp Pro Asp Asp Gly Phe Lys Pro Thr Gly Gly
    530                 535                 540

Lys Val Lys Glu Ile Ser Phe Lys Ser Lys Pro Asn Val Trp Ala Tyr
545                 550                 555                 560

Phe Ser Val Lys Ser Gly Gly Gly Ile His Glu Phe Ala Asp Ser Gln
                565                 570                 575

Phe Gly His Val Phe Ala Tyr Gly Val Ser Arg Ala Ala Ala Ile Thr
            580                 585                 590

Asn Met Ser Leu Ala Leu Lys Glu Ile Gln Ile Arg Gly Glu Ile His
        595                 600                 605

Ser Asn Val Asp Tyr Thr Val Asp Leu Leu Asn Ala Ser Asp Phe Lys
    610                 615                 620

Glu Asn Arg Ile His Thr Gly Trp Leu Asp Asn Arg Ile Ala Met Arg
625                 630                 635                 640

Val Gln Ala Glu Arg Pro Pro Trp Tyr Ile Ser Val Val Gly Gly Ala
                645                 650                 655

Leu Tyr Lys Thr Ile Thr Ser Asn Thr Asp Thr Val Ser Glu Tyr Val
            660                 665                 670

Ser Tyr Leu Val Lys Gly Gln Ile Pro Pro Lys His Ile Ser Leu Val
        675                 680                 685

His Ser Thr Val Ser Leu Asn Ile Glu Glu Ser Lys Tyr Thr Ile Glu
    690                 695                 700

Thr Ile Arg Ser Gly Gln Gly Ser Tyr Arg Leu Arg Met Asn Gly Ser
705                 710                 715                 720

Val Ile Glu Ala Asn Val Gln Thr Leu Cys Asp Gly Gly Leu Leu Met
                725                 730                 735

Gln Leu Asp Gly Asn Ser His Val Ile Tyr Ala Glu Glu Glu Ala Gly
            740                 745                 750

Gly Thr Arg Leu Leu Ile Asp Gly Lys Thr Tyr Leu Leu Gln Asn Asp
        755                 760                 765

His Asp Pro Ser Arg Leu Leu Ala Glu Thr Pro Cys Lys Leu Leu Arg
    770                 775                 780

Phe Leu Val Ala Asp Gly Ala His Val Glu Ala Asp Val Pro Tyr Ala
785                 790                 795                 800

Glu Val Glu Val Met Lys Met Cys Met Pro Leu Leu Ser Pro Ala Ala
                805                 810                 815

Gly Val Ile Asn Val Leu Leu Ser Glu Gly Gln Pro Met Gln Ala Gly
            820                 825                 830

Asp Leu Ile Ala Arg Leu Asp Leu Asp Asp Pro Ser Ala Val Lys Arg
        835                 840                 845
```

```
Ala Glu Pro Phe Asn Gly Ser Phe Pro Glu Met Ser Leu Pro Ile Ala
    850                 855                 860

Ala Ser Gly Gln Val His Lys Arg Cys Ala Thr Ser Leu Asn Ala Ala
865                 870                 875                 880

Arg Met Val Leu Ala Gly Tyr Asp His Pro Ile Asn Lys Val Val Gln
                885                 890                 895

Asp Leu Val Ser Cys Leu Asp Ala Pro Glu Leu Pro Phe Leu Gln Trp
            900                 905                 910

Glu Glu Leu Met Ser Val Leu Ala Thr Arg Leu Pro Arg Leu Leu Lys
        915                 920                 925

Ser Glu Leu Glu Gly Lys Tyr Ser Glu Tyr Lys Leu Asn Val Gly His
    930                 935                 940

Gly Lys Ser Lys Asp Phe Pro Ser Lys Met Leu Arg Glu Ile Ile Glu
945                 950                 955                 960

Glu Asn Leu Ala His Gly Ser Glu Lys Glu Ile Ala Thr Asn Glu Arg
                965                 970                 975

Leu Val Glu Pro Leu Met Ser Leu Leu Lys Ser Tyr Glu Gly Gly Arg
            980                 985                 990

Glu Ser His Ala His Phe Ile Val Lys Ser Leu Phe Glu Asp Tyr Leu
        995                 1000                1005

Ser Val Glu Glu Leu Phe Ser Asp Gly Ile Gln Ser Asp Val Ile Glu
    1010                1015                1020

Arg Leu Arg Gln Gln His Ser Lys Asp Leu Gln Lys Val Val Asp Ile
1025                1030                1035                1040

Val Leu Ser His Gln Gly Val Arg Asn Lys Thr Lys Leu Ile Leu Thr
                1045                1050                1055

Leu Met Glu Lys Leu Val Tyr Pro Asn Pro Ala Val Tyr Lys Asp Gln
            1060                1065                1070

Leu Thr Arg Phe Ser Ser Leu Asn His Lys Arg Tyr Tyr Lys Leu Ala
        1075                1080                1085

Leu Lys Ala Ser Glu Leu Leu Glu Gln Thr Lys Leu Ser Glu Leu Arg
    1090                1095                1100

Thr Ser Ile Ala Arg Ser Leu Ser Glu Leu Glu Met Phe Thr Glu Glu
1105                1110                1115                1120

Arg Thr Ala Ile Ser Glu Ile Met Gly Asp Leu Val Thr Ala Pro Leu
                1125                1130                1135

Pro Val Glu Asp Ala Leu Val Ser Leu Phe Asp Cys Ser Asp Gln Thr
            1140                1145                1150

Leu Gln Gln Arg Val Ile Glu Thr Tyr Ile Ser Arg Leu Tyr Gln Pro
        1155                1160                1165

His Leu Val Lys Asp Ser Ile Gln Leu Lys Tyr Gln Glu Ser Gly Val
    1170                1175                1180

Ile Ala Leu Trp Glu Phe Ala Glu Ala His Ser Glu Lys Arg Leu Gly
1185                1190                1195                1200

Ala Met Val Ile Val Lys Ser Leu Glu Ser Val Ser Ala Ala Ile Gly
                1205                1210                1215

Ala Ala Leu Lys Gly Thr Ser Arg Tyr Ala Ser Ser Glu Gly Asn Ile
            1220                1225                1230

Met His Ile Ala Leu Leu Gly Ala Asp Asn Gln Met His Gly Thr Glu
        1235                1240                1245

Asp Ser Gly Asp Asn Asp Gln Ala Gln Val Arg Ile Asp Lys Leu Ser
    1250                1255                1260

Ala Thr Leu Glu Gln Asn Thr Val Thr Ala Asp Leu Arg Ala Ala Gly
```

```
1265                1270                1275                1280

Val Lys Val Ile Ser Cys Ile Val Gln Arg Asp Gly Ala Leu Met Pro
                1285                1290                1295

Met Arg His Thr Phe Leu Leu Ser Asp Glu Lys Leu Cys Tyr Gly Glu
            1300                1305                1310

Glu Pro Val Leu Arg His Val Glu Pro Pro Leu Ser Ala Leu Leu Glu
        1315                1320                1325

Leu Gly Lys Leu Lys Val Lys Gly Tyr Asn Glu Val Lys Tyr Thr Pro
    1330                1335                1340

Ser Arg Asp Arg Gln Trp Asn Ile Tyr Thr Leu Arg Asn Thr Glu Asn
1345                1350                1355                1360

Pro Lys Met Leu His Arg Val Phe Phe Arg Thr Leu Val Arg Gln Pro
                1365                1370                1375

Gly Ala Ser Asn Lys Phe Thr Ser Gly Asn Ile Ser Asp Val Glu Val
            1380                1385                1390

Gly Gly Ala Glu Glu Ser Leu Ser Phe Thr Ser Ser Ser Ile Leu Arg
        1395                1400                1405

Ser Leu Met Thr Ala Ile Glu Glu Leu Glu Leu His Ala Ile Arg Thr
    1410                1415                1420

Gly His Ser His Met Phe Leu Cys Ile Leu Lys Glu Arg Lys Leu Leu
1425                1430                1435                1440

Asp Leu Val Pro Val Ser Gly Asn Lys Val Val Asp Ile Gly Gln Asp
                1445                1450                1455

Glu Ala Thr Ala Cys Leu Leu Leu Lys Glu Met Ala Leu Gln Ile His
            1460                1465                1470

Glu Leu Val Gly Ala Arg Met His His Leu Ser Val Cys Gln Trp Glu
        1475                1480                1485

Val Lys Leu Lys Leu Asp Ser Asp Gly Pro Ala Ser Gly Thr Trp Arg
    1490                1495                1500

Val Val Thr Thr Asn Val Thr Ser His Thr Cys Thr Val Asp Ile Tyr
1505                1510                1515                1520

Arg Glu Val Glu Asp Thr Glu Ser Gln Lys Leu Val Tyr His Ser Ala
                1525                1530                1535

Pro Ser Ser Ser Gly Pro Leu His Gly Val Ala Leu Asn Thr Pro Tyr
            1540                1545                1550

Gln Pro Leu Ser Val Ile Asp Leu Lys Arg Cys Ser Ala Arg Asn Asn
        1555                1560                1565

Arg Thr Thr Tyr Cys Tyr Asp Phe Pro Leu Ala Phe Glu Thr Ala Val
    1570                1575                1580

Gln Lys Ser Trp Ser Asn Ile Ser Ser Asp Asn Asn Arg Cys Tyr Val
1585                1590                1595                1600

Lys Ala Thr Glu Leu Val Phe Ala His Lys Asn Gly Ser Trp Gly Thr
                1605                1610                1615

Pro Val Ile Pro Met Glu Arg Pro Ala Gly Leu Asn Asp Ile Gly Met
            1620                1625                1630

Val Ala Trp Ile Leu Asp Met Ser Thr Pro Glu Tyr Pro Asn Gly Arg
        1635                1640                1645

Gln Ile Val Val Ile Ala Asn Asp Ile Thr Phe Arg Ala Gly Ser Phe
    1650                1655                1660

Gly Pro Arg Glu Asp Ala Phe Phe Glu Thr Val Thr Asn Leu Ala Cys
1665                1670                1675                1680

Glu Arg Arg Leu Pro Leu Ile Tyr Leu Ala Ala Asn Ser Gly Ala Arg
                1685                1690                1695
```

```
Ile Gly Ile Ala Asp Glu Val Lys Ser Cys Phe Arg Val Gly Trp Ser
            1700                1705                1710

Asp Asp Gly Ser Pro Glu Arg Gly Phe Gln Tyr Ile Tyr Leu Thr Glu
        1715                1720                1725

Glu Asp His Ala Arg Ile Ser Ala Ser Val Ile Ala His Lys Met Gln
    1730                1735                1740

Leu Asp Asn Gly Glu Ile Arg Trp Val Ile Asp Ser Val Val Gly Lys
1745                1750                1755                1760

Glu Asp Gly Leu Gly Val Glu Asn Ile His Gly Ser Ala Ala Ile Ala
                1765                1770                1775

Ser Ala Tyr Ser Arg Ala Tyr Glu Glu Thr Phe Thr Leu Thr Phe Val
            1780                1785                1790

Thr Gly Arg Thr Val Gly Ile Gly Ala Tyr Leu Ala Arg Leu Gly Ile
        1795                1800                1805

Arg Cys Ile Gln Arg Thr Asp Gln Pro Ile Ile Leu Thr Gly Phe Ser
    1810                1815                1820

Ala Leu Asn Lys Leu Leu Gly Arg Glu Val Tyr Ser Ser His Met Gln
1825                1830                1835                1840

Leu Gly Gly Pro Lys Ile Met Ala Thr Asn Gly Val Val His Leu Thr
                1845                1850                1855

Val Ser Asp Asp Leu Glu Gly Val Ser Asn Ile Leu Arg Trp Leu Ser
            1860                1865                1870

Tyr Val Pro Ala Asn Ile Gly Gly Pro Leu Pro Ile Thr Lys Ser Leu
        1875                1880                1885

Asp Pro Pro Asp Arg Pro Val Ala Tyr Ile Pro Glu Asn Thr Cys Asp
    1890                1895                1900

Pro Arg Ala Ala Ile Ser Gly Ile Asp Asp Ser Gln Gly Lys Trp Leu
1905                1910                1915                1920

Gly Gly Met Phe Asp Lys Asp Ser Phe Val Glu Thr Phe Glu Gly Trp
                1925                1930                1935

Ala Lys Ser Val Val Thr Gly Arg Ala Lys Leu Gly Gly Ile Pro Val
            1940                1945                1950

Gly Val Ile Ala Val Glu Thr Gln Thr Met Met Gln Leu Ile Pro Ala
        1955                1960                1965

Asp Pro Gly Gln Leu Asp Ser His Glu Arg Ser Val Pro Arg Ala Gly
    1970                1975                1980

Gln Val Trp Phe Pro Asp Ser Ala Thr Lys Thr Ala Gln Ala Met Leu
1985                1990                1995                2000

Asp Phe Asn Arg Glu Gly Leu Pro Leu Phe Ile Leu Ala Asn Trp Arg
                2005                2010                2015

Gly Phe Ser Gly Gly Gln Arg Asp Leu Phe Glu Gly Ile Leu Gln Ala
            2020                2025                2030

Gly Ser Thr Ile Val Glu Asn Leu Arg Ala Tyr Asn Gln Pro Ala Phe
        2035                2040                2045

Val Tyr Ile Pro Lys Ala Ala Glu Leu Arg Gly Gly Ala Trp Val Val
    2050                2055                2060

Ile Asp Ser Lys Ile Asn Pro Asp Arg Ile Glu Phe Tyr Ala Glu Arg
2065                2070                2075                2080

Thr Ala Lys Gly Asn Val Leu Glu Pro Gln Gly Leu Ile Glu Ile Lys
                2085                2090                2095

Phe Arg Ser Glu Glu Leu Gln Glu Cys Met Gly Arg Leu Asp Pro Glu
            2100                2105                2110
```

```
Leu Ile Asn Leu Lys Ala Lys Leu Gln Gly Val Lys His Glu Asn Gly
        2115                2120                2125

Ser Leu Pro Glu Ser Glu Ser Leu Gln Lys Ser Ile Glu Ala Arg Lys
    2130                2135                2140

Lys Gln Leu Leu Pro Leu Tyr Thr Gln Ile Ala Val Arg Phe Ala Glu
2145                2150                2155                2160

Leu His Asp Thr Ser Leu Arg Met Ala Ala Lys Gly Val Ile Lys Lys
                2165                2170                2175

Val Val Asp Trp Glu Asp Ser Arg Ser Phe Phe Tyr Lys Arg Leu Arg
            2180                2185                2190

Arg Arg Ile Ser Glu Asp Val Leu Ala Lys Glu Ile Arg Gly Val Ser
        2195                2200                2205

Gly Lys Gln Phe Ser His Gln Ser Ala Ile Glu Leu Ile Gln Lys Trp
    2210                2215                2220

Tyr Leu Ala Ser Lys Gly Ala Glu Thr Gly Ser Thr Glu Trp Asp Asp
2225                2230                2235                2240

Asp Asp Ala Phe Val Ala Trp Arg Glu Asn Pro Glu Asn Tyr Gln Glu
                2245                2250                2255

Tyr Ile Lys Glu Pro Arg Ala Gln Arg Val Ser Gln Leu Leu Ser Asp
            2260                2265                2270

Val Ala Asp Ser Ser Pro Asp Leu Glu Ala Leu Pro Gln Gly Leu Ser
        2275                2280                2285

Met Leu Leu Glu Lys Met Asp Pro Ala Lys Arg Glu Ile Val Glu Asp
    2290                2295                2300

Phe Glu Ile Asn Leu Val Lys
2305                2310


<210> SEQ ID NO 29
<211> LENGTH: 6936
<212> TYPE: DNA
<213> ORGANISM: Triticum aestivum

<400> SEQUENCE: 29

atgggatcca cacatttgcc cattgtcggc cttaatgcct cgacaacacc atcgctatcc      60

actattcgcc cggtaaattc agccggtgct gcattccaac catctgcccc ttctagaacc     120

tccaagaaga aaagtcgtcg tgttcagtca ttaagggatg gaggcgatgg aggcgtgtca     180

gaccctaacc agtctattcg ccaaggtctt gccggcatca ttgacctccc aaaggagggc     240

acatcagctc cggaagtgga tatttcacat gggtccgaag aacccagggg ctcctaccaa     300

atgaatggga tactgaatga agcacataat gggaggcatg cttcgctgtc taaggttgtc     360

gaattttgta tggcattggg cggcaaaaca ccaattcaca gtgtattagt tgcgaacaat     420

ggaagggcag cagctaagtt catgcggagt gtccgaacat gggctaatga aacatttggg     480

tcagagaagg caattcagtt gatagctatg gctactccag aagacatgag gataaatgca     540

gagcacatta gaattgctga tcaatttgtt gaagtacccg gtggaacaaa caataacaac     600

tatgcaaatg tccaactcat agtggagata gcagtgagaa ccggtgtttc tgctgtttgg     660

cctggttggg gccatgcatc tgagaatcct gaacttccag atgcactaaa tgcaaacgga     720

attgtttttc ttgggccacc atcatcatca atgaacgcac taggtgacaa ggttggttca     780

gctctcattg ctcaagcagc aggggttccg actcttcctt ggggtggatc acaggtggaa     840

attccattag aagtttgttt ggactcgata cctgcggaga tgtataggaa agcttgtgtt     900

agtactacgg aggaagcact tgcgagttgt cagatgattg ggtatccagc catgattaaa     960
```

```
gcatcatggg gtggtggtgg taaagggatc cgaaaggtta ataacgacga tgatgtcaga   1020
gcactgttta agcaagtgca aggtgaagtt cctggctccc caatatttat catgagactt   1080
gcatctcaga gtcgacatct tgaagttcag ttgctttgtg atcaatatgg caatgtagct   1140
gcgcttcaca gtcgtgactg cagtgtgcaa cggcgacacc aaaagattat tgaggaagga   1200
ccagttactg ttgctcctcg cgagacagtg aaagagctag agcaagcagc aaggaggctt   1260
gctaaggctg tgggttatgt tggtgctgct actgttgaat atctctacag catggagact   1320
ggtgaatact attttctgga acttaatcca cggttgcagg ttgagcatcc agtcaccgag   1380
tggatagctg aagtaaactt gcctgcagct caagttgcag ttggaatggg tatacccctt   1440
tggcaggttc cagagatcag acgtttctat ggaatggaca atggaggagg ctatgacatt   1500
tggagggaaa cagcagctct tgctactcca tttaacttcg atgaagtgga ttctcaatgg   1560
ccaaagggtc attgtgtagc agttaggata accagtgagg atccagatga cggattcaag   1620
cctaccggtg gaaaagtaaa ggagatcagt tttaaaagca agccaaatgt ttgggcctat   1680
ttctctgtta agtccggtgg aggcattcat gaatttgctg attctcagtt tggacatgtt   1740
tttgcatatg gagtgtctag agcagcagca ataaccaaca tgtctcttgc gctaaaagag   1800
attcaaattc gtggagaaat tcattcaaat gttgattaca cagttgatct cttgaatgcc   1860
tcagacttca aagaaaacag gattcatact ggctggctgg ataacagaat agcaatgcga   1920
gtccaagctg agagacctcc gtggtatatt tcagtggttg gaggagctct atataaaaca   1980
ataacgagca acacagacac tgtttctgaa tatgttagct atctcgtcaa gggtcagatt   2040
ccaccgaagc atatatccct tgtccattca actgtttctt tgaatataga ggaaagcaaa   2100
tatacaattg aaactataag gagcggacag ggtagctaca gattgcgaat gaatggatca   2160
gttattgaag caaatgtcca aacattatgt gatggtggac ttttaatgca gttggatgga   2220
aacagccatg taatttatgc tgaagaagag gccggtggta cacggcttct aattgatgga   2280
aagacatact tgttacagaa tgatcacgat ccttcaaggt tattagctga gacaccctgc   2340
aaacttcttc gtttcttggt tgccgatggt gctcatgttg aagctgatgt accatatgcg   2400
gaagttgagg ttatgaagat gtgcatgccc ctcttgtcac ctgctgctgg tgtcattaat   2460
gttttgttgt ctgagggcca gcctatgcag gctggtgatc ttatagcaag acttgatctt   2520
gatgaccctt ctgctgtgaa gagagctgag ccatttaacg gatctttccc agaaatgagc   2580
cttcctattg ctgcttctgg ccaagttcac aaaagatgtg ccacaagctt gaatgctgct   2640
cggatggtcc ttgcaggata tgatcacccg atcaacaaag ttgtacaaga tctggtatcc   2700
tgtctagatg ctcctgagct tcctttccta caatgggaag agcttatgtc tgttttagca   2760
actagacttc caaggcttct taagagcgag ttggagggta aatacagtga atataagtta   2820
aatgttggcc atgggaagag caaggatttc ccttccaaga tgctaagaga gataatcgag   2880
gaaaatcttg cacatggttc tgagaaggaa attgctacaa atgagaggct tgttgagcct   2940
cttatgagcc tactgaagtc atatgagggt ggcagagaaa gccatgcaca ctttattgtg   3000
aagtcccttt tcgaggacta tctctcggtt gaggaactat tcagtgatgg cattcagtct   3060
gatgtgattg aacgcctgcg ccaacaacat agtaaagatc tccagaaggt tgtagacatt   3120
gtgttgtctc accagggtgt gagaaacaaa actaagctga tactaacact catggagaaa   3180
ctggtctatc caaaccctgc tgtctacaag gatcagttga ctcgcttttc ctccctcaat   3240
cacaaaagat attataagtt ggcccttaaa gctagcgagc ttcttgaaca aaccaagctt   3300
agtgagctcc gcacaagcat tgcaaggagc ctttcagaac ttgagatgtt tactgaagaa   3360
```

-continued aggacggcca ttagtgagat catgggagat ttagtgactg ccccactgcc agttgaagat 3420
gcactggttt ctttgtttga ttgtagtgat caaactcttc agcagagggt gatcgagacg 3480
tacatatctc gattatacca gcctcatctt gtcaaggata gtatccagct gaaatatcag 3540
gaatctggtg ttattgcttt atgggaattc gctgaagcgc attcagagaa gagattgggt 3600
gctatggtta ttgtgaagtc gttagaatct gtatcagcag caattggagc tgcactaaag 3660
ggtacatcac gctatgcaag ctctgagggt aacataatgc atattgcttt attgggtgct 3720
gataatcaaa tgcatggaac tgaagacagt ggtgataacg atcaagctca agtcaggata 3780
gacaaacttt ctgcgacact ggaacaaaat actgtcacag ctgatctccg tgctgctggt 3840
gtgaaggtta ttagttgcat tgttcaaagg gatggagcac tcatgcctat gcgccatacc 3900
ttcctcttgt cggatgaaaa gctttgttat ggggaagagc cggttctccg gcatgtggag 3960
cctcctcttt ctgctcttct tgagttgggt aagttgaaag tgaaaggata caatgaggtg 4020
aagtatacac cgtcacgtga tcgtcagtgg aacatataca cacttagaaa tacagagaac 4080
cccaaaatgt tgcacagggt gtttttccga actcttgtca ggcaacccgg tgcttccaac 4140
aaattcacat caggcaacat cagtgatgtt gaagtgggag gagctgagga atctctttca 4200
tttacatcga gcagcatatt aagatcgctg atgactgcta tagaagagtt ggagcttcac 4260
gcgattagga caggtcactc tcatatgttt ttgtgcatat tgaaagagcg aaagcttctt 4320
gatcttgttc ccgtttcagg gaacaaagtt gtggatattg gccaagatga agctactgca 4380
tgcttgcttc tgaaagaaat ggctctacag atacatgaac ttgtgggtgc aaggatgcat 4440
catctttctg tatgccaatg ggaggtgaaa cttaagttgg acagcgatgg gcctgccagt 4500
ggtacctgga gagttgtaac aaccaatgtt actagtcaca cctgcactgt ggatatctac 4560
cgtgaggttg aagatacaga atcacagaaa ctagtatacc actctgctcc atcgtcatct 4620
ggtcctttgc atggcgttgc actgaatact ccatatcagc ctttgagtgt tattgatctg 4680
aaacgttgct ccgctagaaa caacagaact acatactgct atgattttcc gttggcattt 4740
gaaactgcag tgcagaagtc atggtctaac atttctagtg acaataaccg atgttatgtt 4800
aaagcaacgg agctggtgtt tgctcacaag aatgggtcat ggggcactcc tgtaattcct 4860
atggagcgtc ctgctgggct caatgacatt ggtatggtag cttggatctt ggacatgtcc 4920
actcctgaat atcccaatgg caggcagatt gttgtcatcg caaatgatat tacttttaga 4980
gctggatcgt ttggtccaag ggaagatgca ttttttgaaa ctgttaccaa cctagcttgt 5040
gagaggaggc ttcctctcat ctacttggca gcaaactctg gtgctcggat cggcatagca 5100
gatgaagtaa aatcttgctt ccgtgttgga tggtctgatg atggcagccc tgaacgtggg 5160
tttcaatata tttatctgac tgaagaagac catgctcgta ttagcgcttc tgttatagcg 5220
cacaagatgc agcttgataa tggtgaaatt aggtgggtta ttgattctgt tgtagggaag 5280
gaggatgggc taggtgtgga gaacatacat ggaagtgctg ctattgccag tgcctattct 5340
agggcctatg aggagacatt tacgcttaca tttgtgactg gaaggactgt tggaatagga 5400
gcatatcttg ctcgacttgg catacggtgc attcagcgta ctgaccagcc cattatccta 5460
actgggtttt ctgccttgaa caagcttctt ggccgggaag tgtacagctc ccacatgcag 5520
ttgggtggcc ccaaaattat ggcgacaaac ggtgttgtcc atctgacagt ttcagatgac 5580
cttgaaggtg tatctaatat attgaggtgg ctcagctatg ttcctgccaa cattggtgga 5640
cctcttccta ttacaaaatc tttggaccca cctgacagac ccgttgctta catccctgag 5700

-continued

```
aatacatgcg atcctcgtgc tgccatcagt ggcattgatg atagccaagg gaaatggttg   5760

gggggcatgt tcgacaaaga cagttttgtg gagacatttg aaggatgggc gaagtcagtt   5820

gttactggca gagcgaaact cggagggatt ccggtgggtg ttatagctgt ggagacacag   5880

actatgatgc agctcatccc tgctgatcca ggccagcttg attcccatga gcgatctgtt   5940

cctcgtgctg ggcaagtctg gtttccagat tcagctacta agacagcgca ggcaatgctg   6000

gacttcaacc gtgaaggatt acctctgttc atccttgcta actggagagg cttctctggt   6060

ggacaaagag atctttttga aggaatcctt caggctgggt caacaattgt tgagaacctt   6120

agggcataca atcagcctgc ctttgtatat atccccaagg ctgcagagct acgtggaggg   6180

gcttgggtcg tgattgatag caagataaat ccagatcgca ttgagttcta tgctgagagg   6240

actgcaaagg gcaatgttct cgaacctcaa gggttgatcg agatcaagtt caggtcagag   6300

gaactccaag agtgcatggg taggcttgat ccagaattga taaatctgaa ggcaaagctc   6360

cagggagtaa agcatgaaaa tggaagtcta cctgagtcag aatcccttca gaagagcata   6420

gaagcccgga agaaacagtt gttgcctttg tatactcaaa ttgcggtacg gttcgctgaa   6480

ttgcatgaca cttcccttag aatggctgct aagggtgtga ttaagaaggt tgtagactgg   6540

gaagattcta ggtcgttctt ctacaagaga ttacggagga ggatatccga ggatgttctt   6600

gcgaaggaaa ttagaggtgt aagtggcaag cagttttctc accaatcggc aatcgagctg   6660

atccagaaat ggtacttggc ctctaaggga gctgaaacag gaagcactga atgggatgat   6720

gacgatgctt ttgttgcctg gagggaaaac cctgaaaact accaggagta tatcaaagaa   6780

cccagggctc aaagggtatc tcagttgctc tcagatgttg cagactccag tccagatcta   6840

gaagccttgc cacagggtct ttctatgcta ctagagaaga tggatcctgc aaagagggaa   6900

attgttgaag actttgaaat aaaccttgta aagtaa                             6936


<210> SEQ ID NO 30
<211> LENGTH: 5
<212> TYPE: PRT
<213> ORGANISM: Artificial Sequence
<220> FEATURE:
<223> OTHER INFORMATION: PAP1 enzyme catalytic motif
<220> FEATURE:
<221> NAME/KEY: VARIANT
<222> LOCATION: 2, 4
<223> OTHER INFORMATION: Xaa = Any Amino Acid

<400> SEQUENCE: 30

Asp Xaa Asp Xaa Thr
 1               5
```

MODIFIED PHOTOSYNTHETIC MICROORGANISMS FOR PRODUCING TRIGLYCERIDES

CROSS-REFERENCE TO RELATED APPLICATION

This application is a continuation of U.S. Utility patent application Ser. No. 12/605,204 filed Oct. 23, 2009, where this utility application is incorporated herein by reference in its entirety and claims the benefit 35 U.S.C. §119(e) of U.S. Provisional Patent Application No. 61/107,979 filed Oct. 23, 2008

This application claims the benefit under 35 U.S.C. §119 (e) of U.S. Provisional Patent Application No. 61/107,979 filed Oct. 23, 2008, where this provisional application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 890071_401_SEQUENCE_LISTING.txt. The text file is 115 KB, was created on Oct. 23, 2009 and is being submitted electronically via EFS-Web.

BACKGROUND

1. Technical Field

The present invention relates generally to genetically modified photosynthetic microorganisms, including Cyanobacteria, capable of synthesizing triglycerides, which may be used as a feedstock for producing biofuels and other specialty chemicals.

2. Description of the Related Art

Triglycerides are neutral polar molecules consisting of glycerol esterified with three fatty acid molecules. Triglycerides are utilized as carbon and energy storage molecules by most eukaryotic organisms, including plants and algae, and by certain prokaryotic organisms, including certain species of actinomycetes and members of the genus *Acinetobacter.*

Triglycerides may also be utilized as a feedstock in the production of biofuels and/or various specialty chemicals. For example, triglycerides may be subject to a transesterification reaction, in which an alcohol reacts with triglyceride oils, such as those contained in vegetable oils, animal fats, recycled greases, to produce biodiesels such as fatty acid alkyl esters. Such reactions also produce glycerin as a by-product, which can be purified for use in the pharmaceutical and cosmetic industries Certain organisms can be utilized as a source of triglycerides in the production of biofuels. For example, algae naturally produce triglycerides as energy storage molecules, and certain biofuel-related technologies are presently focused on the use of algae as a feedstock for biofuels. Algae are photosynthetic organisms, and the use of triglyceride-producing organisms such as algae provides the ability to produce biodiesel from sunlight, water, $CO_2$, macronutrients, and micronutrients. Algae, however, cannot be readily genetically manipulated, and produce much less oil (i.e., triglycerides) under culture conditions than in the wild.

Like algae, Cyanobacteria obtain energy from photosynthesis, utilizing chlorophyll A and water to reduce $CO_2$. Certain Cyanobacteria can produce metabolites, such as carbohydrates, proteins, and fatty acids, from just sunlight, water $CO_2$, water, and inorganic salts. Unlike algae, Cyanobacteria can be genetically manipulated. For example, *S. elongatus* PCC 7942 (hereafter referred to as "*S. elongatus* PCC 7942") is a genetically manipulable, oligotrophic Cyanobacterium that thrives in low nutrient level conditions, and in the wild accumulates fatty acids in the form of lipid membranes to about 4 to 8% by dry weight. Cyanobacteria such as *Synechococcus*, however, produce no triglyceride energy storage molecules, since Cyanobacteria typically lack the essential enzymes involved in triglyceride synthesis.

Clearly, therefore, there is a need in the art for modified photosynthetic microorganisms, including Cyanobacteria, capable of producing triglycerides, e.g., to be used as feedstock in the production of biofuels and/or various specialty chemicals.

BRIEF SUMMARY

Embodiments of the present invention relate to the demonstration that photosynthetic microorganisms, including Cyanobacteria, can be genetically modified to increase fatty acid biosynthesis, and to produce triglycerides from their natural-occurring fatty acids. Generally, the modified photosynthetic microorganisms, e.g., Cyanobacteria, of the present invention comprise one or more polynucleotides encoding one or more enzymes associated with triglyceride biosynthesis and/or fatty acid synthesis.

Embodiments of the present invention include methods of producing triglycerides in a photosynthetic microorganism, e.g., a Cyanobacterium, comprising introducing one or more polynucleotides encoding one or more enzymes associated with triglyceride biosynthesis into a photosynthetic microorganism, e.g., a Cyanobacterium. In certain aspects, the one or more enzymes comprise diacylglycerol acyltransferase (DGAT) and/or phosphatidate phosphatase.

In certain embodiments of the methods and compositions of the present invention, the DGAT is an *Acinetobacter* DGAT or a variant thereof. In certain embodiments, the *Acinetobacter* DGAT is *Acinetobacter baylii* ADP1 diacylglycerol acyltransferase (AtfA). Other DGATs that may be used according to the present invention include, but are not limited to, *Streptomyces coelicolor* DGAT, *Alcanivorax borkumensis* DGAT, or the modified DGATs described herein.

In certain embodiments of the methods and compositions of the present invention, said phosphatidate phosphatase is a yeast phosphatidate phosphatase. In certain aspects, said yeast phosphatidate phosphatase is *Saccharomyces cerevisiae* phosphatidate phosphatase (yPah1). However, other phosphatidate phosphatases, including but not limited to those described herein, may also be used.

In certain embodiments of the methods and compositions of the present invention, said one or more enzymes comprise acetyl-CoA carboxylase (ACCase), optionally in combination with diacylglycerol acyltransferase (DGAT) and/or phosphatidate phosphatase. In particular embodiments, the ACCase is a *Saccharomyces cerevisiae* ACCase, a *Triticum aestivum* ACCase, or a *Synechococcus* sp. PCC 7002 ACCAse, including, but not limited to, any of those described herein.

In various embodiments of the present invention, said one or more polynucleotides are codon-optimized for expression in a photosynthetic microorganism, e.g., a Cyanobacterium.

Certain embodiments include methods of increasing fatty acid production by a photosynthetic microorganism, e.g., a Cyanobacterium, comprising introducing one or more polynucleotides encoding one or more enzymes associated with fatty acid biosynthesis into a photosynthetic microorganism, e.g., a Cyanobacterium. In certain aspects, said one or more enzymes comprise acetyl-CoA carboxylase (ACCase). In certain aspects, said ACCase is a yeast ACCase or a derivative thereof. In certain aspects, said ACCase is *Saccharomyces cerevisiae* acetyl-CoA carboxylase (yACC1), a *Triticum aestivum* ACCase, or a *Synechococcus* sp. PCC 7002 ACCAse, including, but not limited to, any of those described herein. In certain aspects, said one or more enzymes further comprise diacylglycerol acyltransferase (DGAT) and phosphatidate phosphatase. In certain embodiments, the DGAT is an *Acinetobacter* DGAT or a variant thereof, including wherein said DGAT is *Acinetobacter baylii* ADP1 diacylglycerol acyltransferase (AtfA). Other DGATs that may be used according to the present invention include, but are not limited to, *Streptomyces coelicolor* DGAT, *Alcanivorax borkumensis* DGAT, or the modified DGATs described herein. In certain aspects, said phosphatidate phosphatase is a yeast phosphatidate phosphatase, such as a *Saccharomyces cerevisiae* phosphatidate phosphatase (yPah1). In certain embodiments, said one or more enzymes comprise acetyl-CoA carboxylase (ACCase) and diacylglycerol acyltransferase (DGAT). In certain embodiments, said one or more enzymes comprise acetyl-CoA carboxylase (ACCase) and phosphatidate phosphatase. In certain embodiments, said one or more enzymes comprise acetyl-CoA carboxylase (ACCase), diacylglycerol acyltransferase (DGAT), and phosphatidate phosphatase. In certain aspects, the one or more polynucleotides are codon-optimized for expression in a photosynthetic microorganism, e.g., a Cyanobacterium.

Certain embodiments include methods of producing a triglyceride in a photosynthetic microorganism, e.g., a Cyanobacterium, comprising culturing a Cyanobacterium comprising one or more polynucleotides encoding one or more enzymes associated with triglyceride biosynthesis. In certain embodiments, said one or more enzymes comprise diacylglycerol acyltransferase (DGAT) and/or phosphatidate phosphatase. In certain aspects, said DGAT is an *Acinetobacter* DGAT or a variant thereof, including wherein said *Acinetobacter* DGAT is *Acinetobacter baylii* ADP1 diacylglycerol acyltransferase (AtfA). Other DGATs that may be used according to the present invention include, but are not limited to, *Streptomyces coelicolor* DGAT, *Alcanovorax borkumensis* DGAT, or the modified DGATs described herein. In certain aspects, said phosphatidate phosphatase is a yeast phosphatidate phosphatase, including wherein said yeast phosphatidate phosphatase is *Saccharomyces cerevisiae* phosphatidate phosphatase (yPah1). In certain embodiments, said one or more enzymes comprise acetyl-CoA carboxylase (ACCase), alone or in combination with diacylglycerol acyltransferase (DGAT) and/or phosphatidate phosphatase.

Certain embodiments of the present invention include methods of producing an increased amount of fatty acid in a photosynthetic microorganism, e.g., a Cyanobacterium, comprising culturing a photosynthetic microorganism, e.g., Cyanobacterium comprising one or more polynucleotides encoding one or more enzymes associated with fatty acid biosynthesis, wherein said polynucleotides are exogenous to the photosynthetic microorganism's native genome. In certain embodiments, said one or more enzymes comprise acetyl-CoA carboxylase (ACCase). In certain aspects, said ACCase is a yeast ACCase or a variant thereof, such as wherein said yeast ACCase is *Saccharomyces cerevisiae* acetyl-CoA carboxylase (yACC1). In certain embodiments, said one or more enzymes comprise diacylglycerol acyltransferase (DGAT) and/or phosphatidate phosphatase. In certain aspects, said DGAT is an *Acinetobacter* DGAT or a variant thereof, including wherein said *Acinetobacter* DGAT is *Acinetobacter baylii* ADP1 diacylglycerol acyltransferase (AtfA). In certain aspects, said phosphatidate phosphatase is a yeast phosphatidate phosphatase, including wherein said yeast phosphatidate phosphatase is *Saccharomyces cerevisiae* phosphatidate phosphatase (yPah1). In other embodiments, any other DGAT, ACCase, or phosphatidate phosphate, including but not limited to those described herein, may be used.

In certain embodiments of the methods provided herein, said one or more polynucleotides are exogenous to the photosynthetic microorganism's, e.g., Cyanobacterium's, native genome. The one or more polynucleotides may also be present in one or more expression constructs, which may be stably integrated into the photosynthetic microorganism's genome, such as by recombination. Certain expression constructs comprise a constitutive promoter, and certain expression constructs comprise an inducible promoter. In certain aspects, said one or more polynucleotides are codon-optimized for expression in a photosynthetic microorganism, e.g., a Cyanobacterium.

The present invention also includes modified photosynthetic microorganisms, e.g., Cyanobacteria, comprising one or more polynucleotides encoding one or more enzymes associated with triglyceride biosynthesis, or variants or fragments thereof. In certain embodiments, said one or more enzymes comprise diacylglycerol acyltransferase (DGAT) and/or phosphatidate phosphatase. In certain aspects, said DGAT is an *Acinetobacter* DGAT or a variant thereof, including wherein said *Acinetobacter* DGAT is *Acinetobacter baylii* ADP1 diacylglycerol acyltransferase (AtfA). Other DGATs that may be used according to the present invention include, but are not limited to, *Streptomyces coelicolor* DGAT, *Alcanivorax borkumensis* DGAT, or the modified DGATs described herein. In certain aspects, said phosphatidate phosphatase is a yeast phosphatidate phosphatase, including wherein said yeast phosphatidate phosphatase is *Saccharomyces cerevisiae* phosphatidate phosphatase (yPah1).

Embodiments of the present invention also include modified photosynthetic microorganisms, e.g., Cyanobacteria, comprising one or more polynucleotides encoding one or more enzymes associated with fatty acid biosynthesis. In particular embodiments, said polynucleotides are exogenous to the Cyanobacterium's native genome. In certain embodiments, said one or more enzymes comprise diacylglycerol acyltransferase (DGAT) and/or phosphatidate phosphatase. In certain aspects, said DGAT is an *Acinetobacter* DGAT or a variant thereof, including wherein said *Acinetobacter* DGAT is *Acinetobacter baylii* ADP1 diacylglycerol acyltransferase (AtfA). Other DGATs that may be used according to the present invention include, but are not limited to, *Streptomyces coelicolor* DGAT, *Alcanivorax borkumensis* DGAT, or the modified DGATs described herein. In certain aspects, said phosphatidate phosphatase is a yeast phosphatidate phosphatase, including wherein said yeast phosphatidate phosphatase is *Saccharomyces cerevisiae* phosphatidate phosphatase (yPah1).

In certain embodiments, said one or more enzymes comprise acetyl-CoA carboxylase (ACCase). In certain aspects, said ACCase is a yeast ACCase or a variant thereof. In certain aspects, said ACCase is *Saccharomyces cerevisiae* acetyl-CoA carboxylase (yACC1), a *Triticum aestivum* ACCase, or a *Synechococcus* sp. PCC 7002 ACCAse. In certain embodiments, the one or more enzymes of a modified Cyanobacterium comprise acetyl-CoA carboxylase (ACCase), in combination with diacylglycerol acyltransferase (DGAT) and/or phosphatidate phosphatase.

In certain aspects, the one or more polynucleotides are exogenous to the photosynthetic microorganism's, e.g., Cyanobacterium's, native genome. The one or more polynucleotide sequences may be present in one or more expression constructs, which may be stably integrated into the photosynthetic microorganism's genome. In certain aspects, the one or more expression constructs comprise a constitutive promoter. In certain aspects, the one or more expression constructs comprise an inducible promoter. The one or more polynucleotides of the modified photosynthetic microorganism may be codon-optimized for expression in the photosynthetic microorganism, e.g., a Cyanobacteria. In certain aspects, a modified Cyanobacteria is *S. elongatus* PCC7942.

Certain embodiments contemplate modified photosynthetic microorganisms, e.g., Cyanobacteria, comprising one or more polynucleotides encoding one or more enzymes associated with fatty acid biosynthesis, wherein said one or more enzymes comprise *Saccharomyces cerevisiae* acetyl-CoA carboxylase (yAcc1), *Acinetobacter baylii* ADP1 diacylglycerol acyltransferase (AtfA), and *Saccharomyces cerevisiae* phosphatidate phosphatase (yPah1), wherein said one or more polynucleotides are codon-optimized for expression in Cyanobacterium, wherein expression of said one or more enzymes in regulated by one or more inducible promoters, and wherein said Cyanobacterium is *S. elongatus* PCC7942.

Particular embodiments of the various compositions and methods of the present invention contemplate the use of modified photosynthetic microorganisms, e.g., Cyanobacteria, comprising two or more different exogenous DGAT polynucleotides, or fragments or variants thereof, alone or in combination with one or more phosphatidate phosphatase and/or acetyl-CoA carboxylase polynucleotides, or fragments or variants thereof.

In various embodiments of the methods and compositions of the present invention, the modified photosynthetic microorganism is a Cyanobacteria selected from *S. elongatus* PCC 7942, a salt tolerant variant of *S. elongatus* PCC 7942, *Synechococcus* PCC 7002, and *Synechocystis* PCC 6803.

BRIEF DESCRIPTION OF THE SEVERAL VIEWS OF THE DRAWINGS

FIG. 4A shows the amount of various acyl chains in TAGs from cells expressing ADGATd, and FIG. 4B shows the amount of various acyl chains in TAGs from cells expressing ScoGAT.

FIG. 5A shows the TAGs expressed by a *Synechocystis* sp. strain PCC 6803 that carried ADP1-DGAT (+) or a vector control (−), following induction. FIG. 5B shows the TAGs expressed by a salt tolerant *S. elongatus* PCC 7942 that carried ADP1-DGAT, when grown in salt water, either uninduced (−) or induced (+) with IPTG. Control TAG (C16TAG) and fatty acid (palmitate) standards are also shown.

DETAILED DESCRIPTION

Figure 1:
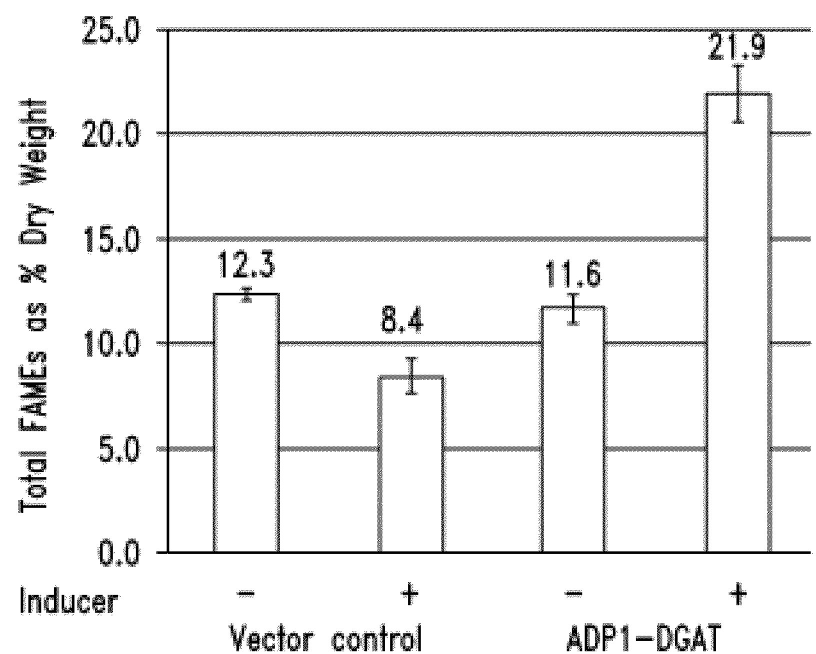
FIG. 1 shows the lipid content as measured by gas chromatography (GC) of *S. elongatus* PCC 7942 strain transformed with a diacylglycerol acyltransferase (ADP1-DGAT) gene from *Acinetobacter baylii* as compared to an empty vector control. Expression of the DGAT gene was under the control of an IPTG inducible promoter.

The present invention relates, in part, to the demonstration that photosynthetic organisms, including but not limited to Cyanobacteria, such as *Synechococcus*, which do not naturally produce triglycerides, can be genetically modified to synthesize triglycerides. In particular, as shown in the accompanying Examples, the addition of one or more polynucleotide sequences that encode one or more enzymes associated with triglyceride synthesis renders Cyanobacteria capable of converting their naturally-occurring fatty acids into triglyceride energy storage molecules. Examples of enzymes associated with triglyceride synthesis include enzymes having a phosphatidate phosphatase activity and enzymes having a diacylglycerol acyltransferase activity (DGAT). Specifically, phosphatidate phosphatase enzymes catalyze the production of diacylglycerol molecules, an immediate pre-cursor to triglycerides, and DGAT enzymes catalyze the final step of triglyceride synthesis by converting the diacylglycerol precursors to triglycerides.

The present invention also relates, in part, to the demonstration that Cyanobacteria can be genetically modified to increase the production of fatty acids. Since fatty acids provide the starting material for triglycerides, increasing the production of fatty acids in genetically modified Cyanobacteria may be utilized to increase the production of triglycerides. As shown in the accompanying Examples, Cyanobacteria can be modified to increase the production of fatty acids by introducing one or more exogenous polynucleotide sequences that encode one or more enzymes associated with fatty acid synthesis. In certain aspects, the exogenous polynucleotide sequence encodes an enzyme that comprises an acyl-CoA carboxylase (ACCase) activity, typically allowing increased ACCase expression, and, thus, increased intracellular ACCase activity. Increased intracellular ACCase activity contributes to the increased production of fatty acids because this enzyme catalyzes the "commitment step" of fatty acid synthesis. Specifically, ACCase catalyzes the production of a fatty acid synthesis precursor molecule, malonyl-CoA. In certain embodiments, the polynucleotide sequence encoding the ACCase is not native the Cyanobacterium's genome.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. The term "reference sequence" refers generally to a nucleic acid coding sequence, or amino acid sequence, of any enzyme having a diacylglycerol acyltransferase activity, a phosphatidate phosphatase activity, and/or an acetyl-CoA carboxylase activity, as described herein (see, e.g., SEQ ID NOS:1-9).

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an enzymatic activity of a reference polynucleotide or polypeptide. Representative biologically active fragments generally participate in an interaction, e.g., an intra-molecular or an inter-molecular interaction. An inter-molecular interaction can be a specific binding interaction or an enzymatic interaction. Examples of enzymatic interactions or activities include diacylglycerol acyltransferase activity, phosphatidate phosphatase activity, and/or acetyl-CoA carboxylase activity, as described herein.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

By "increased" or "increasing" is meant the ability of one or more modified photosynthetic microorganisms, e.g., Cyanobacteria, to produce a greater amount of a given fatty acid, lipid molecule, or triglyceride as compared to a control Cyanobacteria, such as an unmodified Cyanobacteria or a differently modified Cyanobacteria. Production of fatty acids can be measured according to techniques known in the art, such as Nile Red staining and gas chromatography. Production of triglycerides can be measured, for example, using commercially available enzymatic tests, including colorimetric enzymatic tests using glycerol-3-phosphate-oxidase.

By "obtained from" is meant that a sample such as, for example, a polynucleotide extract or polypeptide extract is isolated from, or derived from, a particular source, such as a desired organism or a specific tissue within a desired organism. "Obtained from" can also refer to the situation in which a polynucleotide or polypeptide sequence is isolated from, or derived from, a particular organism or tissue within an organism. For example, a polynucleotide sequence encoding a diacylglycerol acyltransferase, phosphatidate phosphatase, and/or acetyl-CoA carboxylase enzyme may be isolated from a variety of prokaryotic or eukaryotic organisms, or from particular tissues or cells within certain eukaryotic organism.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between) sequence identity with a reference polynucleotide sequence that encodes a diacylglycerol acyltransferase, a phosphatidate phosphatase, and/or an acetyl-CoA carboxylase enzyme. The terms "polynucleotide variant" and "variant" also include naturally-occurring allelic variants and orthologs that encode these enzymes.

With regard to polynucleotides, the term "exogenous" refers to a polynucleotide sequence that does not naturally occur in a wild-type cell or organism, but is typically introduced into the cell by molecular biological techniques. Examples of exogenous polynucleotides include vectors, plasmids, and/or man-made nucleic acid constructs encoding a desired protein. With regard to polynucleotides, the term "endogenous" or "native" refers to naturally occurring polynucleotide sequences that may be found in a given wild-type cell or organism. For example, certain cyanobacterial species do not typically contain a DGAT gene, and, therefore, do not comprise an "endogenous" polynucleotide sequence that encodes a DGAT polypeptide. Also, a particular polynucleotide sequence that is isolated from a first organism and transferred to second organism by molecular biological techniques is typically considered an "exogenous" polynucleotide with respect to the second organism.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length enzymes having diacylglycerol acyltransferase activity, phosphatidate phosphatase activity, and/or acetyl-CoA carboxylase activity, truncated fragments of these full-length polypeptides, variants of truncated fragments, as well as their related biologically active fragments. Typically, biologically active fragments of a polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken). Biologically active fragments of a polypeptide/enzyme having a diacylglycerol acyltransferase activity, a phosphatidate phosphatase activity, and/or acetyl-CoA carboxylase activity include peptides comprising amino acid sequences sufficiently similar to, or derived from, the amino acid sequences of a (putative) full-length reference polypeptide sequence. Typically, biologically active fragments comprise a domain or motif with at least one activity of a diacylglycerol acyltransferase polypeptide, phosphatidate phosphatase polypeptide, and/or acetyl-coA carboxylase polypeptide, and may include one or more (and in some cases all) of the various active domains. A biologically active fragment of a diacylglycerol acyltransferase, phosphatidate phosphatase, and/or acetyl-CoA carboxylase polypeptide can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

A "reference sequence," as used herein, refers to a wild-type polynucleotide or polypeptide sequence from any organism, e.g., wherein the polynucleotide encodes a polypeptide having a diacylglycerol acyltransferase enzymatic activity, a phosphatidate phosphatase enzymatic activity, or an acetyl-CoA carboxylase enzymatic activity, as described herein and known in the art. Exemplary polypeptide "reference sequences" are provided herein, including the amino acid sequence of a diacylglycerol acyltransferase polypeptide from *Acinetobacter baylii* (SEQ ID NO:1), the amino acid sequence of a phosphatidate phosphatase polypeptide (yPah1) from *Saccharomyces cerevisiae* (SEQ ID NO:2), and the amino acid sequence of an acyl-CoA carboxylase (yAcc1) from *Saccharomyces cerevisiae* (SEQ ID NO:3), among others (see, e.g., SEQ ID NOS:4-9, among others known to a person skilled in the art).

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "triglyceride" (triacylglycerol or neutral fat) refers to a fatty acid triester of glycerol. Triglycerides are typically non-polar and water-insoluble. Phosphoglycerides (or glycerophospholipids) are major lipid components of biological membranes.

"Transformation" refers to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell, such as a cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

Modified Phoosynthetic Microorganisms and Methods of Producing Triglycerides and Fatty Acids Certain embodiments of the present invention relate to modified photosynthetic microorganisms, e.g., Cyanobacteria, and methods of use thereof, wherein the modified photosynthetic microorganism comprises one or more polynucleotides encoding one or more enzymes associated with triglyceride biosynthesis, such as wherein the enzymes comprise a diacylglycerol acyltransferase (DGAT) activity and/or a phosphatidate phosphatase activity. The present invention contemplates the use of naturally-occurring and non-naturally-occurring variants of these DGAT and phosphatidate phosphatase enzymes, as well as variants of their encoding polynucleotides. In certain aspects, the DGAT encoding polynucleotide sequence is derived from *Acinetobacter baylii* (ADP1-DGAT), and the phosphatidate phosphatase encoding polynucleotide sequence is from *Saccharomyces cerevisiae* (yPah1). These enzyme encoding sequences, however, may be derived from any organism having a suitable DGAT or phosphatidate phosphatase enzyme, and may also include any man-made variants thereof, such as any optimized coding sequences (i.e., codon-optimized polynucleotides) or optimized polypeptide sequences. Exemplary polypeptide and polynucleotide sequences are described infra.

In certain embodiments, the modified photosynthetic microorganisms of the present invention may comprise two or more polynucleotides that encode DGAT or a variant or fragment thereof. In particular embodiments, the two or more polynucletoides are identical or express the same DGAT. In certain embodiments, these two or more polynucletoides may be different or may encode two different DGAT polypeptides. For example, in one embodiment, one of the polynucleotides may encode ADGATd, while another polynucleotide may encode ScoDGAT. In particular embodiments, the following DGATs are coexpressed in modified photosynthetic microorganisms, e.g., Cyanobacteria, using one of the following double DGAT strains: ADGATd(NS1)::ADGATd(NS2); ADGATn(NS1)::ADGATn(NS2); ADGATn(NS1)::SDGAT (NS2); SDGAT(NS1)::ADGATn(NS2); SDGAT(NS1)::SDGAT(NS2). For the NS1 vector, pAM2291, EcoRI follows ATG and is part of the open reading frame (ORF). For the NS2 vector, pAM1579, EcoRI follows ATG and is part of the ORF. A DGAT having EcoRI nucleotides following ATG may be cloned in either pAM2291 or pAM1579; such a DGAT is referred to as ADGATd. Other embodiments utilize the vector, pAM2314FTrc3, which is an NS1 vector with Nde/BgIII sites, or the vector, pAM1579FTrc3, which is the NS2 vector with Nde/BgIII sites. A DGAT without EcoRI nucleotides may be cloned into either of these last two vectors. Such a DGAT is referred to as ADGATn. As shown in the accompanying Examples, modified photosynthetic microorganisms expressing different DGATs express TAGs having different fatty acid compositions. Accordingly, certain embodiments of the present invention contemplate expressing two or more different DGATs, in order to produce DAGs having varied fatty acid compositions.

Related embodiments contemplate expressing two or more different phosphatidate phosphatase and/or two or more different acetyl-CoA carboxylases.

Embodiments of the present invention also relate to modified photosynthetic microorganisms, e.g., Cyanobacteria, and methods of use thereof, wherein the modified Cyanobacteria comprise one or more polynucleotides encoding enzymes associated with fatty acid biosynthesis, such as wherein said polynucleotides are exogenous to the Cyanobacterium's native genome. In certain aspects, the enzymes associated with fatty acid synthesis comprise an acetyl-CoA carboxylase (ACCase) activity, including naturally-occurring and non-naturally-occurring functional variants of such enzymes and their encoding polynucleotides. In certain embodiments, the polynucleotide sequence encoding the ACCase enzyme is derived from *Saccharomyces cerevisiae* (yAcc1). As above, however, these ACCase enzyme encoding sequences may be derived from any organism having a suitable ACCase enzyme, and may also include any man-made variants thereof, such as any optimized coding sequences (i.e., codon-optimized polynucleotides) or optimized polypeptide sequences.

Since, as noted above, fatty acids provide the starting material for triglyceride production, genetically modified Cyanobacteria having increased fatty acid production may by utilized to improve the overall production of triglycerides. Accordingly, certain embodiments relate to modified Cyanobacteria, and methods of use thereof, wherein the Cyanobacteria comprise one or more polynucleotides encoding enzymes associated with fatty acid synthesis and triglyceride synthesis. As such, in certain embodiments, the modified Cyanobacteria of the present invention comprise one or more polynucleotides encoding enzymes that comprise a DGAT activity and/or a phosphatidate phosphatase activity, as well as an exogenous enzyme comprising an ACCase activity.

Embodiments of the present invention also include methods of producing triglyceride in a photosynthetic microorganism, e.g., a Cyanobacterium, comprising introducing one or more polynucleotides encoding one or more enzymes associated with triglyceride biosynthesis into a photosynthetic microorganism, incubating the photosynthetic microorganism for a time and under conditions sufficient to allow triglyceride production, thereby producing triglyceride in the photosynthetic microorganism. Also contemplated are methods of producing a triglyceride in a photosynthetic microorganism, e.g., a Cyanobacterium, comprising culturing a photosynthetic microorganism comprising one or more polynucleotides encoding one or more enzymes associated with triglyceride biosynthesis, for a time and under conditions sufficient to allow triglyceride production. In certain embodiments, the one or more enzymes comprise a diacylglycerol acyltransferase (DGAT) enzymatic activity and/or a phosphatidate phosphatase enzymatic activity. In particular embodiments, the one or more enzymes comprise both a DGAT enzymatic activity and a phosphotidate phosphatase enzymatic activity. In certain embodiments the one or more enzymes comprise an acyl-CoA carboxylase (ACCase) enzymatic activity, as well as a diacylglycerol DGAT enzymatic activity and/or a phosphatidate phosphatase enzymatic activity. In one embodiment, the one or more enzymes comprise a DGAT enzymatic activity, a phosphotidate phosphatase enzymatic activity, and an acyl-CoA carboxylase (ACCase) enzymatic activity. In particular embodiments, one or more of the polynucleotides are exogenous to the photosynthetic microorganism's native genome.

The present invention also relates to methods of producing an increased amount of fatty acid, e.g., a free fatty acid, in a photosynthetic microorganism, e.g., a Cyanobacterium, comprising introducing one or more polynucleotides encoding one or more enzymes associated with fatty acid biosynthesis into a photosynthetic microorganism, culturing the Cyanobacterium for a time and under conditions sufficient to allow increased fatty acid production, thereby producing an increased amount of fatty acid in the Cyanobacterium. Also contemplated are methods of producing an increased amount of fatty acid in a photosynthetic microorganism, e.g., a Cyanobacterium, comprising culturing a photosynthetic microorganism comprising one or more polynucleotides encoding one or more enzymes associated with fatty acid biosynthesis. In certain embodiments, one or more of the polynucleotides are exogenous to the photosynthetic microorganism's native genome. In certain embodiments, the one or more enzymes comprise an ACCase enzymatic activity. In producing triglycerides, the modified Cyanobacteria of the present invention may be cultured according to routine techniques known in the art and exemplified herein, such as photobioreactor based culture techniques.

The present invention also relates to methods of preparing a modified photosynthetic microorganism, e.g., a modified Cyanobacterium, such as by genetic modification, to increase production of naturally-occurring fatty acids, e.g., free fatty acids, and/or to produce triglycerides. Photosynthetic microorganisms, such as Cyanobacteria, can be genetically modified according to routine techniques known in the art, such as by transformation of vectors suitable for use in Cyanobacteria. In certain aspects, genetic manipulation in Cyanobacteria can be performed by the introduction of non-replicating vectors which contain native Cyanobacterial sequences, exogenous genes of interest, and drug resistance genes. Upon introduction into the Cyanobacterial cell, the vectors may be integrated into the Cyanobacterial genome through homologous recombination. In this way, the exogenous gene of interest and the drug resistance gene are stably integrated into the Cyanobacterial genome. Such recombinants cells can then be isolated from non-recombinant cells by drug selection. Examples of suitable vectors are provided herein.

Embodiments of the present invention include methods of producing triglycerides in a Cyanobacterium, comprising introducing one or more polynucleotides encoding one or more enzymes associated with triglyceride biosynthesis into a Cyanobacterium, such as an enzyme having a phosphatidate phosphatase activity and/or an enzyme having a diacylglycerol transferase activity.

In certain aspects, genetically modified photosynthetic microorganisms, e.g., Cyanobacteria, may be prepared by (i) introducing one or more desired polynucleotides encoding one or more enzymes associated with triglyceride biosynthesis into a photosynthetic microorganism, and (ii) selecting for, and/or isolating, photosynthetic microorganisms that comprise the one or more desired polynucleotides. As one example, selection and isolation may include the use of antibiotic resistant markers known in the art (e.g., kanamycin, spectinomycin, and streptomycin) In certain embodiments, genetically modified photosynthetic microorganisms, e.g., Cyanobacteria, may be prepared by (i) introducing one or more desired, exogenous polynucleotides encoding one or more enzymes associated with fatty acid biosynthesis into a photosynthetic microorganism, e.g., a Cyanobacteria, and (ii) selecting for, and/or isolating, photosynthetic microorganisms that comprise one or more desired, exogenous polynucleotides. In certain embodiments, genetically modified photosynthetic microorganisms may be prepared by (i) introducing one or more desired polynucleotides encoding one or more enzymes associated with fatty acid biosynthesis and triglyceride synthesis into a photosynthetic microorganism, and (ii) selecting for, and/or isolating, photosynthetic microorganisms that comprise the one or more desired polynucleotides.

In certain embodiments, the one or more enzymes associated with triglyceride synthesis comprise a diacylglycerol acyltransferase (DGAT) enzymatic activity or a phosphatidate phosphatase enzymatic activity. In some embodiments, the one or more enzymes associated with triglyceride synthesis comprise both a DGAT enzymatic activity and a phosphatidate phosphatase enzymatic activity. In certain embodiments the one or more enzymes associated fatty acid biosynthesis comprise an acyl-CoA carboxylase (ACCase) enzymatic activity. In particular embodiments, the one or more enzymes associated with triglyceride synthesis comprise an acyl-CoA carboxylase (ACCase) enzymatic activity and either a DGAT enzymatic activity or a phosphatidate phosphatase enzymatic activity. In one embodiment, the one or more enzymes associated with triglyceride synthesis comprise an acyl-CoA carboxylase (ACCase) enzymatic activity, a DGAT enzymatic activity, and a phosphatidate phosphatase enzymatic activity.

Photosynthetic Microorganisms

Modified photosynthetic microorganisms of the present invention may be any type of photosynthetic microorganism. These include, but are not limited to photosynthetic bacteria, green algae, and cyanobacteria. The photosynthetic microorganism can be, for example, a naturally photosynthetic microorganism, such as a cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; eukaryotes, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., and/or *Tolypothrix.*

A modified Cyanobacteria of the present invention may be from any genera or species of Cyanobacteria that is genetically manipulable, i.e., permissible to the introduction and expression of exogenous genetic material. Examples of Cyanobacteria that can be engineered according to the methods of the present invention include, but are not limited to, the genus *Synechocystis, Synechococcus, Thermosynechococcus, Nostoc, Prochlorococcu, Microcystis, Anabaena, Spirulina*, and *Gloeobacter.*

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the present invention.

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Heterocysts may also form under the appropriate environmental conditions (e.g., anoxic) whenever nitrogen is necessary. Heterocyst-forming species are specialized for nitrogen fixation and are able to fix nitrogen gas, which cannot be used by plants, into ammonia ($NH_3$), nitrites ($NO_2^-$), or nitrates ($NO_3^-$), which can be absorbed by plants and converted to protein and nucleic acids.

Many Cyanobacteria also form motile filaments, called hormogonia, which travel away from the main biomass to bud and form new colonies elsewhere. The cells in a hormogonium are often thinner than in the vegetative state, and the cells on either end of the motile chain may be tapered. In order to break away from the parent colony, a hormogonium often must tear apart a weaker cell in a filament, called a necridium.

Each individual cyanobacterial cell typically has a thick, gelatinous cell wall. Cyanobacteria differ from other gram-negative bacteria in that the quorum sensing molecules autoinducer-2 and acyl-homoserine lactones are absent. They lack flagella, but hormogonia and some unicellular species may move about by gliding along surfaces. In water columns some Cyanobacteria float by forming gas vesicles, like in archaea.

Cyanobacteria have an elaborate and highly organized system of internal membranes that function in photosynthesis. Photosynthesis in Cyanobacteria generally uses water as an electron donor and produces oxygen as a by-product, though some Cyanobacteria may also use hydrogen sulfide, similar to other photosynthetic bacteria. Carbon dioxide is reduced to form carbohydrates via the Calvin cycle. In most forms the photosynthetic machinery is embedded into folds of the cell membrane, called thylakoids. Due to their ability to fix nitrogen in aerobic conditions, Cyanobacteria are often found as symbionts with a number of other groups of organisms such as fungi (e.g., lichens), corals, pteridophytes (e.g., Azolla), and angiosperms (e.g., Gunnera), among others.

Cyanobacteria are the only group of organisms that are able to reduce nitrogen and carbon in aerobic conditions. The water-oxidizing photosynthesis is accomplished by coupling the activity of photosystem (PS) II and I (Z-scheme). In anaerobic conditions, Cyanobacteria are also able to use only PS I (i.e., cyclic photophosphorylation) with electron donors other than water (e.g., hydrogen sulfide, thiosulphate, or molecular hydrogen), similar to purple photosynthetic bacteria. Furthermore, Cyanobacteria share an archaeal property; the ability to reduce elemental sulfur by anaerobic respiration in the dark. The Cyanobacterial photosynthetic electron transport system shares the same compartment as the components of respiratory electron transport. Typically, the plasma membrane contains only components of the respiratory chain, while the thylakoid membrane hosts both respiratory and photosynthetic electron transport.

Phycobilisomes, attached to the thylakoid membrane, act as light harvesting antennae for the photosystems of Cyanobacteria. The phycobilisome components (phycobiliproteins) are responsible for the blue-green pigmentation of most Cyanobacteria. Color variations are mainly due to carotenoids and phycoerythrins, which may provide the cells with a red-brownish coloration. In some Cyanobacteria, the color of light influences the composition of phycobilisomes. In green light, the cells accumulate more phycoerythrin, whereas in red light they produce more phycocyanin. Thus, the bacteria appear green in red light and red in green light. This process is known as complementary chromatic adaptation and represents a way for the cells to maximize the use of available light for photosynthesis.

In particular embodiments, the Cyanobacteria may be, e.g., a marine form of Cyanobacteria or a fresh water form of Cyanobacteria. Examples of marine forms of Cynobacteria include, but are not limited to *Synechococcus* WH8102, *Synechococcus* RCC307, *Synechococcus* NKBG 15041c, and *Trichodesmium*. Examples of fresh water forms of Cyaobacteria include, but are not limited to, *S. elongatus* PCC 7942, *Synechocystis* PCC6803, *Plectonema boryanum*, and *Anabaena* sp. Exogenous genetic material encoding the desired enzymes may be introduced either transiently, such as in certain self-replicating vectors, or stably, such as by integration (e.g., recombination) into the Cyanobacterium's native genome.

In other embodiments, a genetically modified Cyanobacteria of the present invention may be capable of growing in brackish or salt water. When using a fresh water form of Cyanobacteria, the overall net cost for production of triglycerides will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It consists of liquid waste released from domestic and commercial properties, industry, and/or agriculture and can encompass a wide range of possible contaminants at varying concentrations.

There is a broad distribution of Cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In particular embodiments, the present invention contemplates the use of a Cyanobacteria PCC 7942, altered in a way that allows for growth in either waste water or salt/brackish water. A *Synechococcus elongatus* PCC 7942 mutant resistant to sodium chloride stress has been described (Bagchi, S. N. et al., Photosynth Res. 2007, 92:87-101), and a genetically modified *S. elongatus* PCC 7942 tolerant of growth in salt water has been described (Waditee, R. et al., PNAS 2002, 99:4109-4114). Salt water tolerant Cyanobacteria may also be prepared as described in the accompanying Examples. According to the present invention a salt water tolerant strain is capable of growing in water or media having a salinity in the range of 0.5% to 4.0% salinity, although it is not necessarily capable of growing in all salinities encompassed by this range. In one embodiment, a salt tolerant strain is capable of growth in water or media having a salinity in the range of 1.0% to 2.0% salinity. In another embodiment, a salt water tolerant strain is capable of growth in water or media having a salinity in the range of 2.0% to 3.0% salinity.

Examples of cyanobacteria that may be utilized and/or genetically modified according to the methods described herein include, but are not limited to, *Chroococcales* cyanobacteria from the genera *Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloecapsa, Gloeothece, Merismopedia, Microcystis, Radiocystis, Rhabdoderma, Snowella, Synychococcus, Synechocystis, Thermosenechococcus*, and *Woronichinia; Nostacales* cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis*, and *Toypothrix; Oscillatoriales* cyanobacteria from the genera *Arthrospira, Geitlennema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Spirulina, Symploca, Trichodesmium, Tychonema; Pleurocapsales cyanobacterium* from the genera *Chroococcidiopsis, Dermocarpa, Dermocarpella, Myxosarcina, Pleurocapsa, Stanieria, Xenococcus; Prochlorophytes* cyanobacterium from the genera *Prochloron, Prochlorococcus, Prochlorothrix*; and *Stigonematales* cyanobacterium from the genera *Capsosira, Chlorogeoepsis, Fischerella, Hapalosiphon, Mastigocladopsis, Nostochopsis, Stigonema, Symphyonema, Symphonemopsis, Umezakia*, and *Westiellopsis*. In certain embodiments, the cyanobacterium is from the genus *Synechococcus*, including, but not limited to *Synechococcus bigranulatus, Synechococcus elongatus, Synechococcus leopoliensis, Synechococcus lividus, Synechococcus nidulans*, and *Synechococcus rubescens*.

In certain embodiments, the cyanobacterium is *Anabaena* sp. strain PCC 7120, *Synechocystis* sp. strain PCC 6803, *Nostoc muscorum, Nostoc ellipsosporum*, or *Nostoc* sp. strain PCC 7120. In certain preferred embodiments, the cyanobacterium is *Synechococcus elongatus* sp. strain PCC 7942. Additional examples of Cyanobacteria that may utilized in the methods provided herein include, but are not limited to, *Synechococcus* sp. strains WH7803, WH8102, WH8103 (typically genetically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), and Heterocyst-forming strains *Anabaena* sp. strains ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In particular embodiments, the genetically modified, photosynthetic microorganism, e.g., Cyanobacteria, of the present invention may be used to produce triglycerides from just sunlight, water, air, and minimal nutrients, using routine culture techniques of any reasonably desired scale. In particular embodiments, the present invention contemplates using spontaneous mutants of photosynthetic microorganisms that demonstrate a growth advantage under a defined growth condition. Among other benefits, the ability to produce large amounts of triglycerides from minimal energy and nutrient input makes the modified photosynthetic microorganism, e.g., Cyanobacteria, of the present invention a readily manageable and efficient source of feedstock in the subsequent production of both biofuels, such as biodiesel, as well as specialty chemicals, such as glycerin.

Methods of Producing and Culturing Modified Photosynthetic Microorganisms

Photosynthetic microorganisms, e.g., Cyanobacteria, may be genetically modified according to techniques known in the art. As noted above, in certain aspects, genetic manipulation in Cyanobacteria can be performed by the introduction of non-replicating vectors that contain native Cyanobacterial sequences, exogenous genes of interest and drug resistance genes. Upon introduction into the Cyanobacterial cell, the vectors may be integrated into the Cyanobacterial genome through homologous recombination. In this way, the exogenous gene of interest and the drug resistance gene are stably integrated into the Cyanobacterial genome. Such recombinants cells can then be isolated from non-recombinant cells by drug selection. Cell transformation methods and selectable markers for Cyanobacteria are also well known in the art (see, e.g., Wirth, *Mol Gen Genet* 216:175-7, 1989; and Koksharova, *Appl Microbiol Biotechnol* 58:123-37, 2002).

Cyanobacteria may be cultured or cultivated according to techniques known in the art, such as those described in Acreman et al. (*Journal of Industrial Microbiology and Biotechnology* 13:193-194, 1994), in addition to photobioreactor based techniques, such as those described in Nedbal et al. (*Biotechnol Bioeng*. 100:902-10, 2008). One example of typical laboratory culture conditions for Cyanobacterium is growth in BG-11 medium (ATCC Medium 616) at 30° C. in a vented culture flask with constant agitation and constant illumination at 30-100 μmole photons $m^{-2}$ $sec^{-1}$.

A wide variety of mediums are available for culturing Cyanobacteria, including, for example, Aiba and Ogawa (AO) Medium, Allen and Amon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [BG-11 medium]), ATCC Medium 819 (Blue-green Nitrogen-fixing Medium; ATCC Medium 616 [BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), Beggiatoa Medium (ATCC Medium 138), Beggiatoa Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (Halophilic cyanobacteria), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erdschreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Spirulina*: ATCC Medium 1679*, Spirulina* (SP) Medium, van Rijn and Cohen (RC) Medium, Walsby's Medium, Yopp Medium, and Z8 Medium, among others.

In certain embodiments, modified photosynthetic microorganisms, e.g., Cyanobacteria, are grown under conditions favorable for producing triglycerides and/or fatty acids. In particular embodiments, light intensity is between 100 and 2000 uE/m2/s, or between 200 and 1000 uE/m2/s. In particular embodiments, the pH range of culture media is between 7.0 and 10.0. In certain embodiments, $CO_2$ is injected into the culture apparatus to a level in the range of 1% to 10%. In particular embodiments, the range of $CO_2$ is between 2.5% and 5%. In certain embodiments, nutrient supplementation is performed during the linear phase of growth. Each of these conditions are desirable for triglyceride production.

Nucleic Acids and Polypeptides

In various embodiments, modified photosynthetic microorganisms, e.g., Cyanobacteria, of the present invention comprise one or more exogenous or introduced nucleic acids that encode a polypeptide having an activity associated with triglyceride or fatty acid biosynthesis, including but not limited to any of those described herein. In particular embodiments, the exogenous nucleic acid does not comprises a nucleic acid sequence that is native to the microorganism's genome. In particular embodiments, the exogenous nucleic acid comprises a nucleic acid sequence that is native to the microorganism's genome, but it has been introduced into the microorganism, e.g., in a vector or by molecular biology techniques, for example, to increase expression of the nucleic acid and/or its encoded polypeptide in the microorganism.

Triglyceride Biosynthesis

Triglycerides, or triacylglycerols (TAG), consist primarily of glycerol esterified with three fatty acids, and yield more energy upon oxidation than either carbohydrates or proteins. Triglycerides provide an important mechanism of energy storage for most eukaryotic organisms. In mammals, TAGs are synthesized and stored in several cell types, including adipocytes and hepatocytes (Bell et al. *Annu. Rev. Biochem.* 49:459-487, 1980) (herein incorporated by reference). In plants, TAG production is mainly important for the generation of seed oils.

In contrast to eukaryotes, the observation of triglyceride production in prokaryotes has been limited to certain actinomycetes, such as members of the genera *Mycobacterium, Nocardia, Rhodococcus* and *Streptomyces*, in addition to certain members of the genus *Acinetobacter*. In certain actinomycetes species, triglycerides may accumulate to nearly 80% of the dry cell weight, but accumulate to only about 15% of the dry cell weight in *Acinetobacter*. In general, triglycerides are stored in spherical lipid bodies, with quantities and diameters depending on the respective species, growth stage, and cultivation conditions. For example, cells of *Rhodococcus opacus* and *Streptomyces lividans* contain only few TAGs when cultivated in complex media with a high content of carbon and nitrogen; however, the lipid content and the number of TAG bodies increase drastically when the cells are cultivated in mineral salt medium with a low nitrogen-to-carbon ratio, yielding a maximum in the late stationary growth phase. At this stage, cells can be almost completely filled with lipid bodies exhibiting diameters ranging from 50 to 400 nm. One example is *R. opacus* PD630, in which lipids can reach more than 70% of the total cellular dry weight.

In bacteria, TAG formation typically starts with the docking of a diacylglycerol acyltransferase enzyme to the plasma membrane, followed by formation of small lipid droplets (SLDs). These SLDs are only some nanometers in diameter and remain associated with the membrane-docked enzyme. In this phase of lipid accumulation, SLDs typically form an emulsive, oleogenous layer at the plasma membrane. During prolonged lipid synthesis, SLDs leave the membrane-associated acyltransferase and conglomerate to membrane-bound lipid prebodies. These lipid prebodies reach distinct sizes, e.g., about 200 nm in *A. calcoaceticus* and about 300 nm in *R. opacus*, before they lose contact with the membrane and are released into the cytoplasm. Free and membrane-bound lipid prebodies correspond to the lipid domains occurring in the cytoplasm and at the cell wall, as observed in *M. smegmatis* during fluorescence microscopy and also confirmed in *R. opacus* PD630 and *A. calcoaceticus* ADP1 (see, e.g., Christensen et al., *Mol. Microbiol.* 31:1561-1572, 1999); and Wältermann et al., *Mol. Microbiol.* 55:750-763, 2005). Inside the lipid prebodies, SLDs coalesce with each other to form the homogenous lipid core found in mature lipid bodies, which often appear opaque in electron microscopy.

The compositions and structures of bacterial TAGs vary considerably depending on the microorganism and on the carbon source. In addition, unusual acyl moieties, such as phenyldecanoic acid and 4,8,12 trimethyl tridecanoic acid, may also contribute to the structural diversity of bacterial TAGs. (see, e.g., Alvarez et al., *Appl Microbiol Biotechnol.* 60:367-76, 2002).

As with eukaryotes, the main function of TAGs in prokaryotes is to serve as a storage compound for energy and carbon. TAGs, however, may provide other functions in prokaryotes. For example, lipid bodies may act as a deposit for toxic or useless fatty acids formed during growth on recalcitrant carbon sources, which must be excluded from the plasma membrane and phospholipid (PL) biosynthesis. Furthermore, many TAG-accumulating bacteria are ubiquitous in soil, and in this habitat, water deficiency causing dehydration is a frequent environmental stress. Storage of evaporation-resistant lipids might be a strategy to maintain a basic water supply, since oxidation of the hydrocarbon chains of the lipids under conditions of dehydration would generate considerable amounts of water. Cyanobacteria such as *Synechococcus*, however, do not produce triglycerides, because these organisms lack the enzymes necessary for triglyceride biosynthesis.

Triglycerides are synthesized from fatty acids and glycerol. As one mechanism of triglyceride (TAG) synthesis, sequential acylation of glycerol-3-phosphate via the "Kennedy Pathway" leads to the formation of phosphatidate. Phosphatidate is then dephosphorylated by the enzyme phosphatidate phosphatase to yield 1,2 diacylglycerol (DAG). Using DAG as a substrate, at least three different classes of enzymes are capable of mediating TAG formation. As one example, an enzyme having diacylglycerol transferase (DGAT) activity catalyzes the acylation of DAG using acyl-CoA as a substrate. Essentially, DGAT enzymes combine acyl-CoA with 1,2 diacylglycerol molecule to form a TAG. As an alternative, Acyl-CoA-independent TAG synthesis may be mediated by a phospholipid:DAG acyltransferase found in yeast and plants, which uses phospholipids as acyl donors for DAG esterification. Third, TAG synthesis in animals and plants may be mediated by a DAG-DAG-transacylase, which uses DAG as both an acyl donor and acceptor, yielding TAG and monoacylglycerol.

Modified photosynthetic microorganisms, e.g., Cyanobacteria, of the present invention may comprise one or more exogenous polynucleotides encoding polypeptides comprising one or more of the polypeptides and enzymes described above. In particular embodiments, the one or more exogenous polynucleotides encode a diacylglycerol transferase and/or a phosphatidate phosphatase, or a variant or function fragment thereof.

Since wild-type Cyanobacteria do not typically encode the enzymes necessary for triglyceride synthesis, such as the enzymes having phosphatidate phosphatase activity and diacylglycerol transferase activity, embodiments of the present invention include genetically modified Cyanobacteria that comprise polynucleotides encoding one or more enzymes having a phosphatidate phosphatase activity and/or one or more enzymes having a diacylglycerol transferase activity.

Moreover, since triglycerides are typically formed from fatty acids, the level of fatty acid biosynthesis in a cell may limit the production of triglycerides. Increasing the level of fatty acid biosynthesis may, therefore, allow increased production of triglycerides. As discussed below, Acetyl-CoA carboxylase catalyzes the commitment step to fatty acid biosynthesis. Thus, certain embodiments of the present invention include Cyanobacterium, and methods of use thereof, comprising polynucleotides that encode one or more enzymes having Acetyl-CoA carboxylase activity to increase fatty acid biosynthesis and lipid production, in addition to one or more enzymes having phosphatidate phosphatase and/or diacylglycerol transferase activity to catalyze triglyceride production.

As used herein, a "phosphatidate phosphatase" gene of the present invention includes any polynucleotide sequence encoding amino acids, such as protein, polypeptide or peptide, obtainable from any cell source, which demonstrates the ability to catalyze the dephosphorylation of phosphatidate (PtdOH) under enzyme reactive conditions, yielding diacylglycerol (DAG) and inorganic phosphate, and further includes any naturally-occurring or non-naturally occurring variants of a phosphatidate phosphatase sequence having such ability.

Phosphatidate phosphatases (PAP, 3-sn-phosphatidate phosphohydrolase) catalyze the dephosphorylation of phosphatidate (PtdOH), yielding diacylglycerol (DAG) and inorganic phosphate. This enzyme belongs to the family of hydrolases, specifically those acting on phosphoric monoester bonds. The systematic name of this enzyme class is 3-sn-phosphatidate phosphohydrolase. Other names in common use include phosphatic acid phosphatase, acid phosphatidyl phosphatase, and phosphatic acid phosphohydrolase. This enzyme participates in at least 4 metabolic pathways: glycerolipid metabolism, glycerophospholipid metabolism, ether lipid metabolism, and sphingolipid metabolism.

PAP enzymes have roles in both the synthesis of phospholipids and triacylglycerol through its product diacylglycerol, as well as the generation or degradation of lipid-signaling molecules in eukaryotic cells. PAP enzymes are typically classified as either $Mg^{2+}$-dependent (referred to as PAP1 enzymes) or $Mg^{2+}$-independent (PAP2 or lipid phosphate phosphatase (LPP) enzymes) with respect to their cofactor requirement for catalytic activity. In both yeast and mammalian systems, PAP2 enzymes are known to be involved in lipid signaling. By contrast, PAP1 enzymes, such as those found in *Saccharomyces cerevisiae*, play a role in de novo lipid synthesis (Han, et al. *J Biol Chem.* 281:9210-9218, 2006), thereby revealing that the two types of PAP are responsible for different physiological functions.

In both yeast and higher eukaryotic cells, the PAP reaction is the committed step in the synthesis of the storage lipid triacylglycerol (TAG), which is formed from PtdOH through the intermediate DAG. The reaction product DAG is also used in the synthesis of the membrane phospholipids phosphatidylcholine (PtdCho) and phosphatidylethanolamine. The substrate PtdOH is used for the synthesis of all membrane phospholipids (and the derivative inositol-containing sphingolipids) through the intermediate CDP-DAG. Thus, regulation of PAP activity might govern whether cells make storage lipids and phospholipids through DAG or phospholipids through CDP-DAG. In addition, PAP is involved in the transcriptional regulation of phospholipid synthesis.

PAP1 enzymes have been purified and characterized from the membrane and cytosolic fractions of yeast, including a gene (Pah1, formerly known as Smp2) been identified to encode a PAP1 enzyme in *S. cerevisiae*. The Pah1-encoded PAP1 enzyme is found in the cytosolic and membrane fractions of the cell, and its association with the membrane is peripheral in nature. As expected from the multiple forms of PAP1 that have been purified from yeast, pah1Δ mutants still contain PAP1 activity, indicating the presence of an additional gene or genes encoding enzymes having PAP1 activity.

Analysis of mutants lacking the Pah1-encoded PAP1 has provided evidence that this enzyme generates the DAG used for lipid synthesis. Cells containing the pah1Δ mutation accumulate PtdOH and have reduced amounts of DAG and its acylated derivative TAG. Phospholipid synthesis predominates over the synthesis of TAG in exponentially growing yeast, whereas TAG synthesis predominates over the synthesis of phospholipids in the stationary phase of growth. The effects of the pah1Δ mutation on TAG content are most evident in the stationary phase. For example, stationary phase cells devoid of the Pah1 gene show a reduction of >90% in TAG content. Likewise, the pah1Δ mutation shows the most marked effects on phospholipid composition (e.g. the consequent reduction in PtdCho content) in the exponential phase of growth. The importance of the Pah1-encoded PAP1 enzyme to cell physiology is further emphasized because of its role in the transcriptional regulation of phospholipid synthesis.

The requirement of $Mg^{2+}$ ions as a cofactor for PAP enzymes is correlated with the catalytic motifs that govern the phosphatase reactions of these enzymes. For example, the Pah1-encoded PAP1 enzyme has a DxDxT (SEQ ID NO:30) catalytic motif within a haloacid dehalogenase (HAD)-like domain ("x" is any amino acid). This motif is found in a superfamily of $Mg^{2+}$-dependent phosphatase enzymes, and its first aspartate residue is responsible for binding the phosphate moiety in the phosphatase reaction. By contrast, the DPP1- and LPP1-encoded PAP2 enzymes contain a three-domain lipid phosphatase motif that is localized to the hydrophilic surface of the membrane. This catalytic motif, which comprises the consensus sequences KxxxxxxRP (domain 1) (SEQ ID NO:10), PSGH (domain 2) (SEQ ID NO:11), and SRxxxxxHxxxD (domain 3) (SEQ ID NO:12), is shared by a superfamily of lipid phosphatases that do not require $Mg^{2+}$ ions for activity. The conserved arginine residue in domain 1 and the conserved histidine residues in domains 2 and 3 may be essential for the catalytic activity of PAP2 enzymes. Accordingly, a phosphatide phosphatase polypeptide may comprise one or more of the above-described catalytic motifs.

A polynucleotide encoding a polypeptide having a phosphatidate phosphatase enzymatic activity may be obtained from any organism having a suitable, endogenous phosphatidate phosphatase gene. Examples of organisms that may be used to obtain a phosphatidate phosphatase encoding polynucleotide sequence include, but are not limited to, *Homo sapiens, Mus musculus, Rattus norvegicus, Bos taurus, Drosophila melanogaster, Arabidopsis thaliana, Magnaporthe grisea, Saccharomyces cerevisiae, Schizosaccharomyces pombe, Cryptococcus neoformans*, and *Bacillus pumilus*, among others. As used herein, a “diacylglycerol acyltransferase” (DGAT) gene of the present invention includes any polynucleotide sequence encoding amino acids, such as protein, polypeptide or peptide, obtainable from any cell source, which demonstrates the ability to catalyze the production of triacylglycerol from 1,2-diacylglycerol and fatty acyl substrates under enzyme reactive conditions, in addition to any naturally-occurring (e.g., allelic variants, orthologs) or non-naturally occurring variants of a diacylglycerol acyltransferase sequence having such ability. DGAT genes of the present invention also polynucleotide sequences that encode bi-functional proteins, such as those bi-functional proteins that exhibit a DGAT activity as well as a CoA:fatty alcohol acyltransferase activity, i.e., a wax ester synthesis (WS) activity, as often found in many TAG producing bacteria.

Diacylglycerol acyltransferases (DGATs) are members of the O-acyltransferase superfamily, which esterify either sterols or diacylglycerols in an oleoyl-CoA-dependent manner. DGAT in particular esterifies diacylglycerols, which reaction represents the final enzymatic step in the production of triacylglycerols in plants, fungi and mammals. Specifically, DGAT is responsible for transferring an acyl group from acyl-coenzyme-A to the sn-3 position of 1,2-diacylglycerol (DAG) to form triacylglycerol (TAG). DGAT is an integral membrane protein that has been generally described in Harwood (*Biochem. Biophysics. Acta,* 1301:7-56, 1996), Daum et al. (*Yeast* 16:1471-1510, 1998), and Coleman et al. (*Annu. Rev. Nutr.* 20:77-103, 2000) (each of which are herein incorporated by reference).

In plants and fungi, DGAT is associated with the membrane and lipid body fractions. In catalyzing TAGs, DGAT contributes mainly to the storage of carbon used as energy reserves. In animals, however, the role of DGAT is more complex. DGAT not only plays a role in lipoprotein assembly and the regulation of plasma triacylglycerol concentration (Bell, R. M., et al.), but participates as well in the regulation of diacylglycerol levels (Brindley, *Biochemistry of Lipids*, Lipoproteins and Membranes, eds. Vance, D. E. & Vance, J. E. (Elsevier, Amsterdam), 171-203; and Nishizuka, *Science* 258:607-614 (1992) (each of which are herein incorporated by reference)).

In eukaryotes, at least three independent DGAT gene families (DGAT1, DGAT2, and PDAT) have been described that encode proteins with the capacity to form TAG. Yeast contain all three of DGAT1, DGAT2, and PDAT, but the expression levels of these gene families varies during different phases of the life cycle (Dahlqvst, A., et al. *Proc. Natl. Acad. Sci.* USA 97:6487-6492 (2000) (herein incorporated by reference).

In prokaryotes, WS/DGAT from *Acinetobacter calcoaceticus* ADP1 represents the first identified member of a widespread class of bacterial wax ester and TAG biosynthesis enzymes. This enzyme comprises a putative membrane-spanning region but shows no sequence homology to the DGAT1 and DGAT2 families from eukaryotes. Under in vitro conditions, WS/DGAT shows a broad capability of utilizing a large variety of fatty alcohols, and even thiols as acceptors of the acyl moieties of various acyl-CoA thioesters. WS/DGAT acylatransferase enzymes exhibit extraordinarily broad substrate specificity. Genes for homologous acyltransferases have been found in almost all bacteria capable of accumulating neutral lipids, including, for example, *Acinetobacter baylii, A. baumanii*, and *M. avium*, and *M. tuberculosis* CDC1551, in which about 15 functional homologues are present (see, e.g., Daniel et al., *J. Bacteriol.* 186:5017-5030, 2004; and Kalscheuer et al., *J. Biol. Chem.* 287:8075-8082, 2003).

DGAT proteins may utilize a variety of acyl substrates in a host cell, including fatty acyl-CoA and fatty acyl-ACP molecules. In addition, the acyl substrates acted upon by DGAT enzymes may have varying carbon chain lengths and degrees of saturation, although DGAT may demonstrate preferential activity towards certain molecules.

Like other members of the eukaryotic β-acyltransferase superfamily, eukaryotic DGAT polypeptides typically contain a FYxDWWN (SEQ ID NO:13) heptapeptide retention motif, as well as a histidine (or tyrosine)-serine-phenylalanine (H/YSF) tripeptide motif, as described in Zhongmin et al. (*Journal of Lipid Research,* 42:1282-1291, 2001) (herein incorporated by reference). The highly conserved FYxDWWN (SEQ ID NO:13) is believed to be involved in fatty Acyl-CoA binding.

DGAT enzymes utilized according to the present invention may be isolated from any organism, including eukaryotic and prokaryotic organisms. Eukaryotic organisms having a DGAT gene are well-known in the art, and include various animals (e.g., mammals, fruit flies, nematodes), plants, parasites, and fungi (e.g., yeast such as *S. cerevisiae* and *Schizosaccharomyces pombe*). Examples of prokaryotic organisms include certain actinomycetes, a group of Gram-positive bacteria with high G+C ratio, such as those from the representative genera *Actinomyces, Arthrobacter, Corynebacterium, Frankia, Micrococcus, Mocrimonospora, Mycobacterium, Nocardia, Propionibacterium, Rhodococcus* and *Streptomyces*. Particular examples of actinomycetes that have one or more genes encoding a DGAT activity include, for example, *Mycobacterium tuberculosis, M. avium, M. smegmatis, Micromonospora echinospora, Rhodococcus opacus, R. ruber*, and *Streptomyces lividans*. Additional examples of prokaryotic organisms that encode one or more enzymes having a DGAT activity include members of the genera *Acinetobacter*, such as *A. calcoaceticus, A. baumanii*, and *A. baylii*. In certain embodiments, a DGAT enzyme is isolated from *Acinetobacter baylii* sp. ADP1, a gram-negative triglyceride forming prokaryote, which contains a well-characterized DGAT (AtfA).

Fatty Acid Biosynthesis

Fatty acids are a group of negatively charged, linear hydrocarbon chains of various length and various degrees of oxidation states. The negative charge is located at a carboxyl end group and is typically deprotonated at physiological pH values (pK~2-3). The length of the fatty acid ‘tail’ determines its water solubility (or rather insolubility) and amphipathic characteristics. Fatty acids are components of phospholipids and sphingolipids, which form part of biological membranes, as well as triglycerides, which are primarily used as energy storage molecules inside cells Fatty acids are formed from acetyl-CoA and malonyl-CoA precursors. Malonyl-CoA is a carboxylated form of acetyl-CoA, and contains a 3-carbon dicarboxylic acid, malonate, bound to Coenzyme A. Acetyl-CoA carboxylase catalyzes the 2-step reaction by which acetyl-CoA is carboxylated to form malonyl-CoA. In particular, malonate is formed from acetyl-CoA by the addition of $CO_2$ using the biotin cofactor of the enzyme acetyl-CoA carboxylase.

Fally acid synthase (FAS) carries out the chain elongation steps of fatty acid biosynthesis. FAS is a large multienzyme complex. In mammals, FAS contains two subunits, each containing multiple enzyme activities. In bacteria and plants, individual proteins, which associate into a large complex, catalyze the individual steps of the synthesis scheme. For example, in bacteria and plants, the acyl carrier protein is a smaller, independent protein.

Fatty acid synthesis starts with acetyl-CoA, and the chain grows from the "tail end" so that carbon 1 and the alpha-carbon of the complete fatty acid are added last. The first reaction is the transfer of an acetyl group to a pantothenate group of acyl carrier protein (ACP), a region of the large mammalian fatty acid synthase (FAS) protein. In this reaction, acetyl CoA is added to a cysteine —SH group of the condensing enzyme (CE) domain: acetyl CoA+CE-cys-SH→acetyl-cys-CE+CoASH. Mechanistically, this is a two step process, in which the group is first transferred to the ACP (acyl carrier peptide), and then to the cysteine —SH group of the condensing enzyme domain.

In the second reaction, malonyl CoA is added to the ACP sulfhydryl group: malonyl CoA+ACP-SH→malonyl ACP+CoASH. This —SH group is part of a phosphopantethenic acid prosthetic group of the ACP.

In the third reaction, the acetyl group is transferred to the malonyl group with the release of carbon dioxide: malonyl ACP+acetyl-cys-CE→beta-ketobutyryl-ACP+$CO_2$.

In the fourth reaction, the keto group is reduced to a hydroxyl group by the beta-ketoacyl reductase activity: beta-ketobutyryl-ACP+NADPH+$H^+$→beta-hydroxybutyryl-ACP+$NAD^+$.

In the fifth reaction, the beta-hydroxybutyryl-ACP is dehydrated to form a trans-monounsaturated fatty acyl group by the beta-hydroxyacyl dehydratase activity: beta-hydroxybutyryl-ACP→2-butenoyl-ACP+$H_2O$.

In the sixth reaction, the double bond is reduced by NADPH, yielding a saturated fatty acyl group two carbons longer than the initial one (an acetyl group was converted to a butyryl group in this case): 2-butenoyl-ACP+NADPH+$H^+$→butyryl-ACP+$NADP^+$. The butyryl group is then transferred from the ACP sulfhydryl group to the CE sulfhydryl: butyryl-ACP+CE-cys-SH→ACP-SH+butyryl-cys-CE. This step is catalyzed by the same transferase activity utilized previously for the original acetyl group. The butyryl group is now ready to condense with a new malonyl group (third reaction above) to repeat the process. When the fatty acyl group becomes 16 carbons long, a thioesterase activity hydrolyses it, forming free palmitate: palmitoyl-ACP+$H_2O$→palmitate+ACP-SH. Fatty acid molecules can undergo further modification, such as elongation and/or desaturation.

Modified photosynthetic microorganisms, e.g., Cyanobacteria, may comprise one or more exogenous polynucleotides encoding any of the above polypeptides or enzymes involved in fatty acid synthesis. In particular embodiments, the enzyme is an acetyl-CoA carboxylase or a variant or functional fragment thereof.

As used herein, an "acetyl CoA carboxylase" gene of the present invention includes any polynucleotide sequence encoding amino acids, such as protein, polypeptide or peptide, obtainable from any cell source, which demonstrates the ability to catalyze the carboxylation of acetyl-CoA to produce malonyl-CoA under enzyme reactive conditions, and further includes any naturally-occurring or non-naturally occurring variants of an acetyl CoA carboxylase sequence having such ability.

Acetyl-CoA carboxylase (ACCase) is a biotin-dependent enzyme that catalyses the irreversible carboxylation of acetyl-CoA to produce malonyl-CoA through its two catalytic activities, biotin carboxylase (BC) and carboxyltransferase (CT). The biotin carboxylase (BC) domain catalyzes the first step of the reaction: the carboxylation of the biotin prosthetic group that is covalently linked to the biotin carboxyl carrier protein (BCCP) domain. In the second step of the reaction, the carboxyltransferase (CT) domain catalyzes the transfer of the carboxyl group from (carboxy) biotin to acetyl-CoA. Formation of malonyl-CoA by Acetyl-CoA carboxylase (ACCase) represents the commitment step for fatty acid synthesis, because malonyl-CoA has no metabolic role other than serving as a precursor to fatty acids. Because of this reason, acetyl-CoA Carboxylase represents a pivotal enzyme in the synthesis of fatty acids.

In most prokaryotes, ACCase is a multi-subunit enzyme, whereas in most eukaryotes it is a large, multi-domain enzyme. In yeast, the crystal structure of the CT domain of yeast ACCase has been determined at 2.7 A resolution (Zhang et al., *Science,* 299:2064-2067 (2003). This structure contains two domains, which share the same backbone fold. This fold belongs to the crotonase/ClpP family of proteins, with a b-b-a superhelix. The CT domain contains many insertions on its surface, which are important for the dimerization of ACCase. The active site of the enzyme is located at the dimer interface.

Although Cyanobacteria, such as *Synechococcus*, express a native ACCase enzyme, these bacteria typically do not produce or accumulate significant amounts of fatty acids. For example, *Synechococcus* in the wild accumulates fatty acids in the form of lipid membranes to a total of about 4% by dry weight.

Given the role of ACCase in the commitment step of fatty acid biosynthesis, embodiments of the present invention include methods of increasing the production of fatty acid biosynthesis, and, thus, lipid production, in Cyanobacteria by introducing one or more polynucleotides that encode an ACC enzyme that is exogenous to the Cyanobacterium's native genome. Embodiments of the present invention also include a modified Cyanobacterium, and compositions comprising said Cyanobacterium, comprising one or more polynucleotides that encode an ACCase enzyme that is exogenous to the Cyanobacterium's native genome.

A polynucleotide encoding an ACCase enzyme may be isolated or obtained from any organism, such as any prokaryotic or eukaryotic organism that contains an endogenous ACCase gene. Examples of eukaryotic organisms having an ACCase gene are well-known in the art, and include various animals (e.g., mammals, fruit flies, nematodes), plants, parasites, and fungi (e.g., yeast such as *S. cerevisiae* and *Schizosaccharomyces pombe*). In certain embodiments, the ACCase encoding polynucleotide sequence is obtained from *Saccharomyces cerevisiae.*

Examples of prokaryotic organisms that may be utilized to obtain a polynucleotide encoding an enzyme having ACCase activity include, but are not limited to, *Escherichia coli, Legionella pneumophila, Listeria monocytogenes, Streptococcus pneumoniae, Bacillus subtilis, Ruminococcus obeum* ATCC 29174, marine gamma proteobacterium HTCC2080, *Roseovarius* sp. HTCC2601, *Oceanicola granulosus* HTCC2516, *Bacteroides caccae* ATCC 43185, *Vibrio alginolyticus* 12G01, *Pseudoalteromonas tunicata* D2, *Marinobacter* sp. ELB17, marine gamma proteobacterium HTCC2143, *Roseobacter* sp. SK209-2-6, *Oceanicola batsensis* HTCC2597, *Rhizobium leguminosarum* bv. *trifolii* WSM1325, *Nitrobacter* sp. Nb-311A, *Chloroflexus aggregans* DSM 9485, *Chlorobaculum parvum, Chloroherpeton thalassium, Acinetobacter baumannii, Geobacillus*, and *Stenotrophomonas maltophilia*, among others.

Polynucleotides and Vectors

The present invention includes modified photosynthetic microorganisms comprising one or more exogenous polynucleotides encoding a polypeptide associated with triglyceride or fatty acid biosynthesis, or a variant or a functional fragment thereof. Accordingly, the present invention utilizes isolated polynucleotides that encode the various triglyceride and lipid biosynthesis enzymes utilized herein, such as diacylglycerol acyltransferase, phosphatidate phosphatase, and acetyl-CoA carboxylase, in addition to nucleotide sequences that encode any functional naturally-occurring variants or fragments (i.e., allelic variants, orthologs, splice variants) or non-naturally occurring variants or fragments of these native enzymes (i.e., optimized by engineering), as well as compositions comprising such polynucleotides, including, e.g., cloning and expression vectors.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a diacylglycerol acyltransferase, a phosphatidate phosphatase, an acetyl-CoA carboxylase, or a portion thereof) or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide. The effect on the enzymatic activity of the encoded polypeptide may generally be assessed as described herein.

In certain embodiments of the present invention, a polynucleotide encodes a DGAT comprising of consisting of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd. In certain embodiments of the present invention, a DGAT polynucleotide comprises or consists of a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd. DGATn and DGATd correspond to *Acinetobacter baylii* DGAT and a modified form thereof, which includes two additional amino acid residues immediately following the initiator methionine.

In certain embodiments of the present invention, a polynucleotide encodes a phosphatidate phosphatase comprising or consisting of a polypeptide sequence set forth in SEQ ID NO:2, or a fragment or variant thereof. In particular embodiments, a phosphatidate phosphatase polynucleotide comprises or consists of a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPah1), and SEQ ID NO:5 is a codon-optimized for expression in Cyanobacteria sequence that encodes yPAH1.

In certain embodiments of the present invention, a polynucleotide encodes an acetyl-CoA carboxylase (ACCase) comprising or consisting of a polypeptide sequence set forth in any of SEQ ID NOs:3, 20, 21, 22, 23, or 28, or a fragment or variant thereof. In particular embodiments, a ACCase polynucleotide comprises or consists of a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yACC1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *Triticum aestivum* ACCase; and SEQ ID NO:29 encodes this *Triticum aestivum* ACCase.

In certain embodiments, the present invention provides isolated polynucleotides comprising various lengths of contiguous stretches of sequence identical to or complementary to a diacylglycerol acyltransferase, a phosphatidate phosphatase, or an acetyl-CoA carboxylase, wherein the isolated polynucleotides encode a biologically active, truncated enzyme.

Exemplary nucleotide sequences that encode the enzymes of the application encompass full-length diacylglycerol acyltransferases, phosphatidate phosphatases, and/or acetyl-CoA carboxylases, as well as portions of the full-length or substantially full-length nucleotide sequences of these genes or their transcripts or DNA copies of these transcripts. Portions of a nucleotide sequence may encode polypeptide portions or segments that retain the biological activity of the reference polypeptide. A portion of a nucleotide sequence that encodes a biologically active fragment of an enzyme provided herein may encode at least about 20, 21, 22, 23, 24, 25, 30, 40, 50, 60, 70, 80, 90, 100, 120, 150, 200, 300, 400, 500, 600, or more contiguous amino acid residues, almost up to the total number of amino acids present in a full-length enzyme. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the nucleotide sequences of the diacylglycerol acyltransferases, phosphatidate phosphatases, and acetyl-CoA carboxylases utilized according to methods and compositions provided herein. Nucleic acid variants can be naturally-occurring, such as allelic variants (same locus), homologs (different locus), and orthologs (different organism) or can be non naturally-occurring. Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having a diacylglycerol acyltransferase activity, a phosphatidate phosphatase activity, and/or a acetyl-CoA carboxylase activity. Embodiments of the present invention, therefore, encompass cyanobacteria comprising such naturally occurring polynucleotide variants.

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in Cyanobacteria, such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide, such as a polypeptide having either a diacylglycerol acyltransferase activity, a phosphatidate phosphatase activity, or a acetyl-CoA carboxylase activity. Generally, variants of a particular reference nucleotide sequence will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

Known diacylglycerol acyltransferase, phosphatidate phosphatase, and/or acetyl-CoA carboxylase nucleotide sequences can be used to isolate corresponding sequences and alleles from other organisms, particularly other microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other reference coding sequences present in a population of cloned genomic DNA fragments or cDNA fragments (i.e., genomic or cDNA libraries) from a chosen organism.

Accordingly, the present invention also contemplates polynucleotides that hybridize to reference diacylglycerol acyltransferase, phosphatidate phosphatase, or a acetyl-CoA carboxylase nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a diacylglycerol acyltransferase enzyme, a phosphatidate phosphatase enzyme, or a acetyl-CoA carboxylase enzyme is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization.

Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m$=81.5+16.6 ($\log_{10}$ M)+0.41 (% G+C)−0.63 (% formamide)−(600/length) wherein: M is the concentration of $Na^+$, preferably in the range of 0.01 molar to 0.4 molar; % G+C is the sum of guano sine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5× Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of an triglyceride or lipid biosynthesis enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized."

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. The polynucleotides of the present invention will typically be introduced and expressed in cyanobacterial systems. As such, the present invention contemplates the use of vector and plasmid systems having regulatory sequences (e.g., promoters and enhancers) that are suitable for use in various cyanobacteria (see, e.g., Koksharova et al. *Applied Microbiol Biotechnol* 58:123-37, 2002). For example, the promiscuous RSF1010 plasmid provides autonomous replication in several cyanobacteria of the genera *Synechocystis* and *Synechococcus* (see, e.g., Mermet-Bouvier et al., *Curr Microbiol* 26:323-327, 1993). As another example, the pFC1 expression vector is based on the promiscuous plasmid RSF1010. pFC1 harbors the lambda c1857 repressor-encoding gene and pR promoter, followed by the lambda cro ribosome-binding site and ATG translation initiation codon (see, e.g., Mermet-Bouvier et al., *Curr Microbiol* 28:145-148, 1994). The latter is located within the unique NdeI restriction site (CATATG) of pFC1 and can be exposed after cleavage with this enzyme for in-frame fusion with the protein-coding sequence to be expressed.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. Generally, it is well-known that strong *E. coli* promoters work well in Cyanobacteria. Also, when cloning in cyanobacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. Other vectors containing IPTG inducible promoters, such as pAM1579 and pAM2991trc, may be utilized according to the present invention.

Certain embodiments may employ a temperature inducible system. As one example, an operon with the bacterial phage left-ward promoter ($P_L$) and a temperature sensitive repressor gene CI857 may be employed to produce a temperature inducible system for producing fatty acids and/or triglycerides in Cyanobacteria (see, e.g., U.S. Pat. No. 6,306,639, herein incorporated by reference). It is believed that at a non-permissible temperature (low temperature, 30 degrees Celsius), the repressor binds to the operator sequence, and thus prevents RNA polymerase from initiating transcription at the $P_L$ promoter. Therefore, the expression of encoded gene or genes is repressed. When the cell culture is transferred to a permissible temperature (37-42 degrees Celsius), the repressor can not bind to the operator. Under these conditions, RNA polymerase can initiate the transcription of the encoded gene or genes.

In cyanobacterial systems, a number of expression vectors may be selected depending upon the use intended for the expressed polypeptide. When large quantities are needed, vectors which direct high level expression of encoded proteins may be used. For example, overexpression of ACCase enzymes may be utilized to increase fatty acid biosynthesis. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST).

Certain embodiments may employ Cyanobacterial promoters or regulatory operons. In certain embodiments, a promoter may comprise an rbcLS operon of *Synechococcus*, as described, for example, in Ronen-Tarazi et al. (*Plant Physiology* 18:1461-1469, 1995), or a cpc operon of *Synechocystis* sp. strain PCC 6714, as described, for example, in Imashimizu et al. (*J Bacteriol.* 185:6477-80, 2003). In certain embodiments, the tRNApro gene from *Synechococcus* may also be utilized as a promoter, as described in Chungjatupornchai et al. (*Curr Microbiol.* 38:210-216, 1999). Certain embodiments may employ the nirA promoter from *Synechococcus* sp. strain PCC 7942, which is repressed by ammonium and induced by nitrite (see, e.g., Maeda et al., *J. Bacteriol.* 180:4080-4088, 1998; and Qi et al., *Applied and Environmental Microbiology* 71:5678-5684, 2005). The efficiency of expression may be enhanced by the inclusion of enhancers which are appropriate for the particular cyanobacterial cell system which is used, such as those described in the literature.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983). The presence of a desired polynucleotide, such as a diacylglycerol acyltransferase, phosphatidate phosphatase, and/or an acetyl-CoA carboxylase encoding polypeptide, may also be confirmed by PCR.

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Cyanobacterial host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct localization of the encoded polypeptide to a desired site within the cell. Other recombinant constructions may be used to join sequences encoding a polypeptide of interest to nucleotide sequence encoding a polypeptide domain which will direct secretion of the encoded protein.

Polypeptides

Embodiments of the present invention contemplate the use of modified photosynthetic microorganisms, e.g., Cyanobacteria, comprising polypeptides having a diacylglycerol acyltransferase activity, a phosphatidate phosphatase activity, and/or an acetyl-CoA carboxylase activity, including truncated, variant and/or modified polypeptides thereof, for increasing lipid production and/or producing triglycerides said Cyanobacteria.

In certain embodiments of the present invention, a DGAT polypeptide comprises or consists of a polypeptide sequence set forth in any one of SEQ ID NOs:1, 14, 15, or 18, or a fragment or variant thereof. SEQ ID NO:1 is the sequence of DGATn; SEQ ID NO: 14 is the sequence of *Streptomyces coelicolor* DGAT (ScoDGAT or SDGAT); SEQ ID NO:15 is the sequence of *Alcanivorax borkumensis* DGAT (AboDGAT); and SEQ ID NO:18 is the sequence of DGATd. In certain embodiments of the present invention, a DGAT polypeptide is encoded by a polynucleotide sequence set forth in any one of SEQ ID NOs:4, 7, 16, 17, or 19, or a fragment or variant thereof. SEQ ID NO:4 is a codon-optimized for expression in Cyanbacteria sequence that encodes DGATn; SEQ ID NO: 7 has homology to SEQ ID NO:4; SEQ ID NO:16 is a codon-optimized for expression in Cyanobacteria sequence that encodes ScoDGAT; SEQ ID NO:17 is a codon-optimized for expression in Cyanobacteria sequence that encodes AboDGAT; and SEQ ID NO:19 is a codon-optimized for expression in Cyanobacteria sequence that encodes DGATd.

In certain embodiments of the present invention, a phosphatidate phosphatase polypeptide comprises or consists of a polypeptide sequence set forth in SEQ ID NO:2, or a fragment or variant thereof. In particular embodiments, a phosphatidate phosphatase is encoded by a polynucleotide sequence set forth in SEQ ID NO:5 or SEQ ID NO:8, or a fragment or variant thereof. SEQ ID NO:2 is the sequence of *Saccharomyces cerevisiae* phosphatidate phosphatase (yPah1), and SEQ ID NO:5 is a codon-optimized for expression in Cyanobacteria sequence that encodes yPAH1.

In certain embodiments of the present invention, an acetyl-CoA carboxylase (ACCase) polypeptide comprises or consists of a polypeptide sequence set forth in any of SEQ ID NOs:3, 20, 21, 22, 23, or 28, or a fragment or variant thereof. In particular embodiments, an ACCase polypeptide is encoded by a polynucleotide sequence set forth in any of SEQ ID NOs:6, 9, 24, 25, 26, 27, or 29, or a fragment or variant thereof. SEQ ID NO:3 is the sequence of *Saccharomyces cerevisiae* acetyl-CoA carboxylase (yAcc1); and SEQ ID NO:6 is a codon-optimized for expression in Cyanobacteria sequence that encodes yAcc1. SEQ ID NO:20 is *Synechococcus* sp. PCC 7002 AccA; SEQ ID NO:21 is *Synechococcus* sp. PCC 7002 AccB; SEQ ID NO:22 is *Synechococcus* sp. PCC 7002 AccC; and SEQ ID NO:23 is *Synechococcus* sp. PCC 7002 AccD. SEQ ID NO:24 encodes *Synechococcus* sp. PCC 7002 AccA; SEQ ID NO:25 encodes *Synechococcus* sp. PCC 7002 AccB; SEQ ID NO:26 encodes *Synechococcus* sp. PCC 7002 AccC; and SEQ ID NO:27 encodes *Synechococcus* sp. PCC 7002 AccD. SEQ ID NO:28 is a *T. aestivum* ACCase; and SEQ ID NO:29 encodes this *Triticum aestivum* ACCase.

Variant proteins encompassed by the present application are biologically active, that is, they continue to possess the enzymatic activity of a reference polypeptide. Such variants may result from, for example, genetic polymorphism or from human manipulation. Biologically active variants of a reference diacylglycerol acyltransferase, phosphatidate phosphatase, and/or acetyl-CoA carboxylase polypeptide fragment will have at least 40%, 50%, 60%, 70%, generally at least 75%, 80%, 85%, usually about 90% to 95% or more, and typically about 98% or more sequence similarity or identity with the amino acid sequence for a reference protein as determined by sequence alignment programs described elsewhere herein using default parameters. A biologically active variant of a reference polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a variant polypeptide differs from the reference sequences in SEQ ID NOS: 1, 2, 3, 6, 8, 10, 12, and 14 by at least one but by less than 15, 10 or 5 amino acid residues. In other embodiments, it differs from the reference sequences by at least one residue but less than 20%, 15%, 10% or 5% of the residues.

A diacylglycerol acyltransferase, phosphatidate phosphatase, or acetyl-CoA carboxylase polypeptide may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of diacylglycerol acyltransferase, phosphatidate phosphatase, and/or acetyl-CoA carboxylase polypeptides. Recursive ensemble mutagenesis (REM), a technique which enhances the frequency of functional mutants in the libraries, can be used in combination with the screening assays to identify polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Polypeptide variants may contain conservative amino acid substitutions at various locations along their sequence, as compared to a reference amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant polypeptide can readily be determined by assaying its enzymatic activity, as described herein (see, e.g., Example 3). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a diacylglycerol acyltransferase, phosphatidate phosphatase, or acetyl-CoA carboxylase polypeptide is typically replaced with another amino acid residue from the same side chain family. Alternatively, mutations can be introduced randomly along all or part of a coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference polypeptide, results in abolition of an activity of the parent molecule such that less than 20% of the wild-type activity is present. For example, such essential amino acid residues include those that are conserved in diacylglycerol acyltransferase, phosphatidate phosphatase, or acetyl-CoA carboxylase polypeptides across different species, including those sequences that are conserved in the enzymatic sites of polypeptides from various sources.

Accordingly, the present invention also contemplates variants of the naturally-occurring diacylglycerol acyltransferase, phosphatidate phosphatase, or acetyl-CoA carboxylase polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference polypeptide sequence. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of a parent or reference polypeptide sequence are contemplated.

In some embodiments, variant polypeptides differ from a reference diacylglycerol acyltransferase, phosphatidate phosphatase, or acetyl-CoA carboxylase polypeptide sequence by at least one but by less than 50, 40, 30, 20, 15, 10, 8, 6, 5, 4, 3 or 2 amino acid residue(s). In other embodiments, variant polypeptides differ from a reference by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of a diacylglycerol acyltransferase, phosphatidate phosphatase, or acetyl-CoA carboxylase reference polypeptide, and retains the enzymatic activity of that reference polypeptide.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989*, Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990*, J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997*, Nucleic Acids Res,* 25: 3389-3402). When utilizing BLAST and Gapped BLAST programs, the default parameters of the respective programs (e.g., XBLAST and NBLAST) can be used.

Variants of a diacylglycerol acyltransferase, phosphatidate phosphatase, or acetyl-CoA carboxylase reference polypeptide can be identified by screening combinatorial libraries of mutants of a reference polypeptide. Libraries or fragments e.g., N terminal, C terminal, or internal fragments, of protein coding sequence can be used to generate a variegated population of fragments for screening and subsequent selection of variants of a reference polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of polypeptides.

The present invention also contemplates the use of chimeric or fusion proteins for increasing lipid production and/or producing triglycerides. As used herein, a "chimeric protein" or "fusion protein" includes a diacylglycerol acyltransferase, phosphatidate phosphatase, or acetyl-CoA carboxylase reference polypeptide or polypeptide fragment linked to either another reference polypeptide (e.g., to create multiple fragments), to a non-reference polypeptide, or to both. A "non-reference polypeptide" refers to a "heterologous polypeptide" having an amino acid sequence corresponding to a protein which is different from the diacylglycerol acyltransferase, phosphatidate phosphatase, or acetyl-CoA carboxylase protein sequence, and which is derived from the same or a different organism. The reference polypeptide of the fusion protein can correspond to all or a portion of a biologically active amino acid sequence. In certain embodiments, a fusion protein includes at least one (or two) biologically active portion of an diacylglycerol acyltransferase, phosphatidate phosphatase, or acetyl-CoA carboxylase protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the enzymatic activity of the polypeptide. For example, in one embodiment, a fusion partner may comprise a sequence that assists in expressing the protein (an expression enhancer) at higher yields than the native recombinant protein. Other fusion partners may be selected so as to increase the solubility or stability of the protein or to enable the protein to be targeted to desired intracellular compartments.

The fusion protein can include a moiety which has a high affinity for a ligand. For example, the fusion protein can be a GST-fusion protein in which the diacylglycerol acyltransferase, phosphatidate phosphatase, or acetyl-CoA carboxylase sequences are fused to the C-terminus of the GST sequences. Such fusion proteins can facilitate the purification and/or identification of the resulting polypeptide. Alternatively, the fusion protein can be a diacylglycerol acyltransferase, phosphatidate phosphatase, or acetyl-CoA carboxylase protein containing a heterologous signal sequence at its N-terminus. In certain host cells, expression and/or secretion of such proteins can be increased through use of a heterologous signal sequence.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Generation of DGAT and PAP-Expressing Cyanobacteria

*Acinetobacter baylii* sp. ADP1, a gram-negative TAG forming prokaryote, contains a well-characterized DGAT (AtfA, also referred to herein as ADP1-DGAT). The ADP1-DGAT nucleotide sequence was synthesized and codon optimized for *Selongatus* PCC 7942 expression using DNA2.0, received in a plasmid, subcloned using established molecular biology techniques into the IPTG-inducible vector pAM2991trc (this vector contains sequences encoding the tact transcriptional repressor, and the pTrc promoter which is repressed by LacI), and recombined into neutral site 1 (NS1) of *S. elongatus* PCC 7942. Colonies were selected from BG11-spec/strep plates, restreaked for isolation, and tested by PCR for positive colonies. Inducible transcription of the gene was verified by real-time PCR

*Saccharomyces cerevisiae* contains three characterized phosphatidate phosphatases, one of which is a soluble, non-integral membrane protein, Pah1p (YMR165C). Pah1 plays a major role in the synthesis of TAGs and phospholipids in *S. cerevisiae*. The Pah1 nucleotide sequence was synthesized and codon optimized for *S. elongatus* PCC 7942 expression using DNA2.0, received in a plasmid, subcloned using established molecular biology techniques into the IPTG-inducible vector pAM2991trc, and recombined into neutral site 1 (NS1) of *S. elongatus* PCC 7942. Colonies were selected from BG11-spec/strep plates, restreaked for isolation, and tested by PCR for positive colonies.

A *S. elongatus* PCC 7942 strain expressing both the ADP1-DGAT and Pah1 genes described above was generated by transforming an ADP1-DGAT expressing strain (ADP1-DGAT subcloned into IPTG-inducible vector pAM1579trc-kanamycin, which recombined in NS2) with the construct carrying Pah1 from NS1 (described above) and selecting transformants on plates containing kanamycin, streptomycin and spectinomycin. Inducible transcription of these genes was verified by real-time PCR.

Example 2

Generation of DGAT and ACCase-Expressing Cyanobacteria

*Synechococcus* sp. PCC 7002 contains fours genes encoding the four subunits of bacterial acetyl coenzyme A carboxylase (7002 acc). These genes (accA, accB, accC, and accD) were PCR amplified and two synthetic two-gene operons were constructed using splicing by overlap extenstion PCR techniques. Synthetic operon 1 contains accAD and synthetic operon 2 contains accBC. The two synthetic operons were cloned into vector pTG2087 (pAM2314Ftrc3.) The vector pTG2087 contains regions of homology for recombination into neutral site 1 (NS1) of *S. elongatus* PCC7942, sequences encoding the lacl transcriptional repressor, and the pTrc promoter which is repressed by LacI. Synthetic 7002 acc operons 1 and 2 were cloned into pTG2087, in two separate sites, under control of the pTrc promoter to generate plasmid pTG2087-7002acc. Clone candidates were sequenced to confirm that there were no PCR-induced mutations in the coding sequence of any of the 7002 acc genes.

pTG2087-7002acc was transformed into *S. elongatus* PCC 7942 and recombinants into NS1 were selected by plating on BG11 media containing spectinomycin and streptomycin. Transformants that grew out in the presence of antibiotic were streaked for isolated colonies and single colonies were tested for the presence of the 7002 acc genes in NS1 by PCR. Inducible transcription of the 7002 acc genes was verified by real-time PCR.

Functional expression of the 7002 acc genes was tested by the ability to complement a deletion of the endogenous *S. elongatus* PCC 7942 accD gene. *S. elongatus* PCC7942 with synthetic operon 1 (7002 accAD) recombined into NS1 was tested for the ability to complement loss of the native *S. elongatus* accD gene. Successful complementation indicated that the 7002 acc genes were functionally expressed in *S. elongatus* PCC7942.

The *S. elongatus* PCC7942-7002 accADBC strain was transformed with vectors containing one of two DGAT genes (either ADP1-DGAT or ScoDGAT from examples 1 and 7) for recombination into NS2. Transformants were selected by plating on media containing kanamycin. The recombination of ADP1-DGAT or ScoDGAT into NS2 was confirmed by PCR. These strains were tested for triglyceride production using the methods described in examples 3 and 4.

*S. cerevisiae* contains one characterized gene encoding an acetyl-CoA carboxylase (yAcc1), which was isolated from *S. cerevisiae*, codon optimized for *S. elongatus* PCC 7942 expression using DNA2.0, received as a plasmid and subcloned into an IPTG-inducible vector pAM2991 generating vector pTG2035. This vector was recombined into neutral site 1 (NS1) of *S. elongatus* PCC 7942 containing the ADP1-DGAT gene from example 1 recombined into NS2. Colonies were selected from a BG11-spectinomycin and streptomycin plate, restreaked for isolation, and tested by PCR for positive clones. These strains were tested for triglyceride production using the methods described in examples 3 and 4.

Example 3

Increased Fatty Acid Production in Cyanobacteria

ADP1-DGAT-expressing Cyanobacteria from Example 1 was tested for the ability to produce increased levels of fatty acids. Induction of ADP1-DGAT positive clones was carried out by the addition of 1 mM IPTG when culture reached an OD750=0.2. Samples were taken at 24 hours after induction, and analyzed for lipid content by gas chromatography (GC).

As seen in FIG. 1, GC results showed a 2-fold increase in lipid content for IPTG-induced DGAT compared to un-induced vector control.

Example 4

Triglyceride Production in Cyanobacteria and TLC Analysis of DGATs

Several enzymes with acylCoA: diacylglycerol acyltransferase activity have been described in the literature, and a number of homologs were identified by conducting homology searches of publicly available DNA and protein databases. Several DGAT homologs were synthesized, optimized for expression in *Synechoccocus elontatus* PCC 7942, and integrated into its genome via homologous recombination as described in Example 1.

A modified version of ADP1-DGAT from Example 1 was cloned into vector pTG2087 (pAM2314Ftrc3), a neutral site 1 expression vector described in Example 2. In this version, the 6 bases immediately following the ATG start codon of the ADP1-DGAT gene from Example 1 were deleted. This strain was named ADP1-DGATn.

*Streptomyces coelicolor* is a gram-positive TAG forming prokaryote that contains a well-characterized DGAT. The *Streptomyces*-DGAT (ScoDGAT) nucleotide sequence was synthesized and codon optimized for *S. elongatus* PCC 7942 expression using DNA2.0. The gene was received in a plasmid, subcloned using established molecular biology techniques into pTG2087 (pAM2314Ftrc3), a neutral site 1 expression vector described in Example 2, and recombined into neutral site 1 (NS1) of *S. elongatus* PCC 7942. Colonies were selected from BG11-spec/strep plates, restreaked for isolation and tested by PCR for positive colonies. Inducible transcription of this gene was verified by real-time PCR.

*Alcanivorax borkumensis* is a marine protobacteria gamma TAG forming prokaryote that contains a well-characterized DGAT (atfA1). The *Alcanivorax*-DGAT (AboDGAT) nucleotide sequence was synthesized and codon optimized for *S. elongatus* PCC 7942 expression using DNA2.0. The gene was received in a plasmid, subcloned using established molecular biology techniques into pTG2087 (pAM2314Ftrc3), a neutral site 1 expression vector described in Example 2, and recombined into neutral site 1 (NS1) of *S. elongatus* PCC 7942. Colonies were selected from BG11-spec/strep plates, restreaked for isolation and tested by PCR for positive colonies. Inducible transcription of this gene was verified by real-time PCR.

Induction experiments for ADP1-DGAT, ADP1-DGATn, ScoDGAT and AboDGAT were performed as described in Example 3. Samples were collected at 24 hours post-induction, and total lipid extracts were prepared for TLC analysis as follows. Pellets were resuspended in 100 ul of water, to which 375 ul of a 1:2 mixture of chloroform to methanol was added. Cells were extracted with frequent vortexing for 10 minutes. To this was added 125 ul of chloroform, and the extract was vortexed for another minute. Finally, phase separation was produced by adding 125 ul of 1M NaCl, with another 1 minute of vortexing. To speed separation, the samples were centrifuged in a clinical centrifuge for 10 minutes at an rcf of 1930. The organic phase was removed to a new tube and dried down in a vacuum dryer. The dry lipid extract was resuspended in 40 ul of a 2:1 chloroform:methanol mixture, and either a 6 ul aliquot or the entire volume was applied to TLC plates (200-um thick silica plates). Chromatography was run using a mobile phase comprised of 75% n-hexane, 25% diethylether acidified with 1 ml of glacial acetic acid per 100 ml solvent mixture. Completed runs were dried, and the lipids were imaged with primuline (50 mg/L dissolved in an 80% acetone solution). Images were recorded digitally using a hand-held UV lamp to excite the primuline stained plate.

Figure 2:
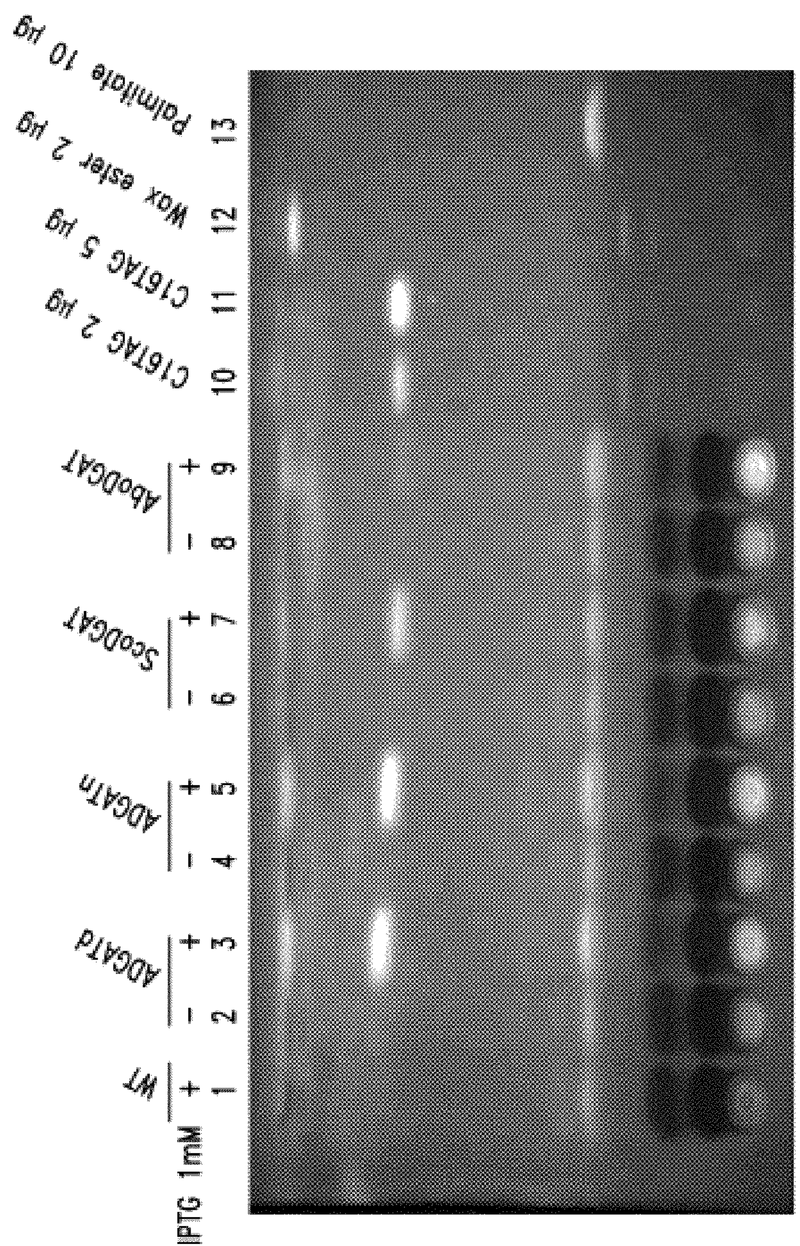
FIG. 2 shows a thin layer chromatography assay of triacylglceride (TAG) and fatty acids present in extracts obtained from *S. elongatus* PCC 7942 strains that carried one of four different DGATs (ADGATd, ADGATn, ScoDGAT, or AboDGAT) or a vector control, either uninduced or induced with IPTG. Control TAG (C16TAG) and fatty acid (palmitate) standards are also shown.

As shown in FIG. 2, all four DGAT genes resulted in TAG production when expressed in Cyanobacteria. Moreover, increases in fatty acids were observed in ADP1-DGAT, ADP1-DGATn, and AboDGAT expressing strains but not in ScoDGAT. These results demonstrate that heterologous expression of several DGATs in Cyanobacteria results in TAG formation.

Example 5

Triacylglceride and Free Fatty Acid Accumulation in *S. elongatus*

Figure 3:
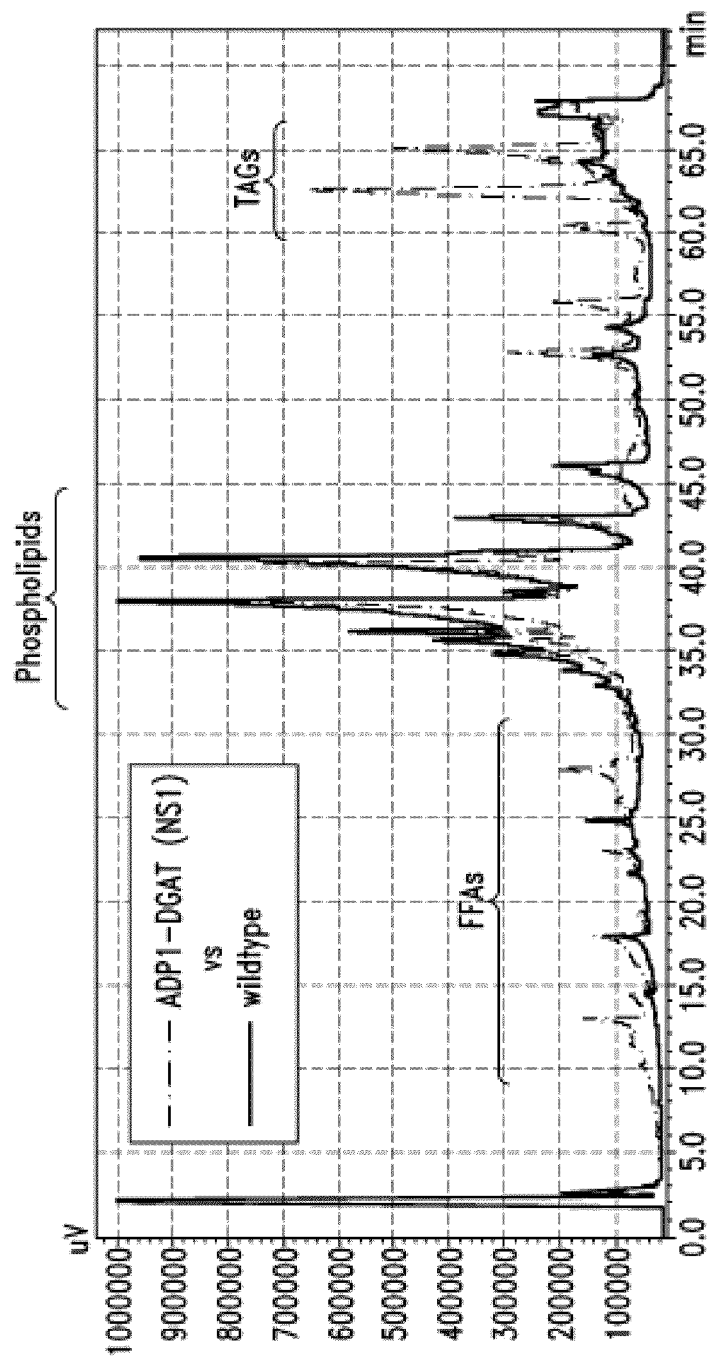
FIG. 3 is a graph showing the results of HPLC analysis of lipid extracts from *S. elongatus* PCC7942 expressing ADGATd (dashed line) as compared to wild type *S. elongatus* (solid line) following induction. The y-axis indicates the intensity of the peaks for the different lipid species, free fatty acids (FFAs), phospholipids, and TAGs, and the x-axis indicates the corresponding retention time.

The *S. elongatus* PCC 7942 ADP1-DGAT expressing strain described in Example 1 was grown under induction conditions as described in Example 3, and total lipid extracts prepared as described in Example 4 were subjected to HPLC analysis. 40 microL of total lipid extracts were analyzed on a Shimadzu Prominence UFLC (Ultra Fast Liquid Chromatograph) connected to an ESA Bioscience Corona CAD Plus detector (Charged Aerosol Detector). A Hypersil Gold C8 3 μm 150×4.6 mm column at 0.8 mL/min flow rate was used. A binary gradient system with mobile phase A: methanol/water/acetic acid (750:250:4) and mobile phase B: acetonitrile/methanol/THF/acetic acid (500:375:125:4) was used. The results of a typical run are shown in FIG. 3, in which the y axis indicates the intensity of the peaks for the different lipid species, and the x axis indicates the corresponding retention time. Three major lipid groups, free fatty acids (FFAs), phospholipids, and TAGs are shown, as indentified using representative standards of these lipid species (not shown). As can be seen, the induced strain produced TAGs. In the un-induced strain, these were undetectable. Thus, exogenous expression of DGAT in cyanobacteria results in TAG formation, as shown by TLC.

Example 6

Acyl Chain Composition of TAGs

Figure 4B:
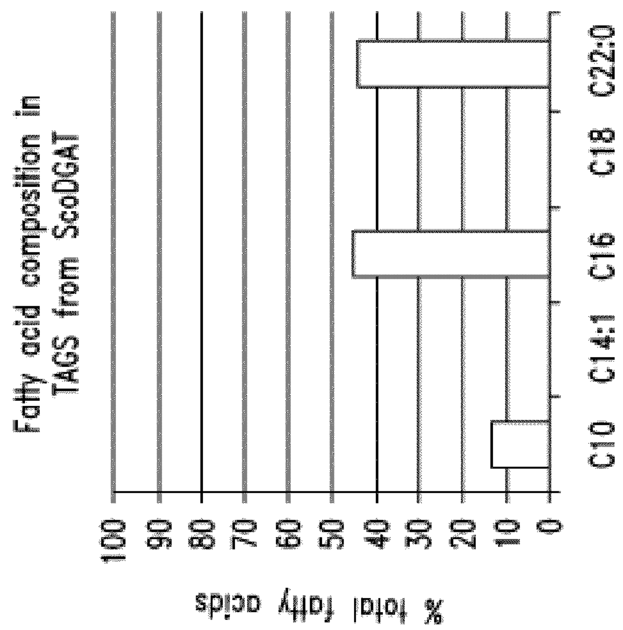
FIGS. 4A-4B provide graphs showing the acyl chain composition of TAGs produced by *S. elongatus* PCC7942 expressing ADP1-DGAT or ScoDGAT following induction, as determined by gas chromatography of TAGs isolated by TLC.
Figure 4A:
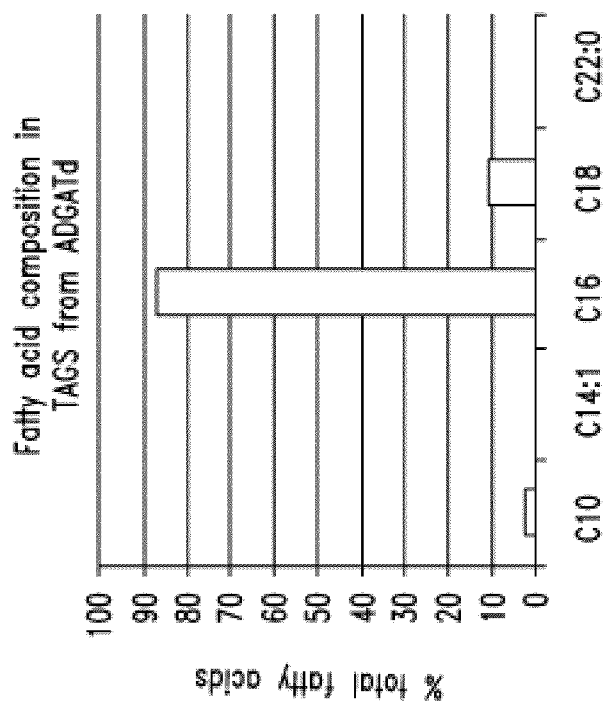

The ADP1-DGAT and ScoDGAT strains described in Example 1 and 4 were induced for TAG production as described in Example 3. Lipid extracts were prepared, and the non polar lipids were separated on a TLC as per the method described in Example 4. The spots on the TLC plate corresponding to TAGs, as determined by their co-migration with corresponding standards, were extracted from the TLC plates by cutting out a rectangular area encompassing each spot. This material was then subjected to transesterification and GC analysis. As can be seen in FIG. 4, the fatty acid composition of the TAGS produced by these two strains differed in that the TAGs produced by the ADP1-DGAT strain consisted of mixtures of C18 and C16 acyl chains (FIG. 4A), whereas the TAGs from ScoDGAT consisted of mixtures of C16 and C22 acyl chains (FIG. 4B). This highlights the different acyl change specificities of these two DGAT enzymes and supports the introduction of two or more different DGATs into modified Cyanobacteria to generate multiple different TAGs.

Example 7

Triacylglyceride Production in Cyanobacteria

A gene encoding a DGAT was introduced into a different strain, *Synechcocystis* sp. strain PCC 6803 (hereafter referred to as PCC 6803), to determine if DGAT expression correlated with TAG production outside of *S. elongatus* PCC 7942. Two mutants were constructed in *Synechocystis* sp. strain PCC 6803. The first mutant carried a gene encoding ADP1-DGAT under control of the Ptrc promoter, a locus encoding kanamycin resistance (nptA) and the lactose repressor (lacl). As a negative control, a strain was constructed that carried nptA and lacl, but not the ADP1-DGAT gene. Both constructs were built in a neutral site vector devised for use in PCC 6803.

This vector directs recombination into a neutral site in PCC 6803, a region between two convergently transcribed native genes that have been described in the literature as non-essential. The mutagenesis generally followed the protocols of Eaton-Rye (Methods in Molecular Biology, Vol 24, p 309-323), except that transformants were plated on plain BG-11 plates and subjected to increasing kanamycin concentrations by injecting concentrated kanamycin under the agar pad at 12 and 36 hours. Successful incorporation of the ADP1-DGAT gene was demonstrated using colony PCR. The plates used for mutagenesis were comprised of 1×BG-11 (Pasteur formulation), 1.25% Bactoagar, and sodium thiosulfate to 3 g/L.

Transformants confirmed to have the correct insertions were grown to late exponential phase, aliquots of the cultures were centrifuged, washed in BG-11, re-pelleted, and resuspended to 50 ml of BG-11 with kanamycin. Half the cultures were induced with IPTG at a final concentration of 1 mM. Typically, samples were taken at 0, 3 and 6 days of induction. Pelleted samples were stored at −80° C.

Figures 5A, 5B:
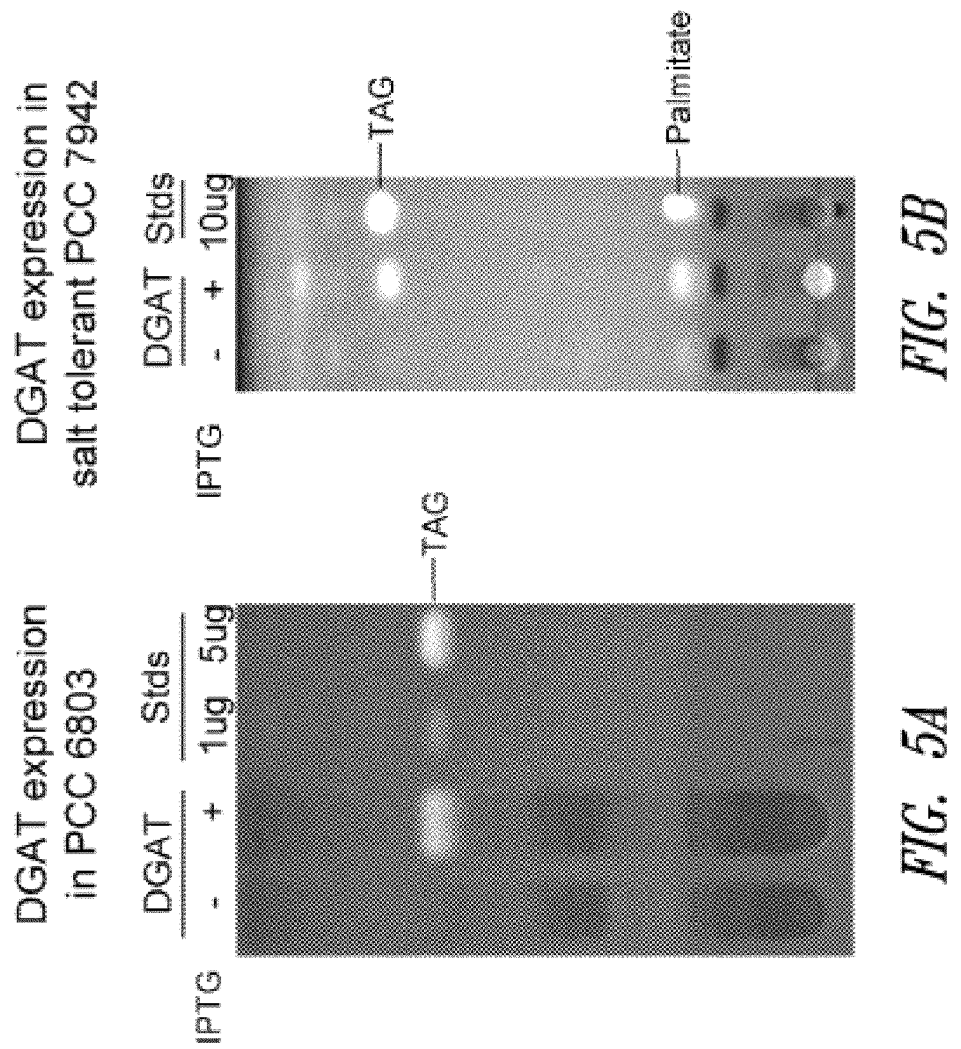
FIGS. 5A-5B show thin layer chromatography assays of triacylglceride (TAG) obtained from two different strains that carried ADP1-DGAT.
Figure 6:
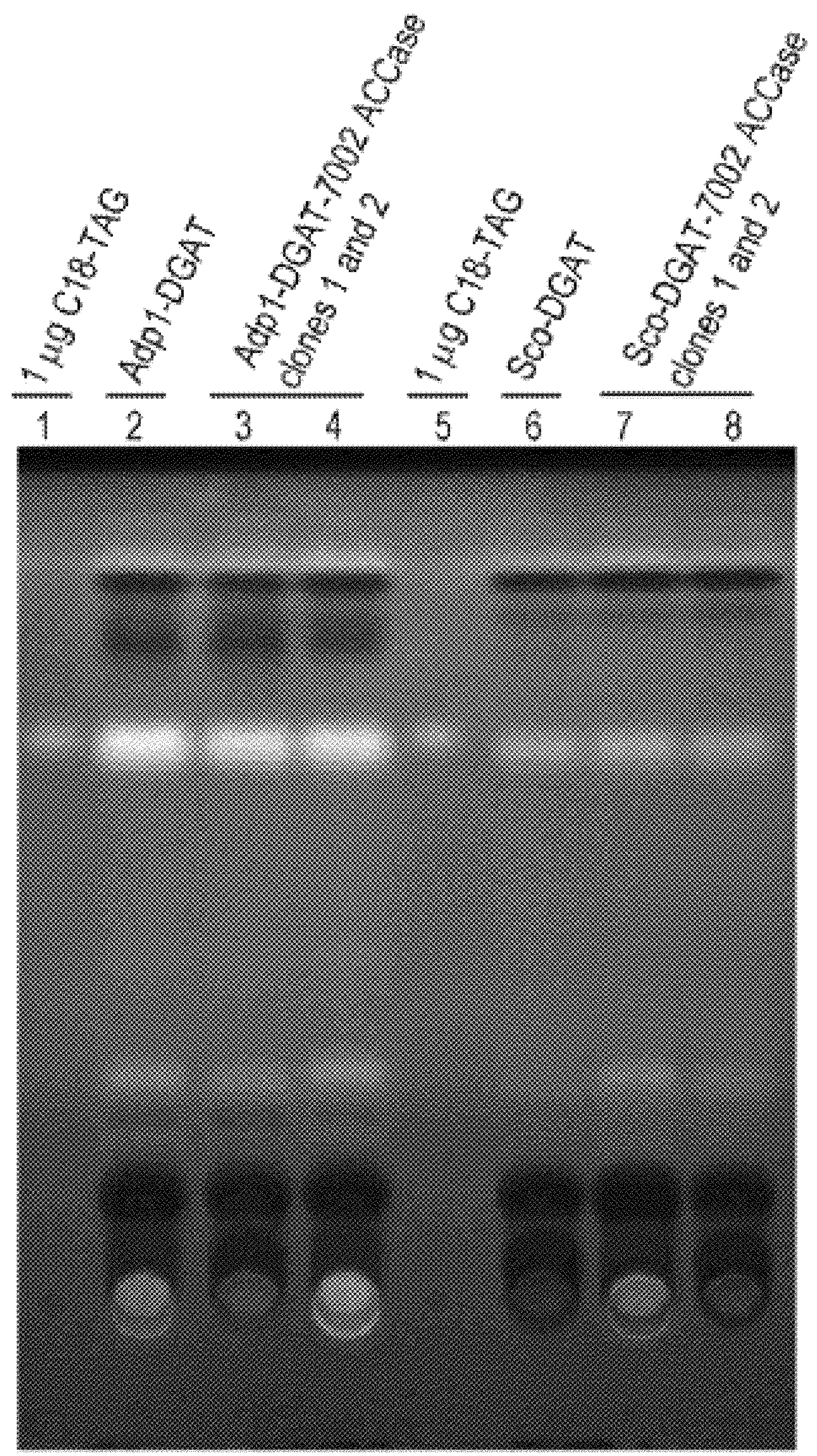
FIG. 6 shows a thin layer chromatography assay of triacylglceride (TAG) present in extracts obtained from *S. elongatus* PCC 7942 strains that over-expressed either Adp1-DGAT or Sco-DGAT, alone or in combination with a *Synechococcus* sp. PCC 7002 Accase. A control TAG standard is shown.

Methods similar to those described in Example 4 were used to perform TLC and determine how the expression of ADP1-DGAT affected the TAG content in PCC 6803. As shown in FIG. 5A, strains that did not carry ADP1-DGAT did not exhibit TAGs on TLC, while strains that did carry ADP1-DGAT produced TAGs. These experiments demonstrated that the engineered DGAT-dependent production of TAGs first seen in *S. elongatus* sp. strain PCC 7942 is not unique to that strain, but instead is a general property of cyanobacteria engineered to contain a diacyl-glycerol acyltransferase activity.

Example 8

Generation of a Salt-Tolerant *Synechococcus* Elongatus PCC 7942 Strain

*S. elongatus* sp. PCC 7942 is a freshwater, Cyanobacterium that does not ordinarily grow well in high salts. This example describes the generation of a Cyanobacterium *S. elongatus* PCC 7942 mutant that grows in salt or brackish water and can produce TAGs. In addition to being able to grow in freshwater media (BG11), this strain can grow in salt concentrations of up to 3% (in BG11 media).

The mutant *S. elongatus* PCC 7942 strain was selected through several rounds of growth and dilution in high salt (1.5% NaCl) liquid media. Once a salt tolerant strain emerged (after several months of selection), it was tested for its ability to retain salt tolerance after several rounds of growth on BG11 plates made from freshwater. The resulting salt tolerant strain grew to equal density in either BG11 or 1.5% NaCl-BG11 for up to 14 days. The salt tolerant strain grew indistinguishably from wildtype in BG11, but showed a sharp increase in growth compared to wildtype PCC 7942 in media containing NaCl.

An ADP1-DGAT expressing salt tolerant strain of *S. elongatus* PCC 7942 was generated by transforming the salt strain described above with the ADP1-DGAT construct described in Example 1. This ADP1-DGAT salt tolerant strain showed a growth advantage over the ADP1-DGAT non-salt tolerant strain in media containing up to 3% salt and produced similar amounts of TAGs as the ADP1-DGAT parental non salt tolerant strain (FIG. 5B). This strain could be useful in production settings where it may be advantageous to use brackish water or seawater.

The invention claimed is:

1. A modified Cyanobacterium comprising:

an exogenous polynucleotide encoding a diacylglycerol acyltransferase (DGAT) that uses acyl-ACP as a substrate, wherein the modified Cyanobacterium produces a triglyceride, a wax ester or both.

2. The modified Cyanobacterium according to claim 1, wherein the DGAT is a prokaryotic DGAT.

3. The modified Cyanobacterium according to claim 2, wherein said DGAT is an *Acinetobacter* DGAT, a *Streptomyces* DGAT, or an *Alcanivorax* DGAT.

4. The modified Cyanobacterium according to claim 1, wherein said Cyanobacterium is selected from the group consisting of: *Synechoccus elongatus* PCC 7942, a salt tolerant variant of *Synechoccus elongatus* PCC 7942, *Synechococcus* PCC 7002, and *Synechocystis* PCC 6803.

5. The modified Cyanobacterium according to claim 1, wherein said Cyanobacterium is salt tolerant.

6. A method for producing a triglyceride, a wax ester or both, comprising culturing the Cyanobacterium according to claim 1 to produce a triglyceride, a wax ester or both.

7. The method according to claim 6, wherein the DGAT is a prokaryotic DGAT.

8. The method according to claim 7, wherein said DGAT is an *Acinetobacter* DGAT, a *Streptomyces* DGAT, or an *Alcanivorax* DGAT.

9. The method according to claim 6, wherein said Cyanobacterium is selected from the group consisting of: *S. elongatus* PCC 7942, a salt tolerant variant of *S. elongatus* PCC 7942, *Synechococcus* PCC 7002, and *Synechocystis* PCC 6803.

10. The method according to claim 6, wherein said Cyanobacterium is salt tolerant.

11. A method for making a modified Cyanobacterium, comprising modifying a Cyanobacterium by introducing into the Cyanobacterium an exogenous polynucleotide encoding a diacylglycerol acyltransferase (DGAT) that uses acyl-ACP as a substrate, wherein said Cyanobacterium produces a triglyceride, a wax ester or both.

12. The method according to claim 11, wherein said DGAT is an *Acinetobacter* DGAT, a *Streptomyces* DGAT, or an *Alcanivorax* DGAT.

13. The method according to claim 11, wherein said Cyanobacterium is salt tolerant.

14. The method according to claim 11, wherein said Cyanobacterium is selected from the group consisting of: *S. elongatus* PCC 7942, a salt tolerant variant of *S. elongatus* PCC 7942, *Synechococcus* PCC 7002, and *Synechocystis* PCC 6803.

* * * * *